United States Patent
Heo et al.

(10) Patent No.: US 11,228,001 B2
(45) Date of Patent: Jan. 18, 2022

(54) HETERO-CYCLIC COMPOUND AND ORGANIC LIGHT EMITTING DEVICE COMPRISING THE SAME

(71) Applicant: LG CHEM, LTD., Seoul (KR)

(72) Inventors: Dong Uk Heo, Daejeon (KR); Dong Hoon Lee, Daejeon (KR); Jung Oh Huh, Daejeon (KR); Boon Jae Jang, Daejeon (KR); Mi Yeon Han, Daejeon (KR); Min Woo Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 406 days.

(21) Appl. No.: 16/341,884

(22) PCT Filed: Jan. 10, 2018

(86) PCT No.: PCT/KR2018/000486
§ 371 (c)(1),
(2) Date: Apr. 12, 2019

(87) PCT Pub. No.: WO2018/135798
PCT Pub. Date: Jul. 26, 2018

(65) Prior Publication Data
US 2019/0245149 A1 Aug. 8, 2019

(30) Foreign Application Priority Data

Jan. 20, 2017 (KR) .................. 10-2017-0009884
Jan. 5, 2018 (KR) .................. 10-2018-0001717

(51) Int. Cl.
*H01L 51/00* (2006.01)
*C07D 405/10* (2006.01)
(Continued)

(52) U.S. Cl.
CPC ........ *H01L 51/0067* (2013.01); *C07D 251/24* (2013.01); *C07D 307/91* (2013.01);
(Continued)

(58) Field of Classification Search
None
See application file for complete search history.

(56) References Cited

U.S. PATENT DOCUMENTS

| 7,274,141 B2 | 9/2007 | Leo et al. |
| 2015/0069342 A1* | 3/2015 | Lee ............. C07D 409/14 257/40 |

(Continued)

FOREIGN PATENT DOCUMENTS

| EP | 3 072 943 A1 | 9/2016 |
| JP | 2015-526393 A | 9/2015 |

(Continued)

OTHER PUBLICATIONS

IUPAC definition or aryl groups, 2 pages, 1995. (Year: 1995).*

*Primary Examiner* — Robert S Loewe
(74) *Attorney, Agent, or Firm* — Dentons US LLP

(57) ABSTRACT

Disclosed are a heterocyclic compound represented by Formula 1 and an organic light emitting device using the same. The heterocyclic compound is used as a material for hole injection layer, hole transport layer, hole injection and transport layer, light emission layer, electron transport layer, or electron injection layer of the organic light emitting device and provides improved efficiency, low driving voltage, and improved lifetime characteristic.

(Continued)

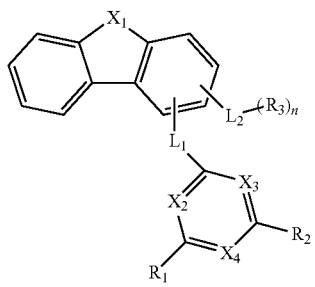

[Chemical Formula 1]

9 Claims, 1 Drawing Sheet

(51) Int. Cl.
| | |
|---|---|
| C07D 409/10 | (2006.01) |
| C07D 405/14 | (2006.01) |
| C07D 307/91 | (2006.01) |
| C07D 251/24 | (2006.01) |
| C07D 333/76 | (2006.01) |
| H01L 51/50 | (2006.01) |
| C07D 405/04 | (2006.01) |
| C07D 409/14 | (2006.01) |

(52) U.S. Cl.
CPC ......... *C07D 333/76* (2013.01); *C07D 405/04* (2013.01); *C07D 405/10* (2013.01); *C07D 405/14* (2013.01); *C07D 409/10* (2013.01); *C07D 409/14* (2013.01); *H01L 51/00* (2013.01); *H01L 51/0073* (2013.01); *H01L 51/0074* (2013.01); *H01L 51/50* (2013.01); *H01L 51/5072* (2013.01); *H01L 51/5092* (2013.01)

(56) References Cited

U.S. PATENT DOCUMENTS

| | | | |
|---|---|---|---|
| 2015/0069347 A1* | 3/2015 | Kim | H01L 51/0054 257/40 |
| 2015/0171336 A1 | 6/2015 | Park et al. | |
| 2015/0336937 A1 | 11/2015 | Lee et al. | |
| 2016/0028021 A1 | 1/2016 | Zeng et al. | |
| 2016/0240792 A1* | 8/2016 | Dyatkin | C07D 209/86 |
| 2017/0047526 A1* | 2/2017 | Chung | C07D 405/14 |
| 2017/0098780 A1* | 4/2017 | Kim | C07D 209/88 |
| 2017/0186965 A1 | 6/2017 | Parham et al. | |
| 2017/0317294 A1* | 11/2017 | Kim | H01L 51/0059 |
| 2017/0369439 A1* | 12/2017 | Jung | H01L 51/0032 |
| 2018/0037546 A1 | 2/2018 | Sugino et al. | |
| 2018/0337348 A1* | 11/2018 | Jung | H01L 51/0072 |
| 2019/0198780 A1* | 6/2019 | Kim | C07D 209/86 |
| 2019/0292169 A1* | 9/2019 | Park | C07D 409/04 |

FOREIGN PATENT DOCUMENTS

| | | |
|---|---|---|
| KR | 10-2000-0051826 A | 8/2000 |
| KR | 10-2014-0132244 A | 11/2014 |
| KR | 10-2015-0069346 A | 6/2015 |
| KR | 10-2015-0076129 A | 7/2015 |
| KR | 10-2016-0006633 A | 1/2016 |
| KR | 10-2016-0028524 A | 3/2016 |
| KR | 10-2016-0112111 A | 9/2016 |
| WO | 03/012890 A2 | 2/2003 |
| WO | 2014/017844 A1 | 1/2014 |
| WO | 2016/129672 A1 | 8/2016 |

* cited by examiner

[FIG. 1]
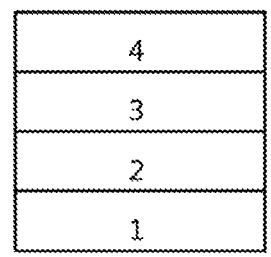
[FIG. 2]
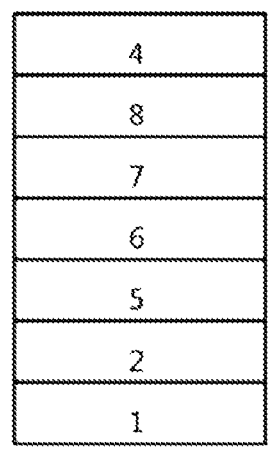

HETERO-CYCLIC COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2018/000486, filed on Jan. 10, 2018, which claims the benefit of priority from Korean Patent Application No. 10-2017-0009884 filed on Jan. 20, 2017, and Korean Patent Application No. 10-2018-0001717 filed on Jan. 5, 2018, the full disclosures of which are incorporated herein by reference.

TECHNICAL FIELD

The present disclosure relates to a novel heterocyclic compound and an organic light emitting device comprising the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

There is a continuing need for the development of new materials for the organic materials used in such organic light emitting devices.

PRIOR ART LITERATURE

Patent Literature (Patent Literature 0001) Korean Patent Laid-open Publication No. 10-2000-0051826

DETAILED DESCRIPTION OF THE INVENTION

Technical Problem

It is an object of the present disclosure to provide a novel heterocyclic compound and an organic light emitting device comprising the same.

Technical Solution

In order to achieve the above object, the present disclosure provides a compound represented by Formula 1 below:

[Formula 1]

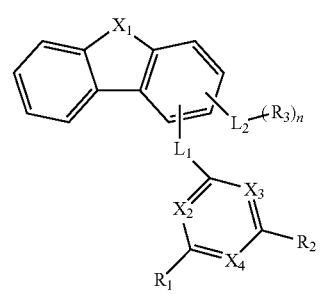

in Formula 1 above, $X_1$ is O or S, $X_2$, $X_3$ and $X_4$ are each independently N or CH, $L_1$ and $L_2$ are each independently a single bond; or a substituted or unsubstituted $C_{6-60}$ arylene; or a substituted or unsubstituted $C_{2-60}$ heteroarylene containing at least one of N, O and S, $R_1$ and $R_2$ are each independently a substituted or unsubstituted $C_{6-60}$ aryl; or a substituted or unsubstituted $C_{2-60}$ heteroaryl containing at least one of N, O and S, $R_3$ is each independently a $C_{6-60}$ aryl substituted with one or two cyano, and n is an integer of 1 or 2.

The present disclosure also provides an organic light emitting device comprising a first electrode; a second electrode provided at a side opposite to the first electrode; and at least one layer of the organic material layers provided between the first electrode and the second electrode, wherein the at least one layer of the organic material layers includes a compound of the present disclosure.

Advantageous Effects

The compound represented by the Formula 1 can be used as a material of an organic material layer of an organic light emitting device, and can achieve an improvement of the efficiency, a low driving voltage and/or an improvement of the lifetime characteristic when applied to the organic light emitting device. In particular, the compound represented by the Formula 1 can be used as hole injection, hole transport, hole injection and transport, light emission, electron transport, or electron injection materials.

BRIEF DESCRIPTION OF DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present disclosure will be described in more detail.

The present disclosure provides a compound represented by Formula 1 below:

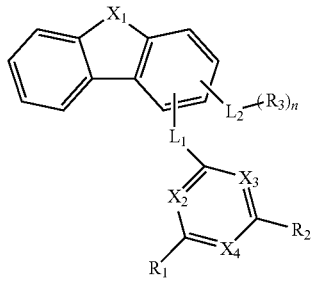

[Formula 1]

in Formula 1 above, $X_1$ is O or S, $X_2$, $X_3$ and $X_4$ are each independently N or —CH, $L_1$ and $L_2$ are each independently a single bond; or a substituted or unsubstituted $C_{6-60}$ arylene; or a substituted or unsubstituted $C_{2-60}$ heteroarylene containing at least one of N, O and S, $R_1$ and $R_2$ are each independently a substituted or unsubstituted $C_{6-60}$ aryl; or a substituted or unsubstituted $C_{2-60}$ heteroaryl containing at least one of N, O and S, $R_3$ is each independently a $C_{6-60}$ aryl substituted with one or two cyano, and n is an integer of 1 or 2.

In the present specification,

or mean a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are linked" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40 carbon atoms. Specifically, the carbonyl group may be compounds having the following structures, but is not limited thereto.

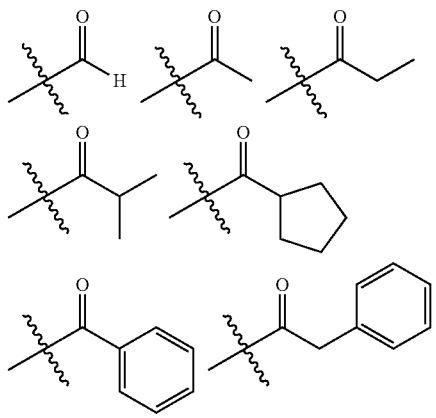

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

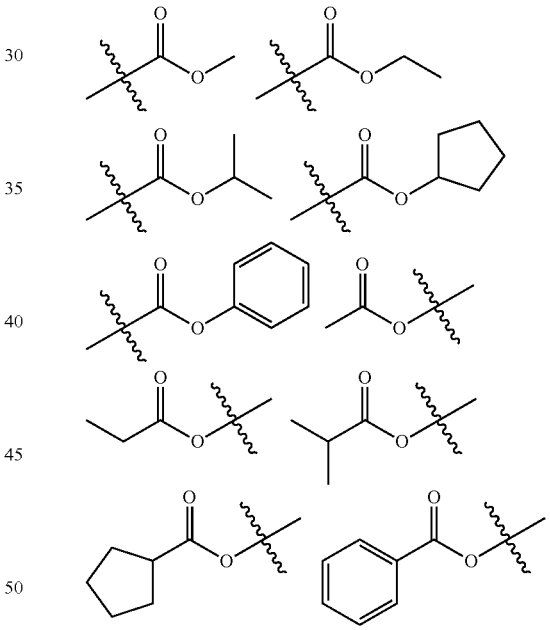

In the present specification, the number of carbon atoms in an imide group is not particularly limited, but is preferably 1 to 25. Specifically, the imide group may be compounds having the following structures, but is not limited thereto.

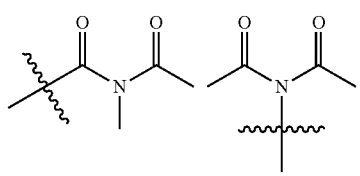

-continued

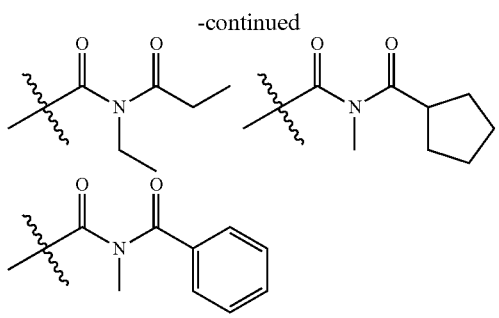

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, an alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group or the like, but is not limited thereto.

In the present specification, a fluorenyl group may be substituted, and two substituent groups may be linked with each other to form a spiro structure. In the case where the fluorenyl group is substituted,

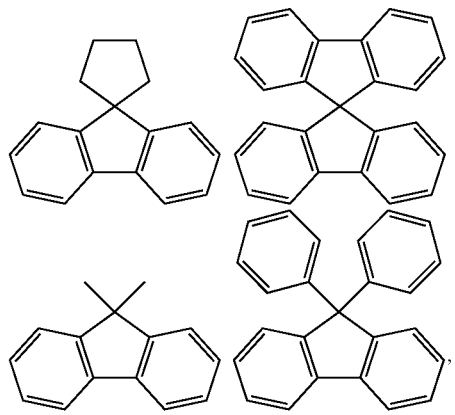

and the like can be formed. However, the structure is not limited thereto.

In the present specification, the heterocyclic group is a heterocyclic group containing at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamines can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

In Formula 1, preferably, at least two of $X_2$, $X_3$ and $X_4$ may be N, and the remainder is CH. That is, the compound represented by the Formula 1 may be represented by any one of Formulas 1-1 to 1-3 below.

[Formula 1-1]

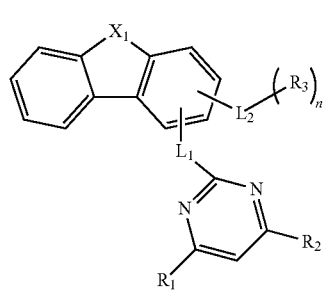

[Formula 1-2]

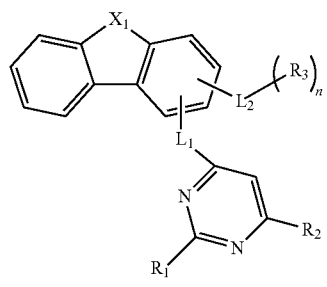

[Formula 1-3]

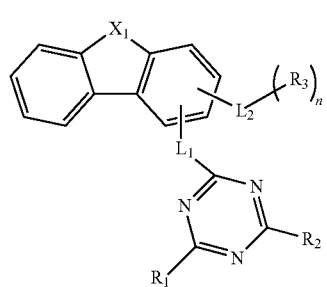

Preferably, $L_1$ and $L_2$ are each independently a single bond, or any one selected from the group consisting of the following:

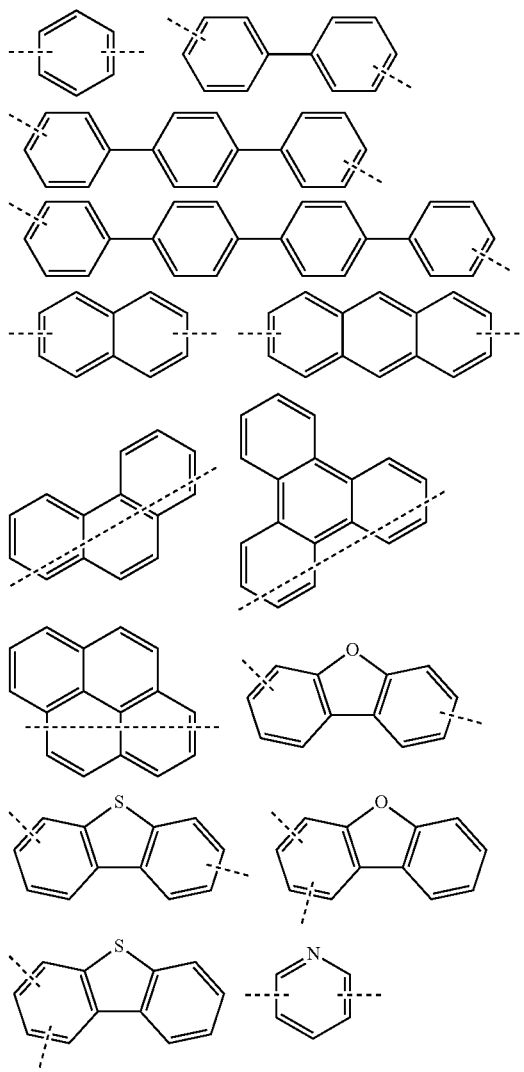

More preferably, $L_1$ and $L_2$ may be each independently a single bond,

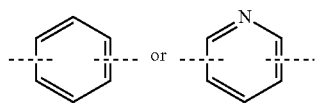

Preferably, $R_1$ and $R_2$ may be each independently any one selected from the group consisting of the following:

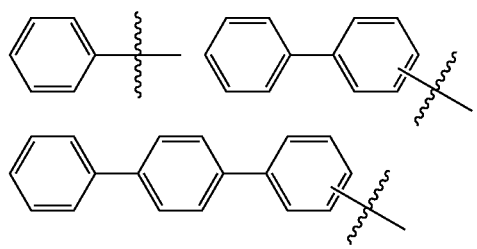

-continued

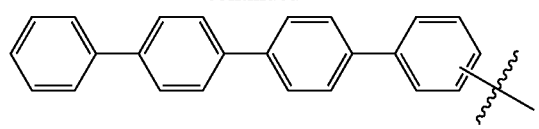
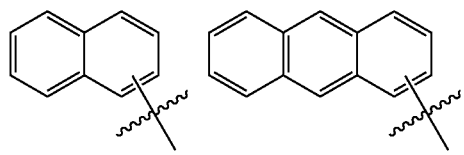
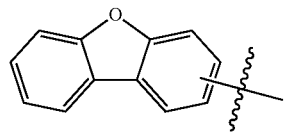
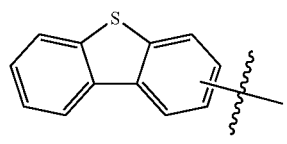
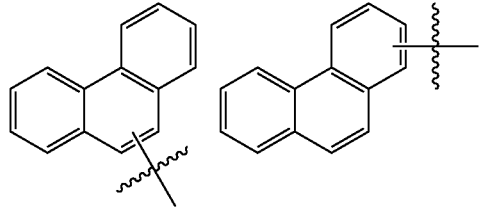
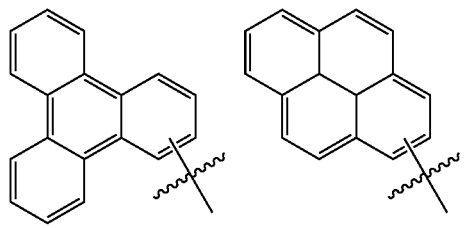
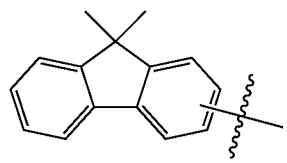

More preferably, $R_1$ and $R_2$ may be each independently

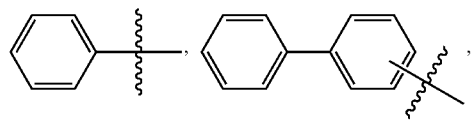
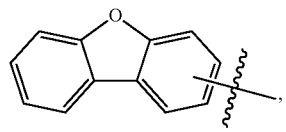
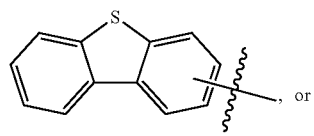, or

-continued

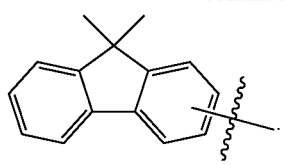

Preferably, each $R_3$ may be independently any one selected from the group consisting of phenyl substituted with one or two cyano, biphenylyl substituted with one or two cyano, terphenylyl substituted with one or two cyano, or dimethylfluorenyl substituted with one or two cyano.

Preferably, the compound represented by the Formula 1 is any one selected from the group consisting of the following:

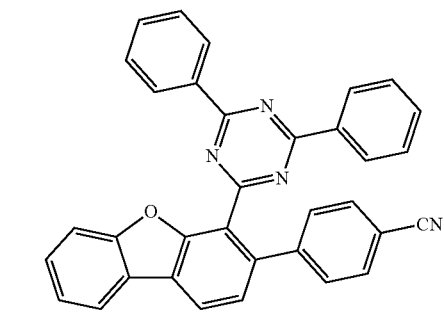
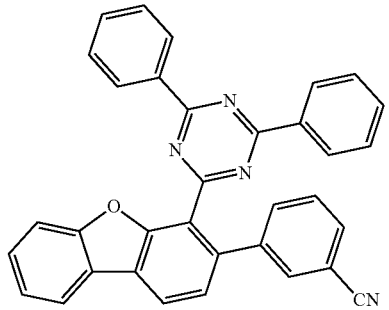
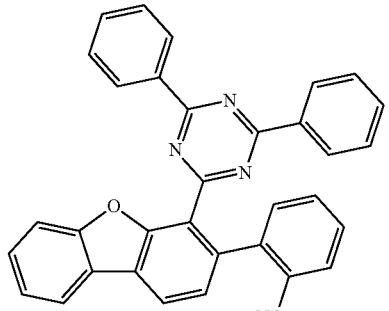
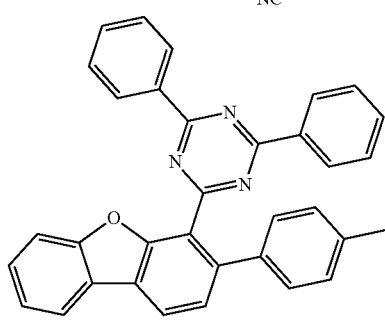

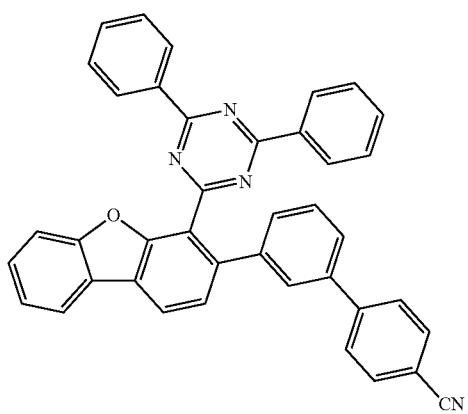
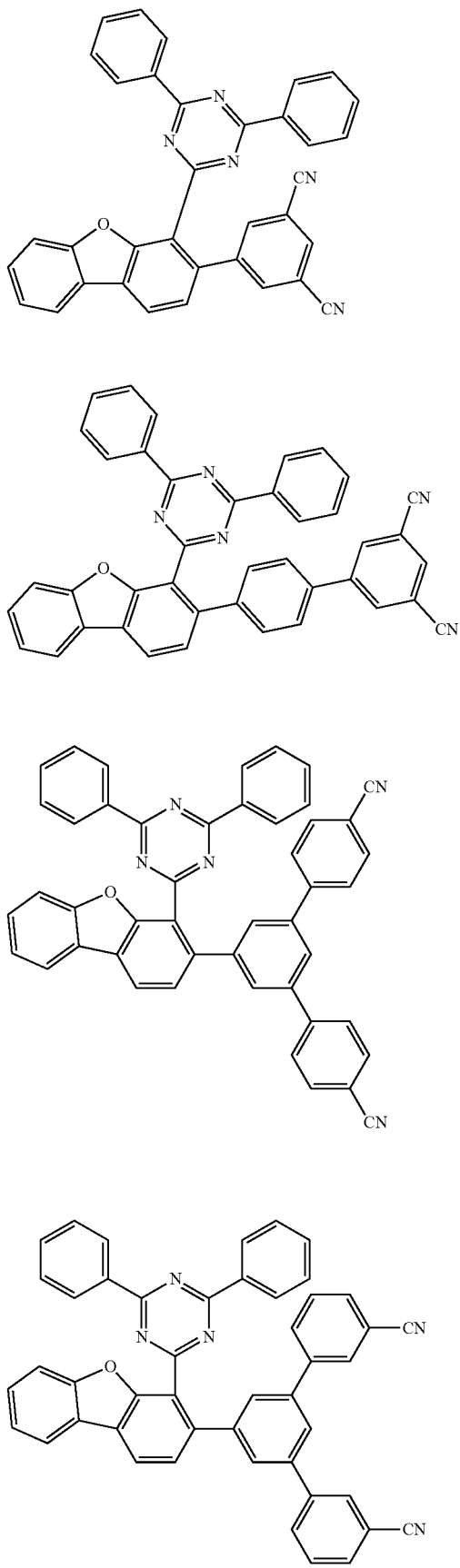

-continued
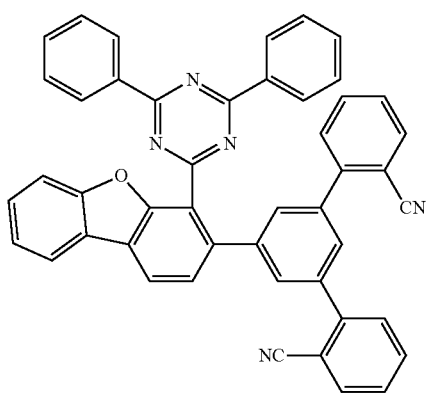
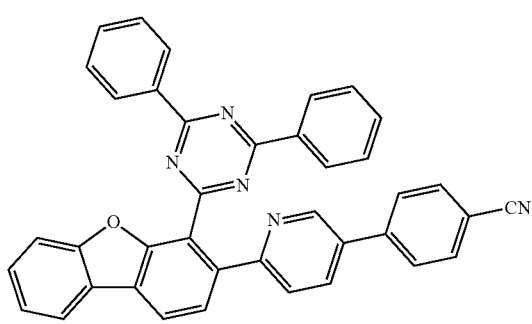
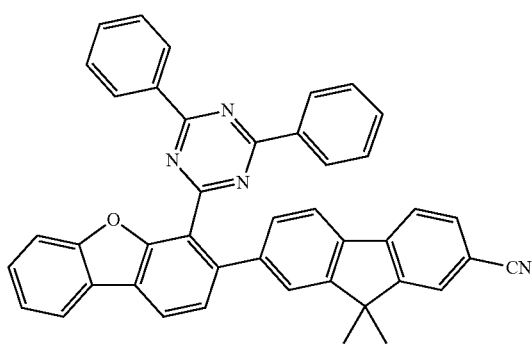
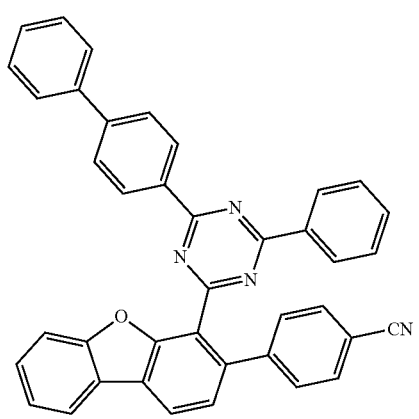
-continued
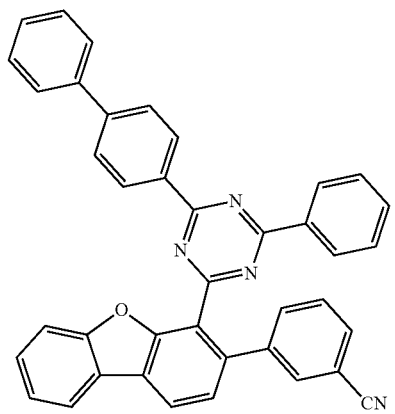

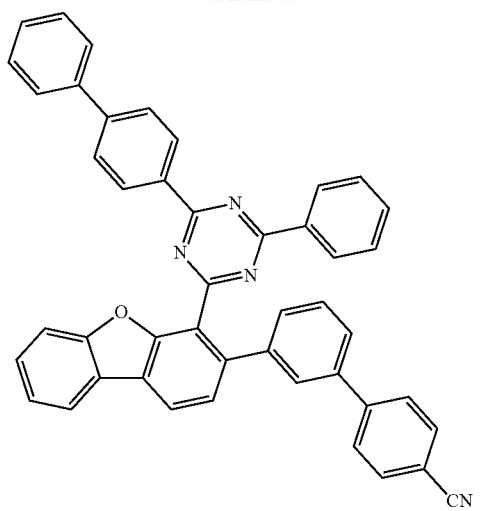
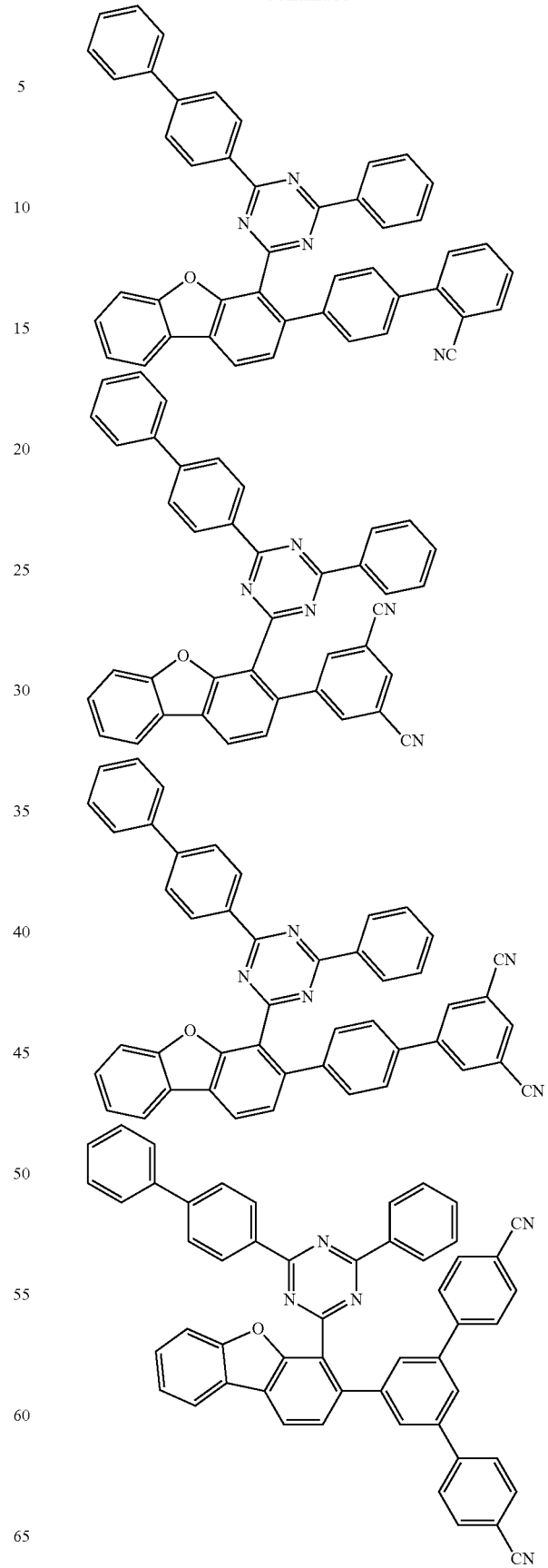

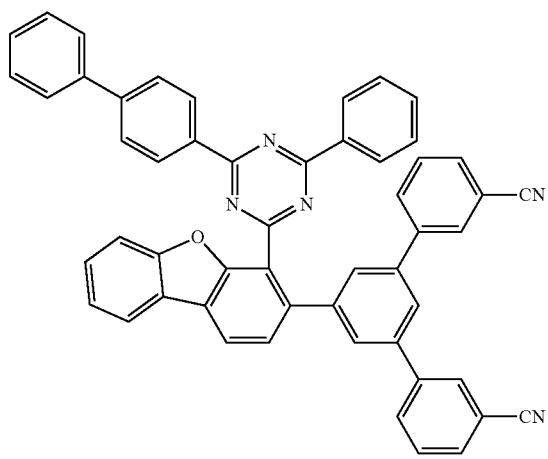
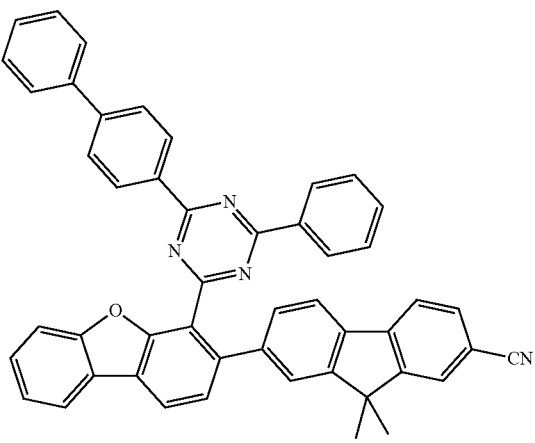
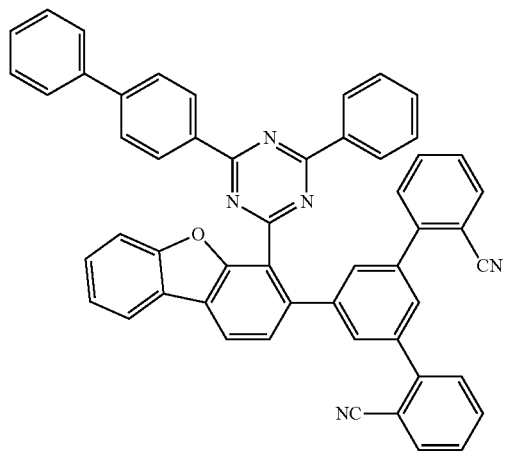
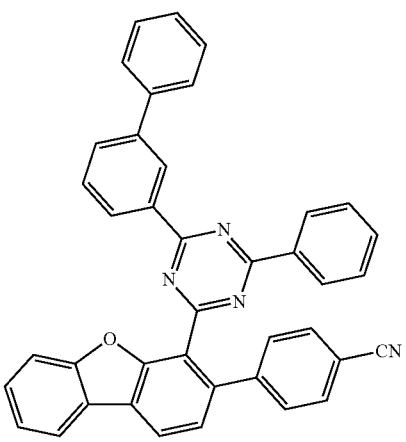
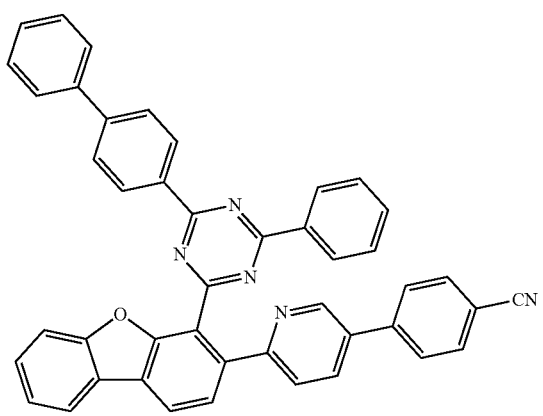
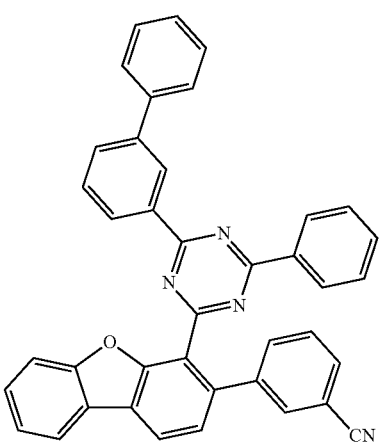

-continued
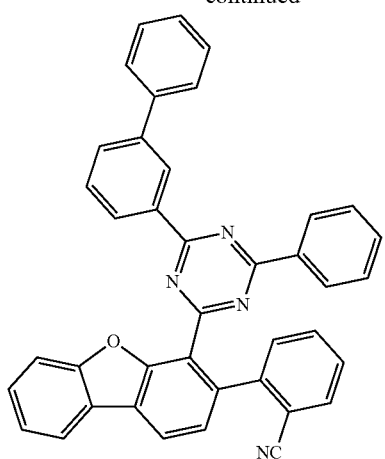
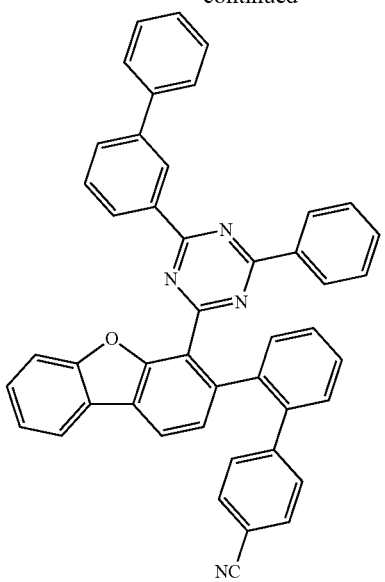
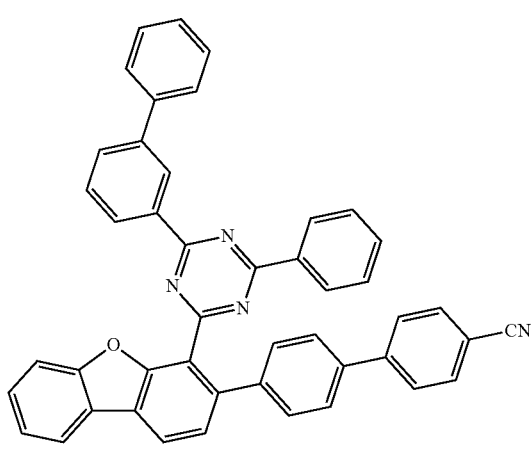
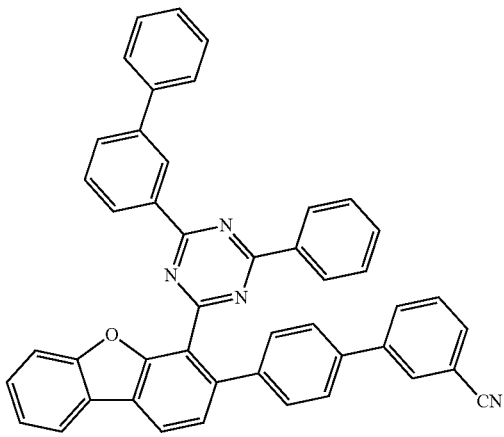
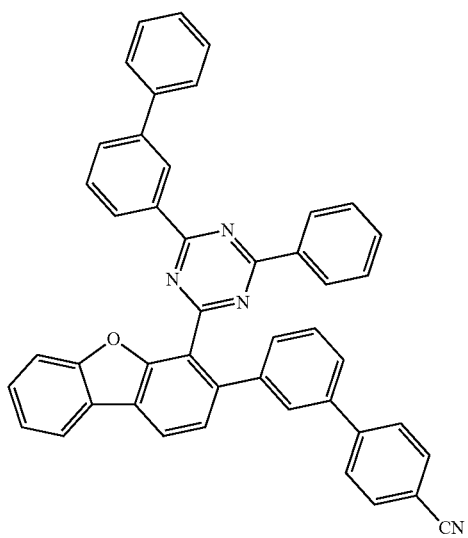
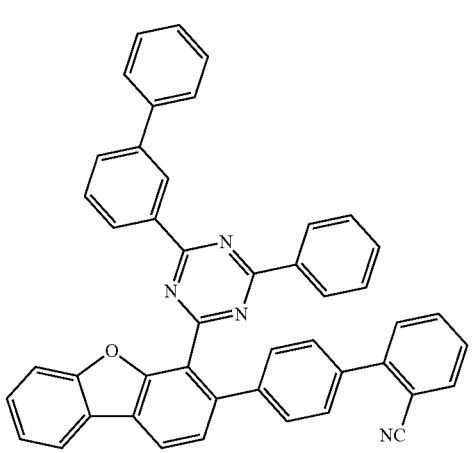

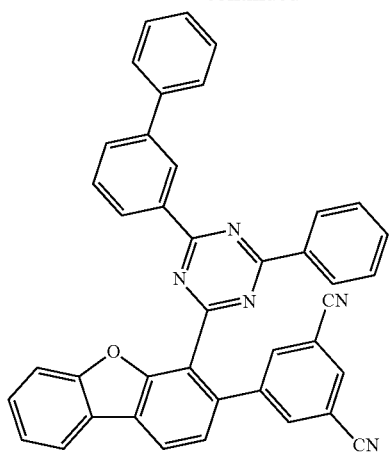
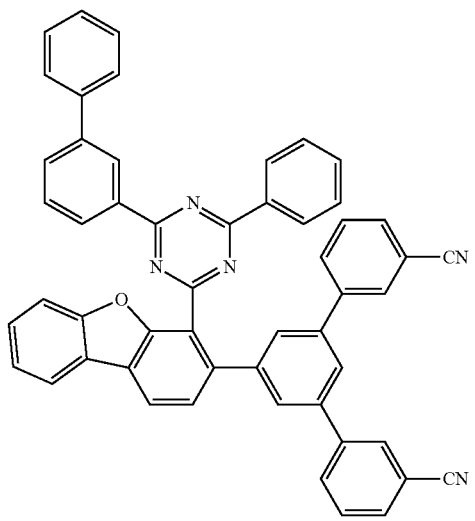
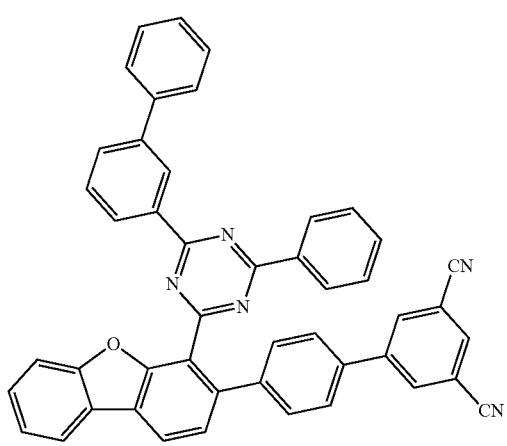
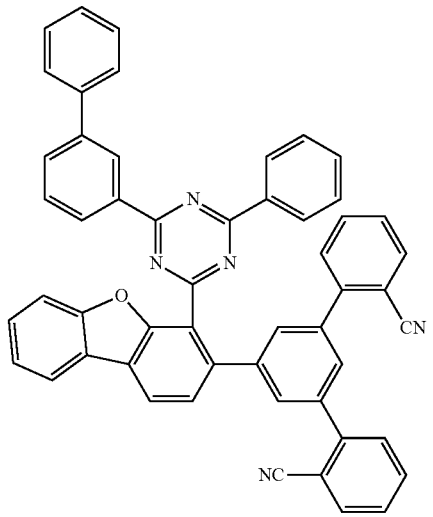
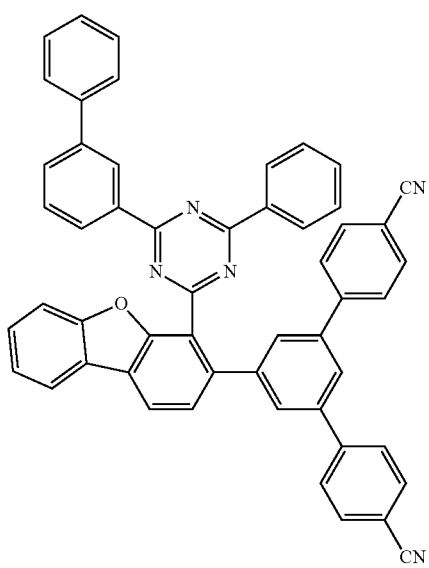
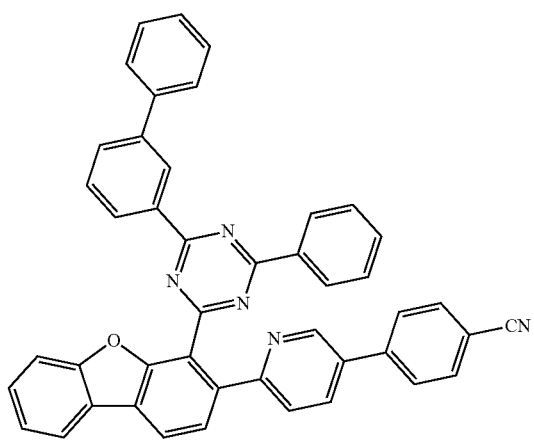 [SMILES: N#Cc1ccc(-c2ccc(-c3ccc4c(oc5ccccc54)c3-c3nc(-c4ccccc4)nc(-c4cccc(-c5ccccc5)c4)n3)nc2)cc1]

-continued
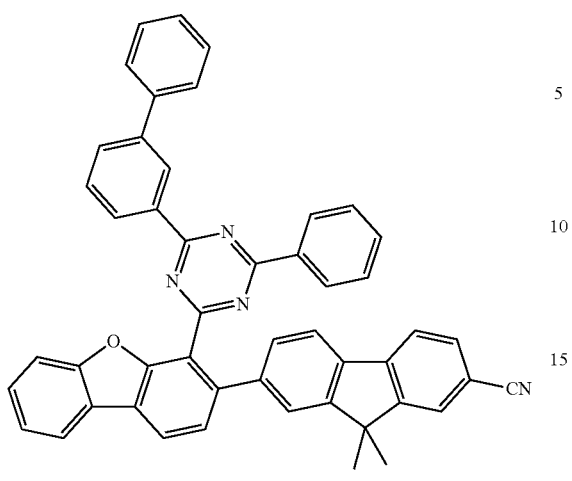
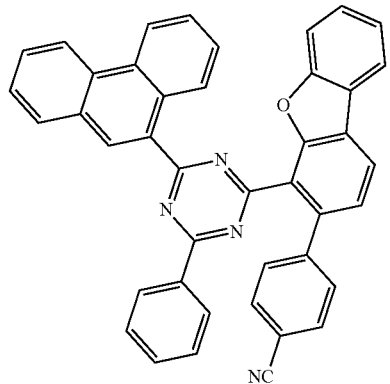
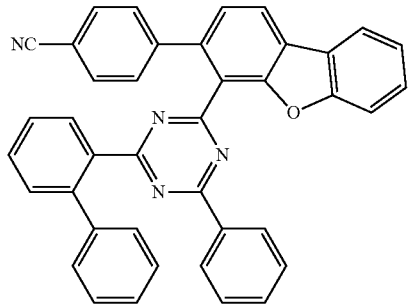
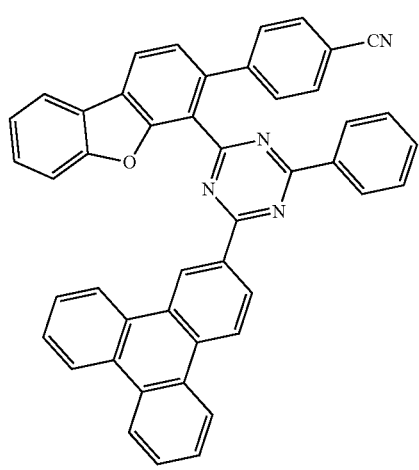
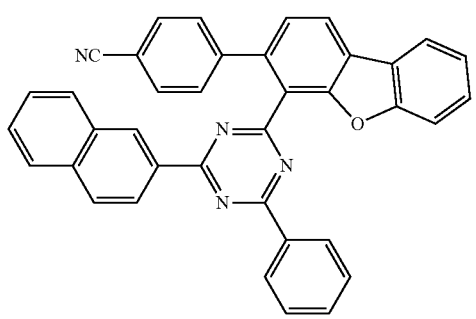
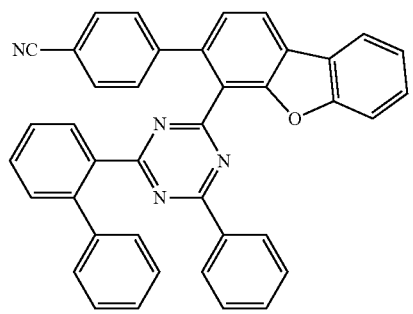
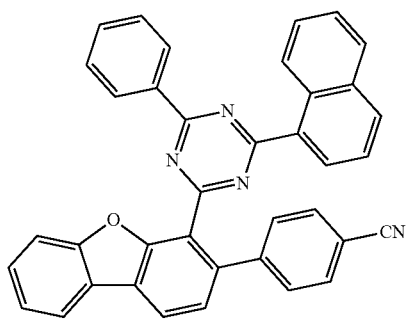
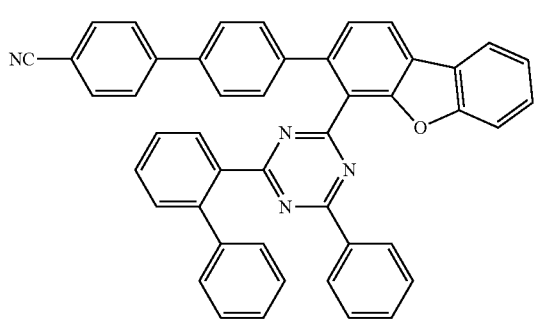

25
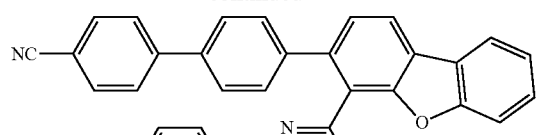
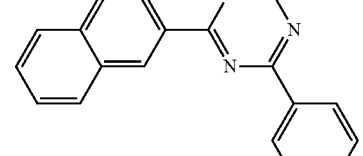
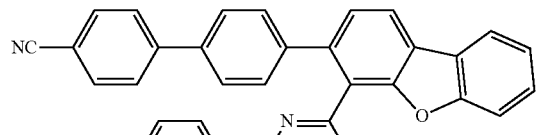
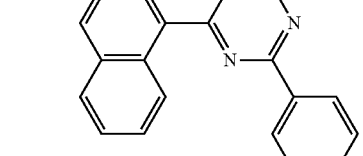
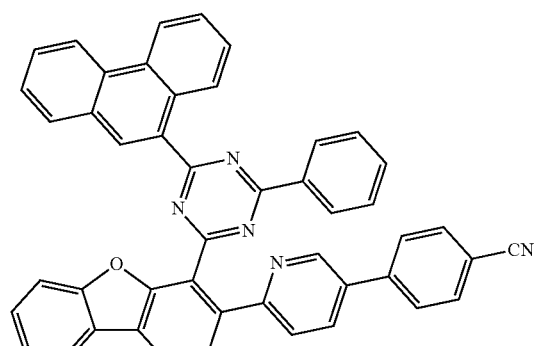
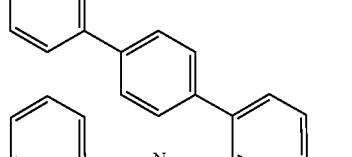
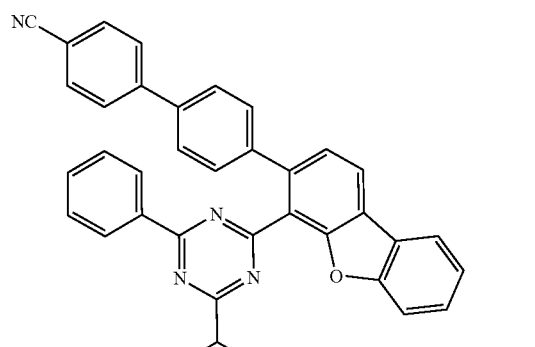
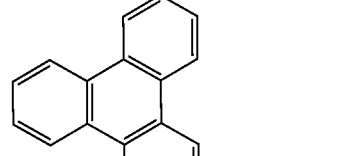
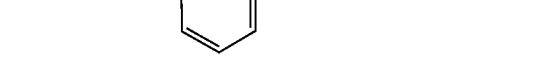
26
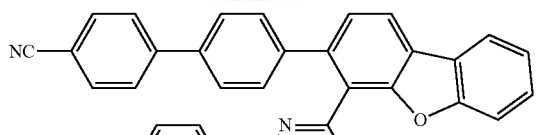
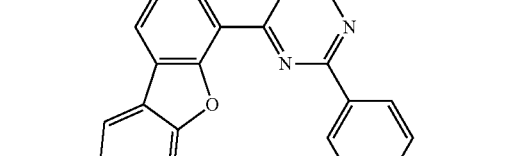
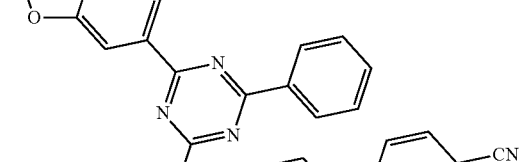
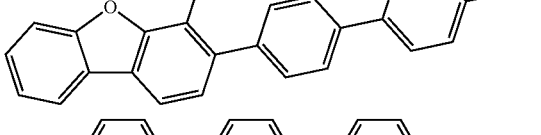
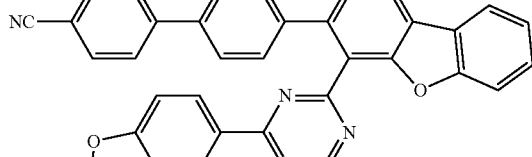
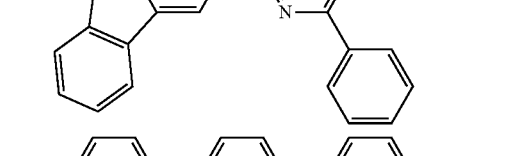
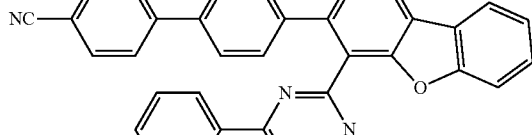
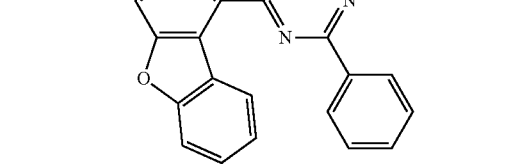
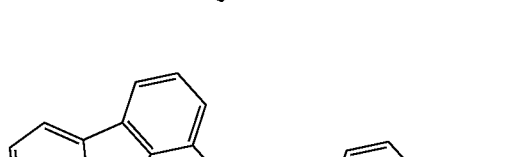
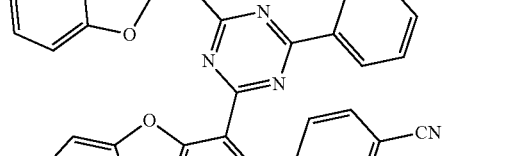
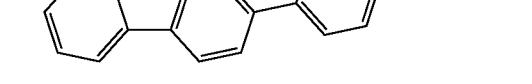

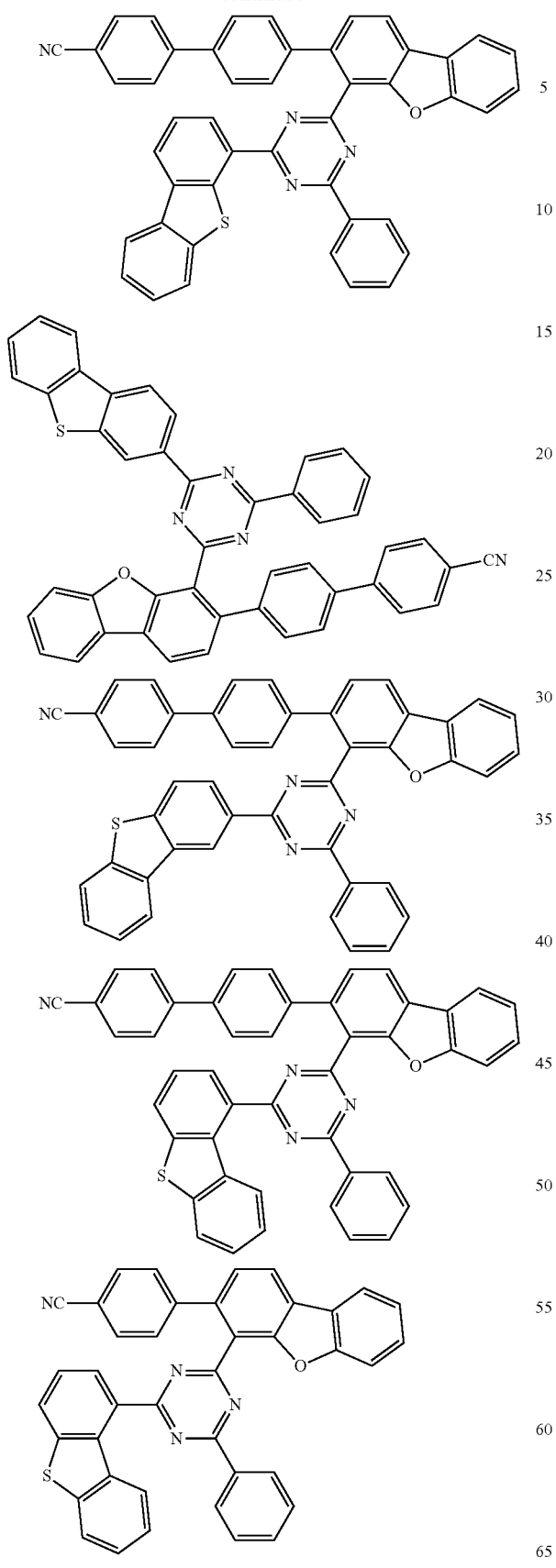
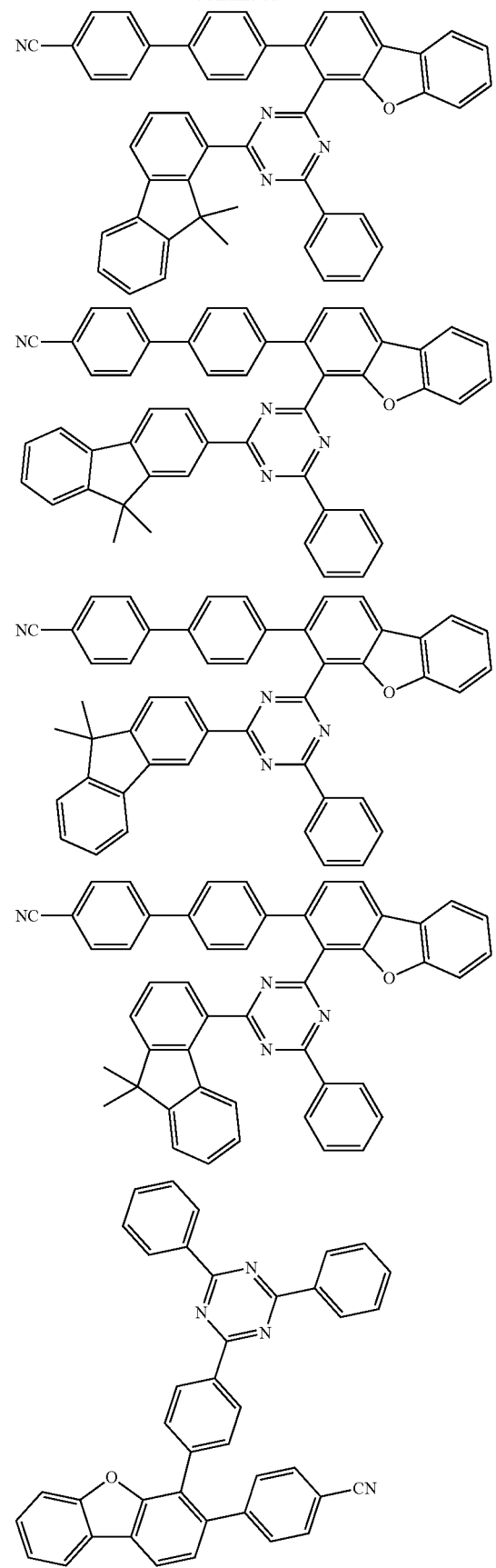

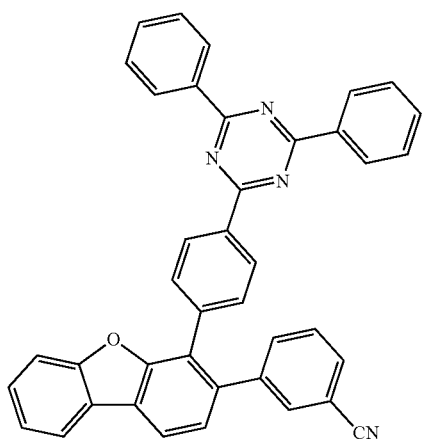
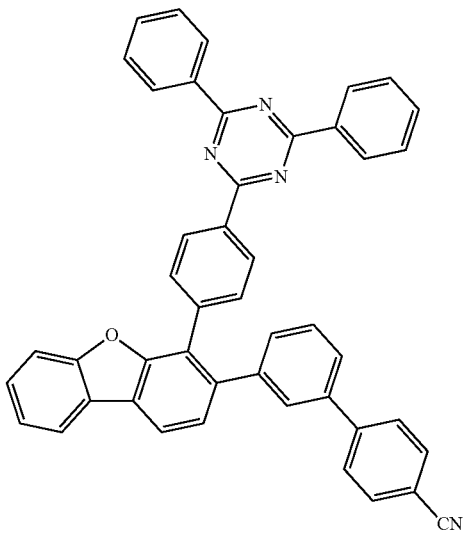
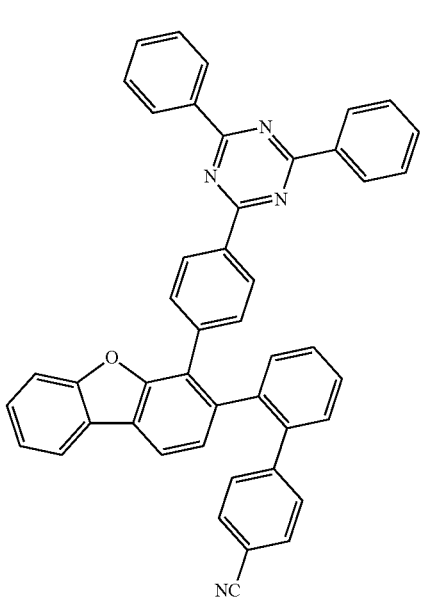
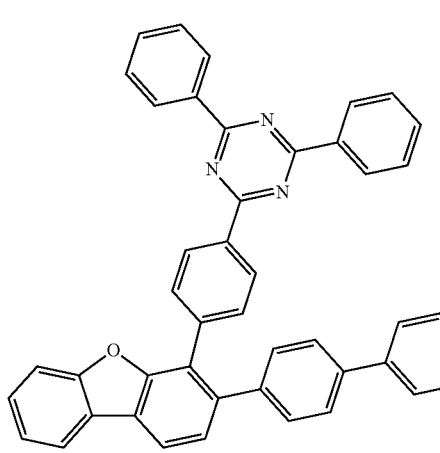
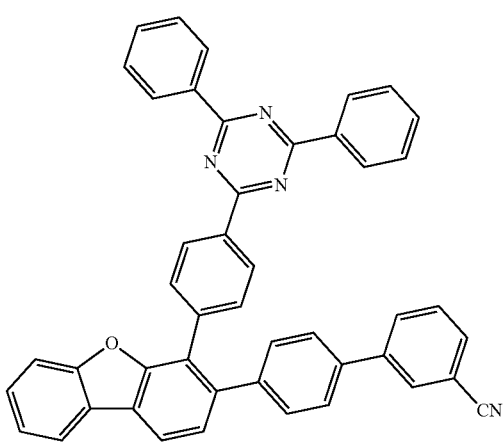

31
-continued
32
-continued
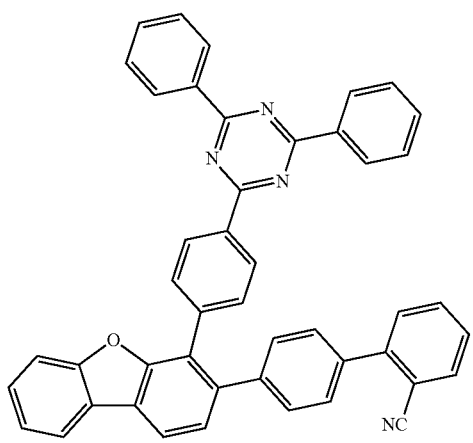
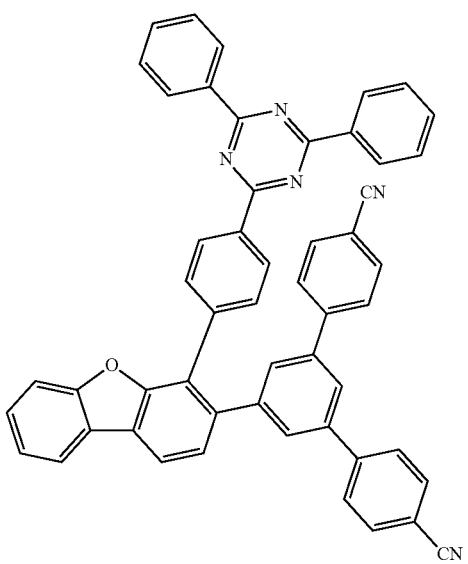
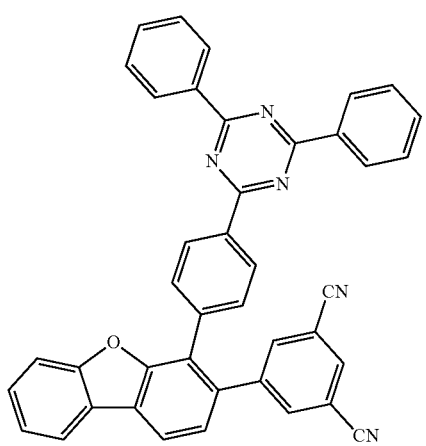
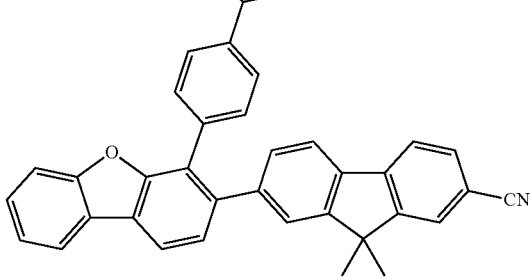
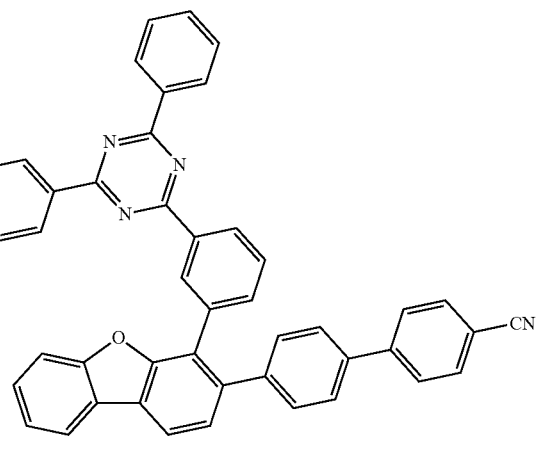

-continued
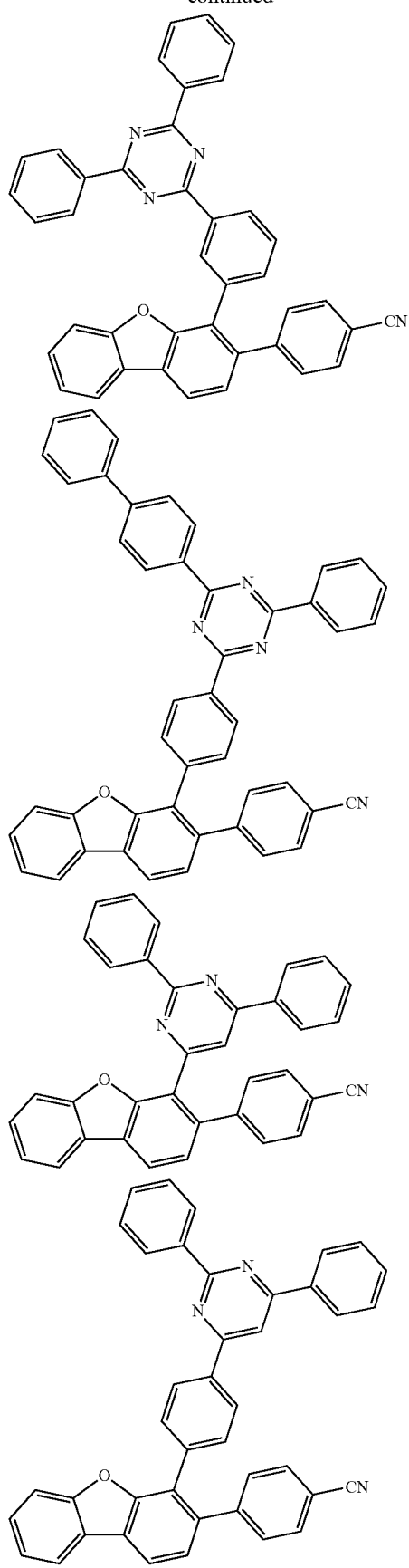
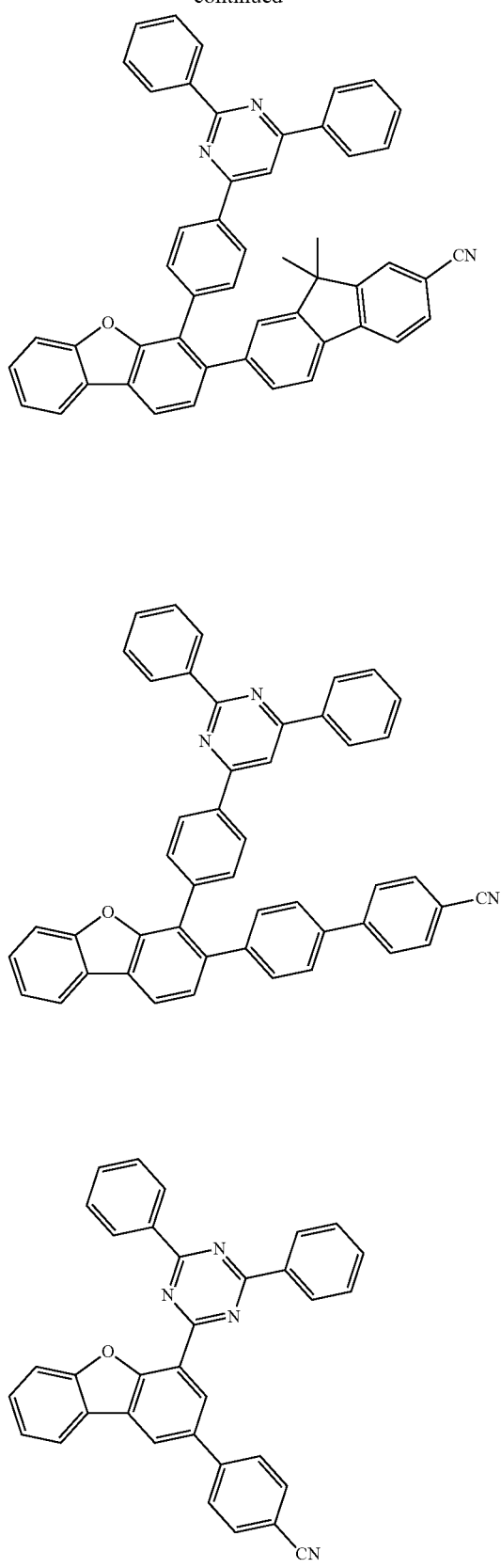

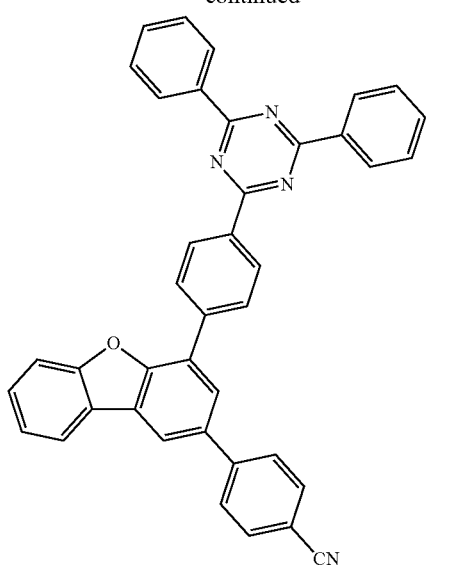
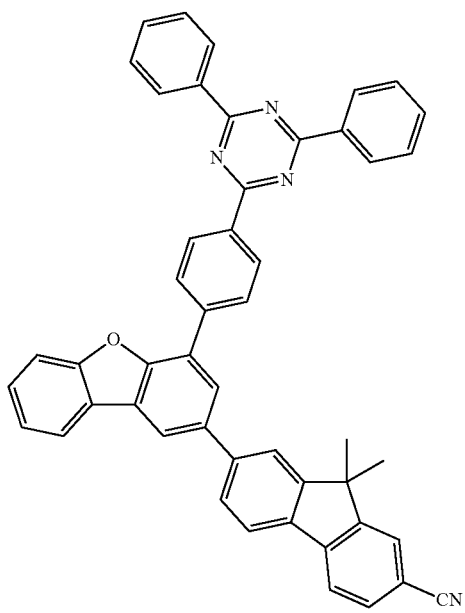 [SMILES: CC1(C)c2cc(C#N)ccc2-c2ccc(-c3cc(-c4ccc(-c5nc(-c6ccccc6)nc(-c6ccccc6)n5)cc4)c4oc5ccccc5c4c3)cc21]
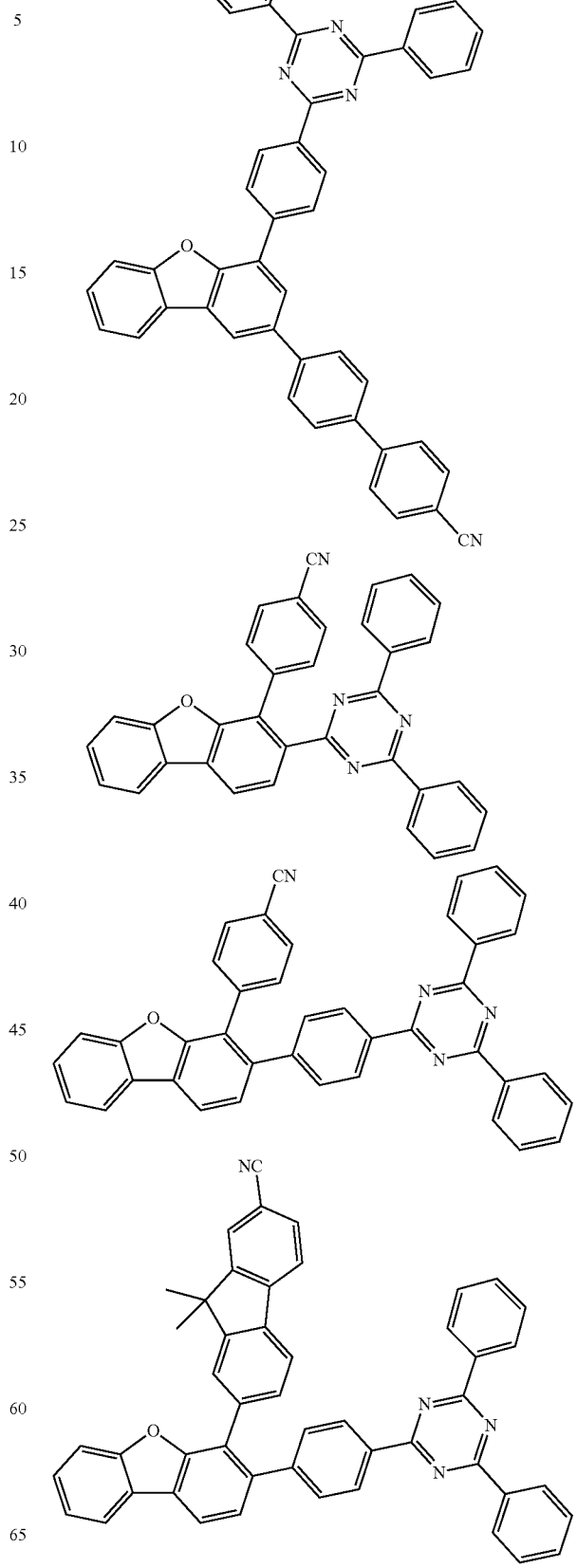

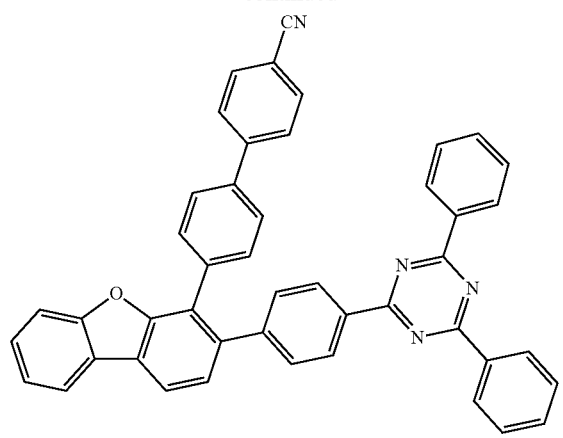
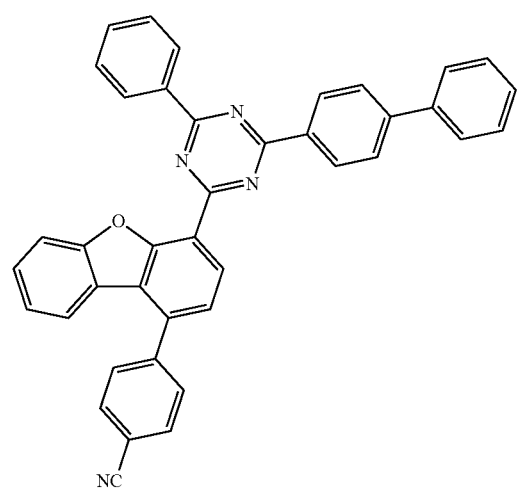
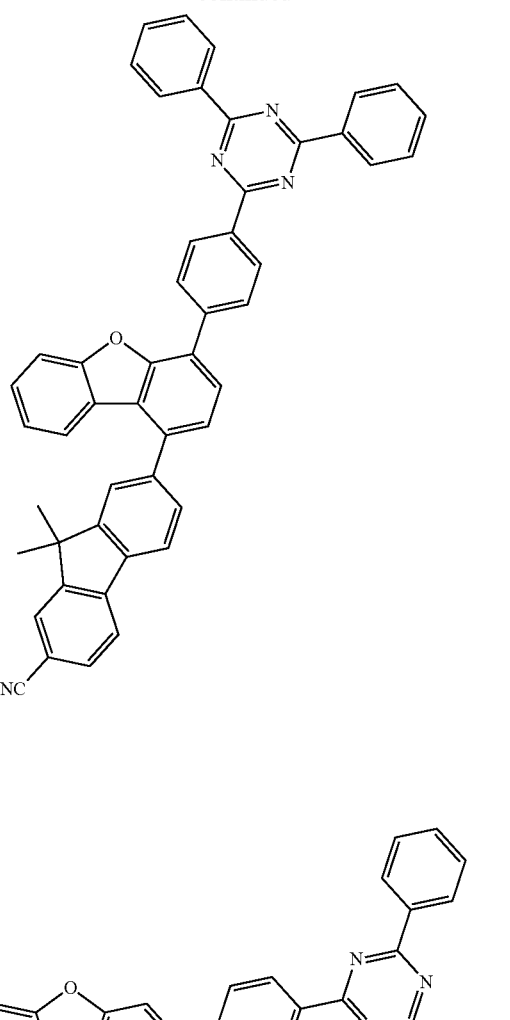
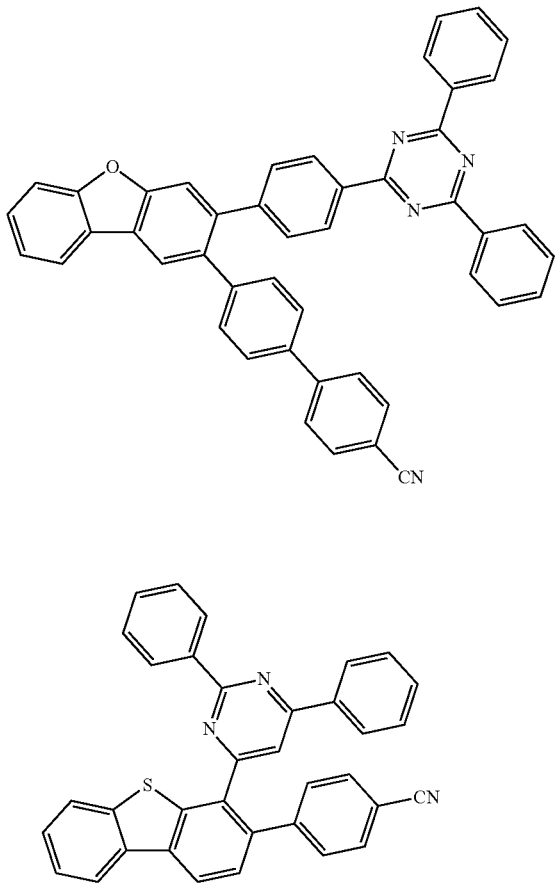

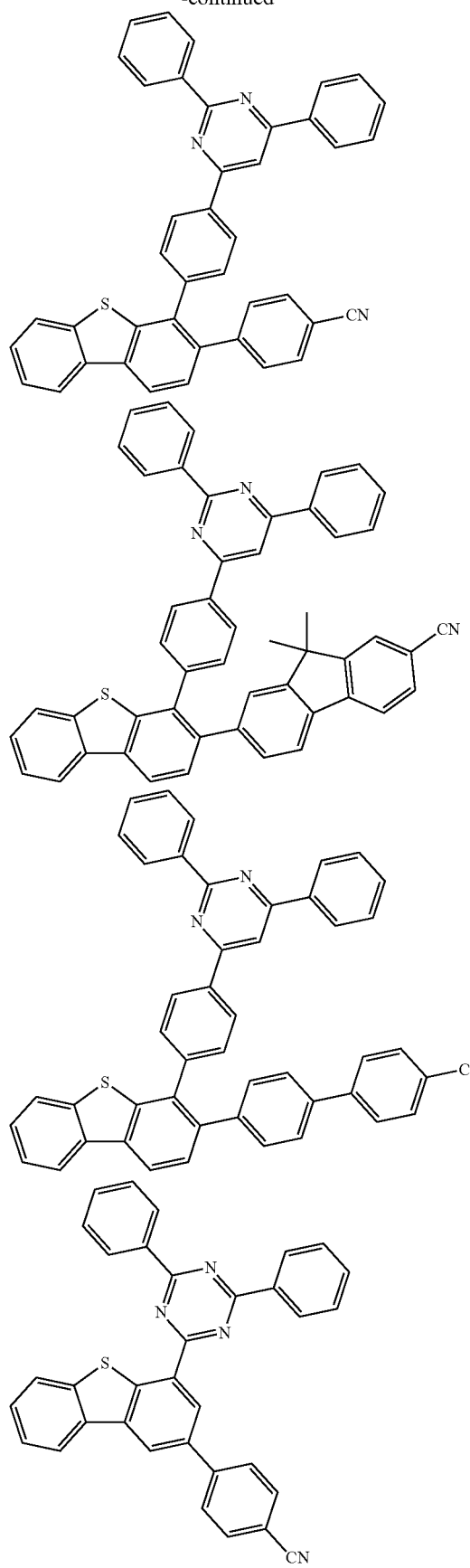
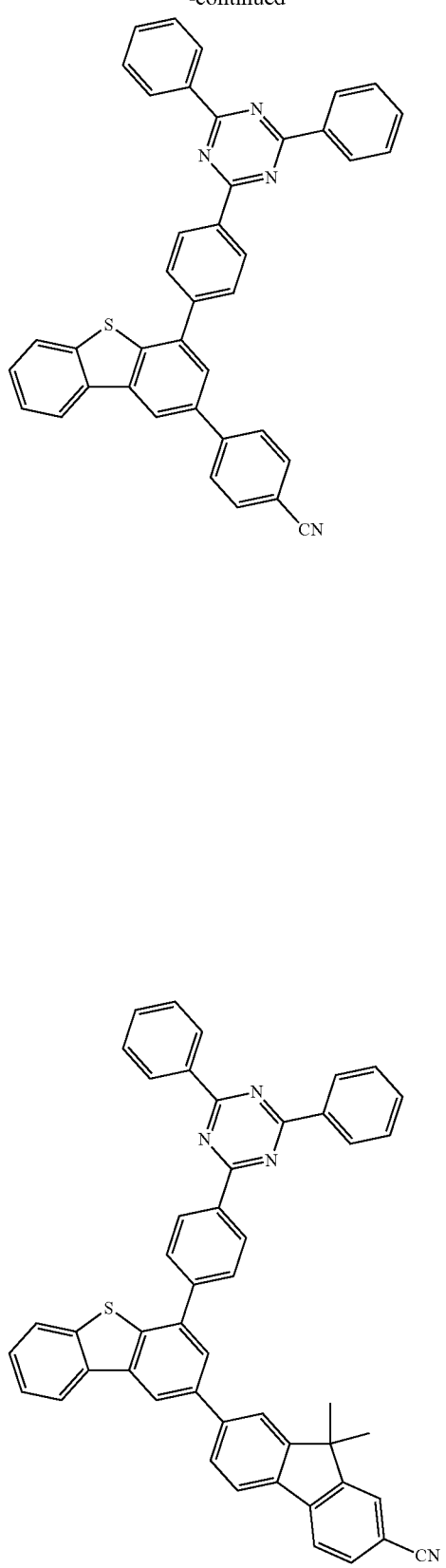

41
-continued
42
-continued
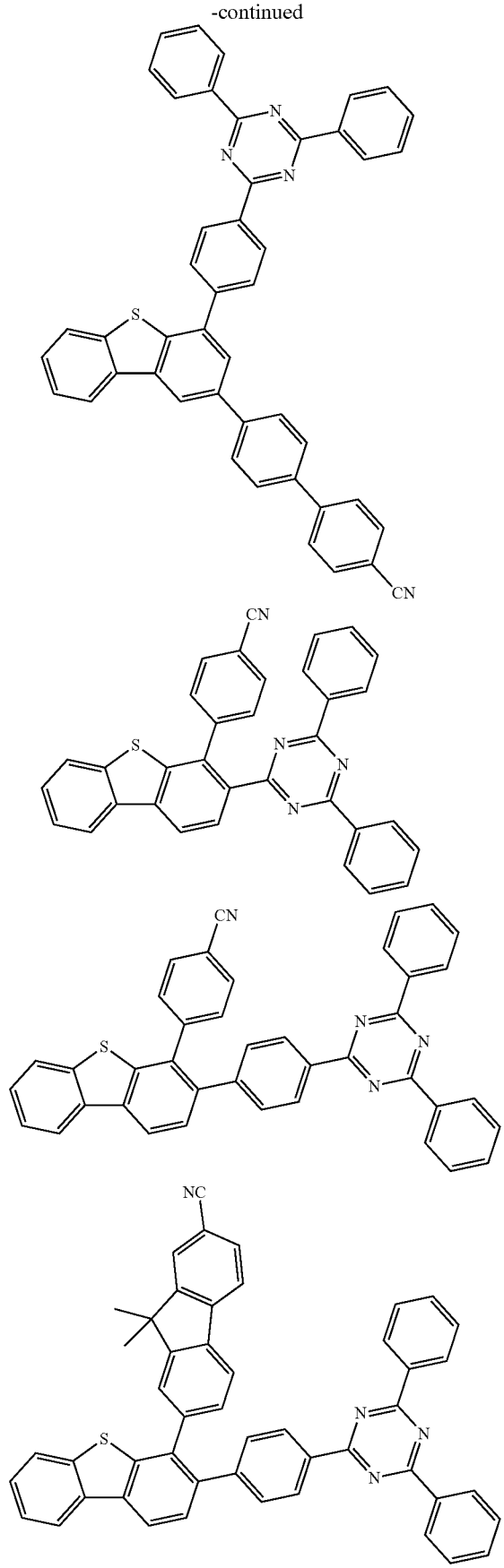
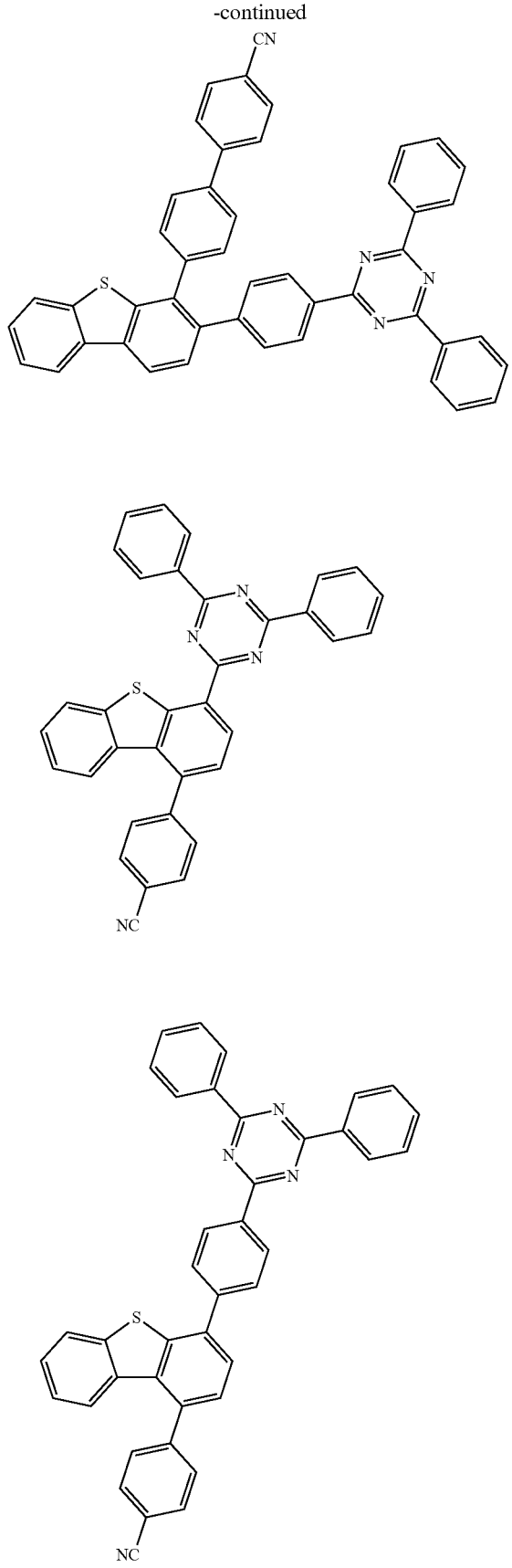

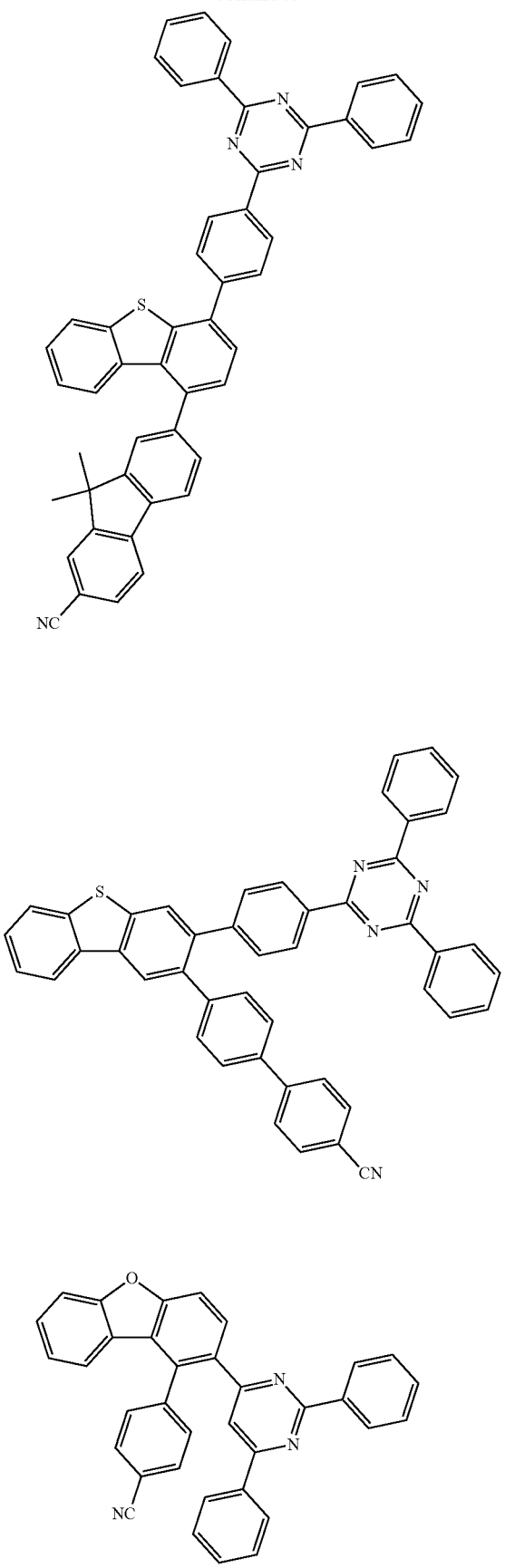
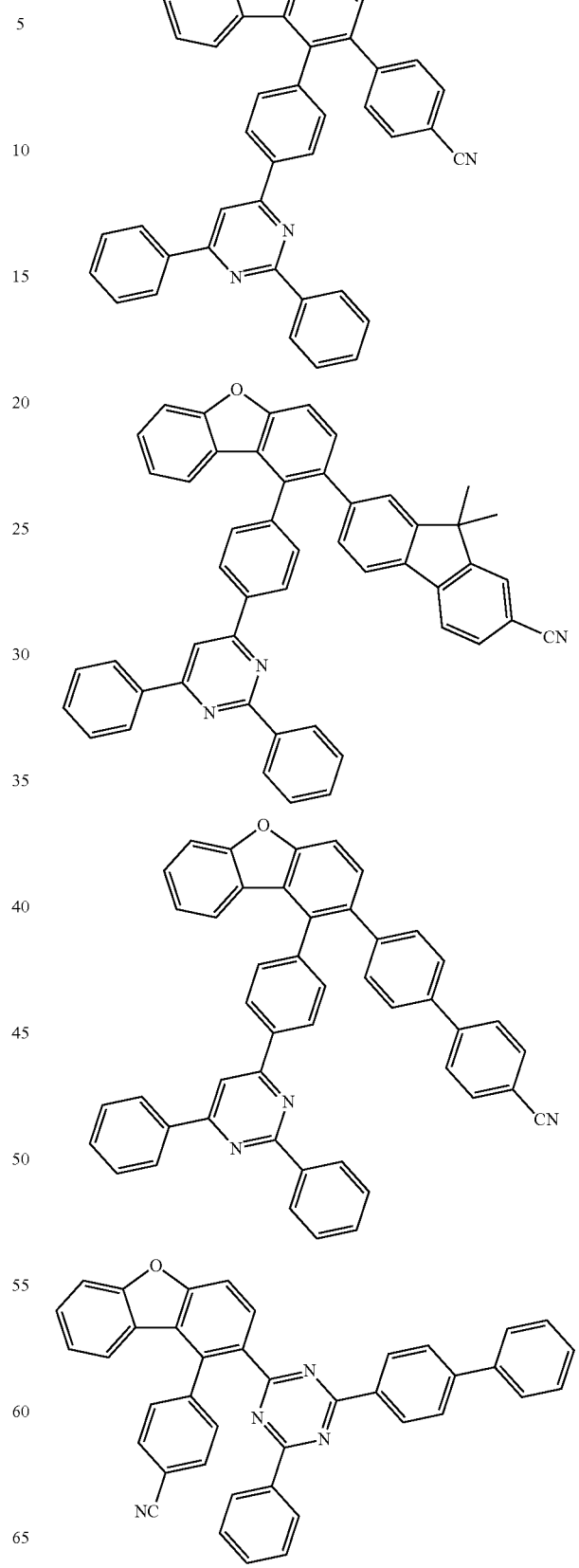

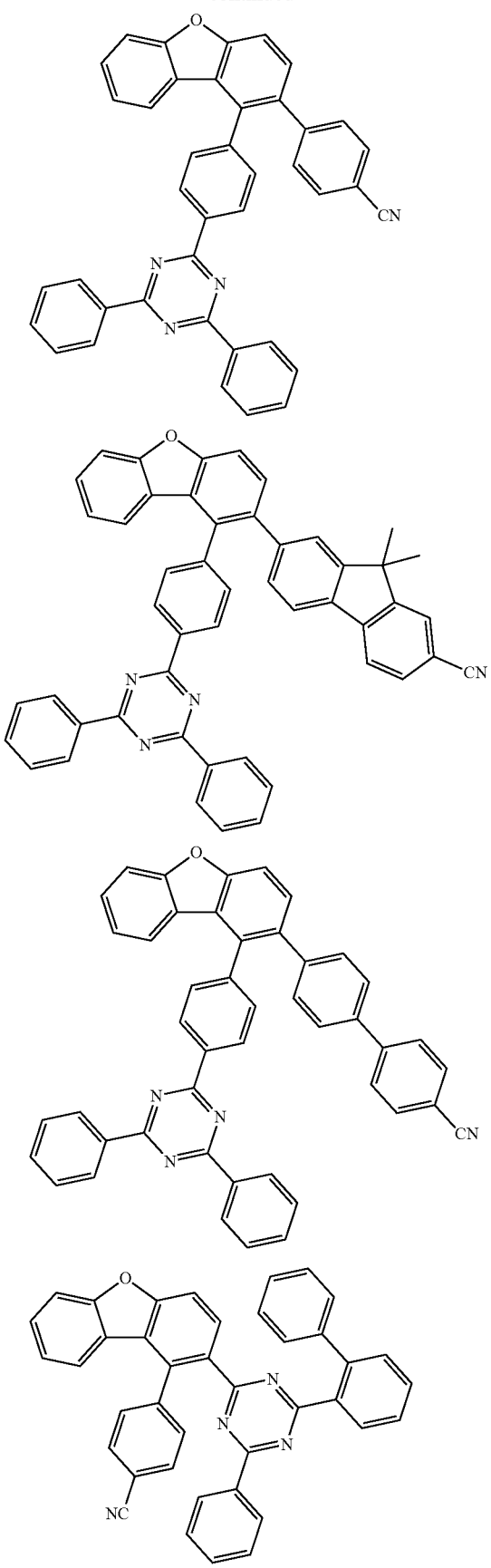
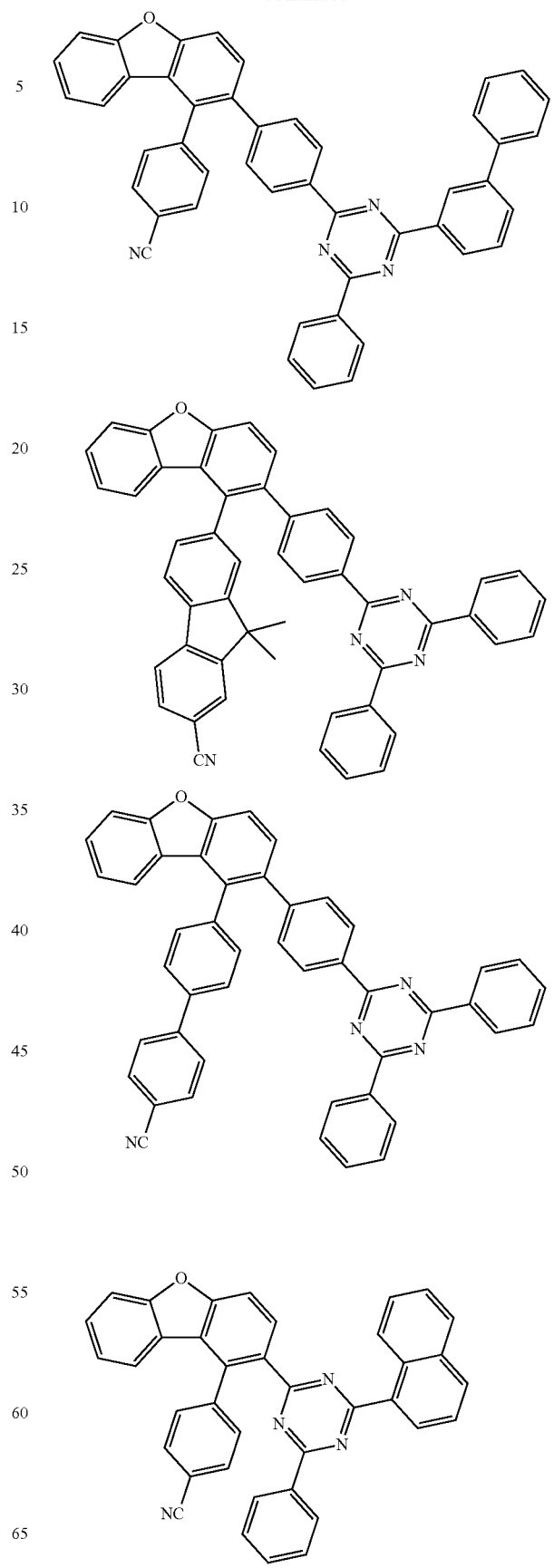

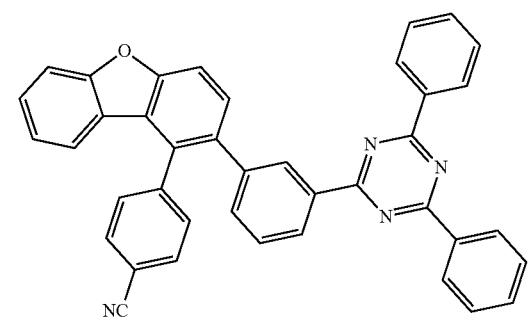
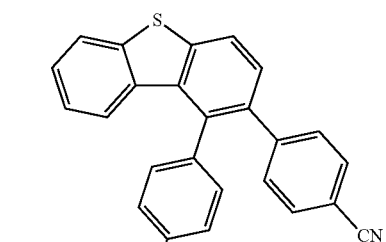
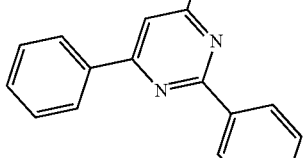
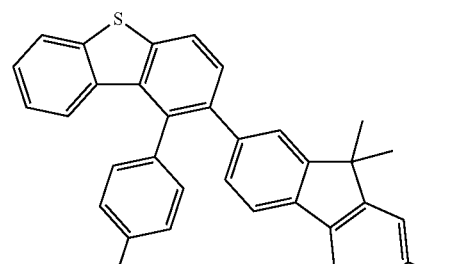
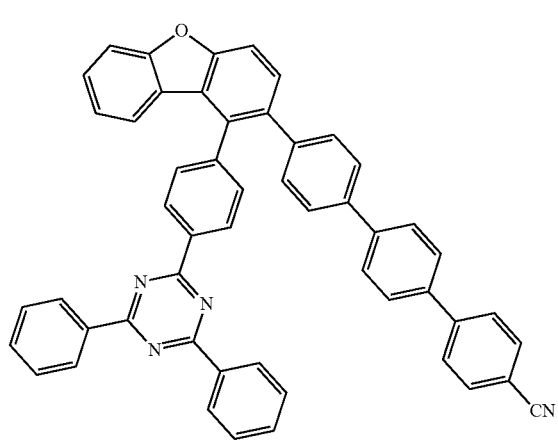
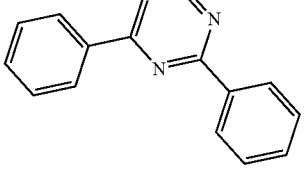
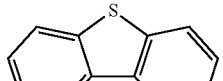
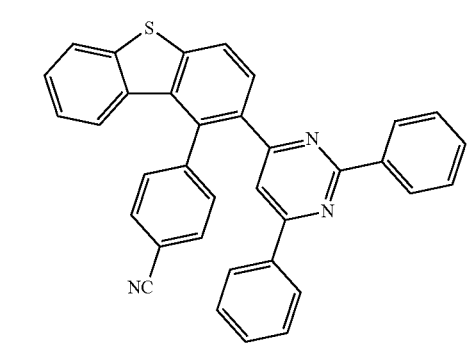
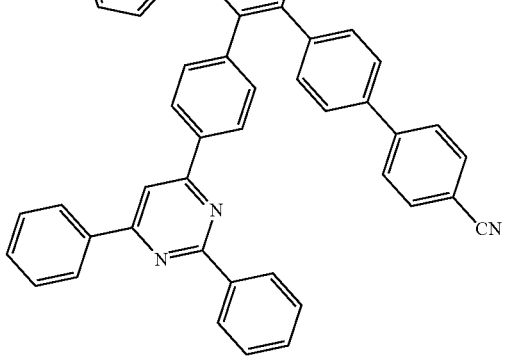
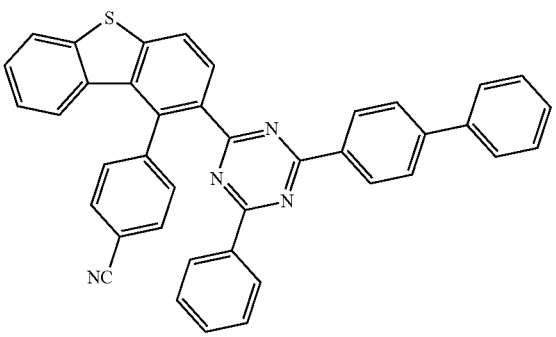

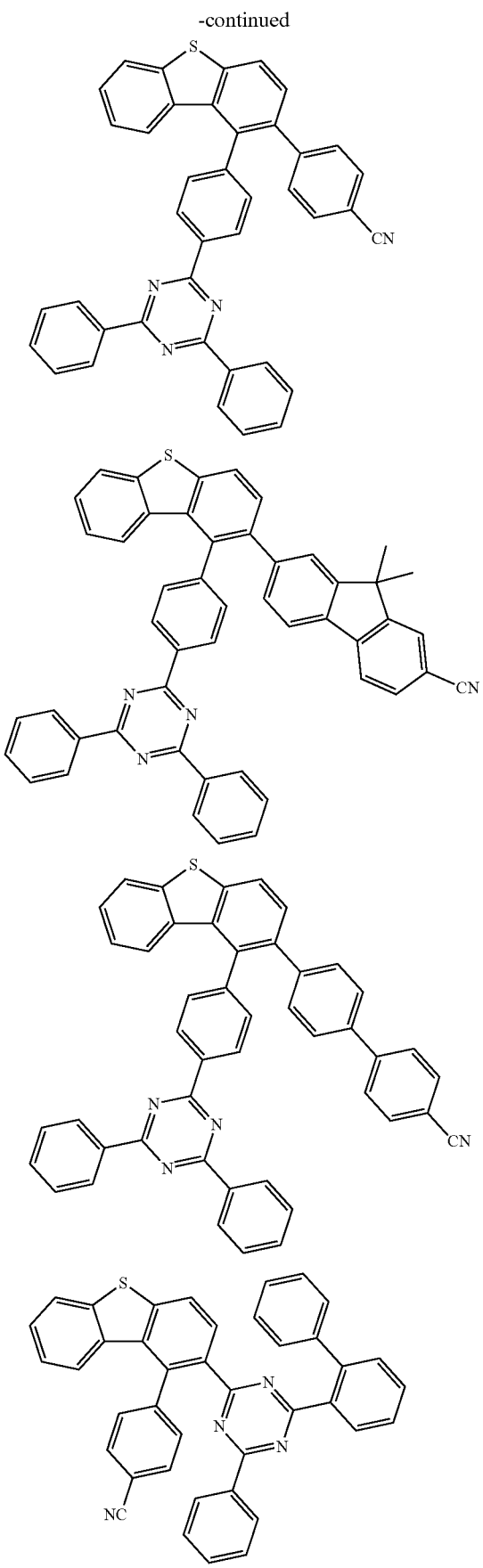
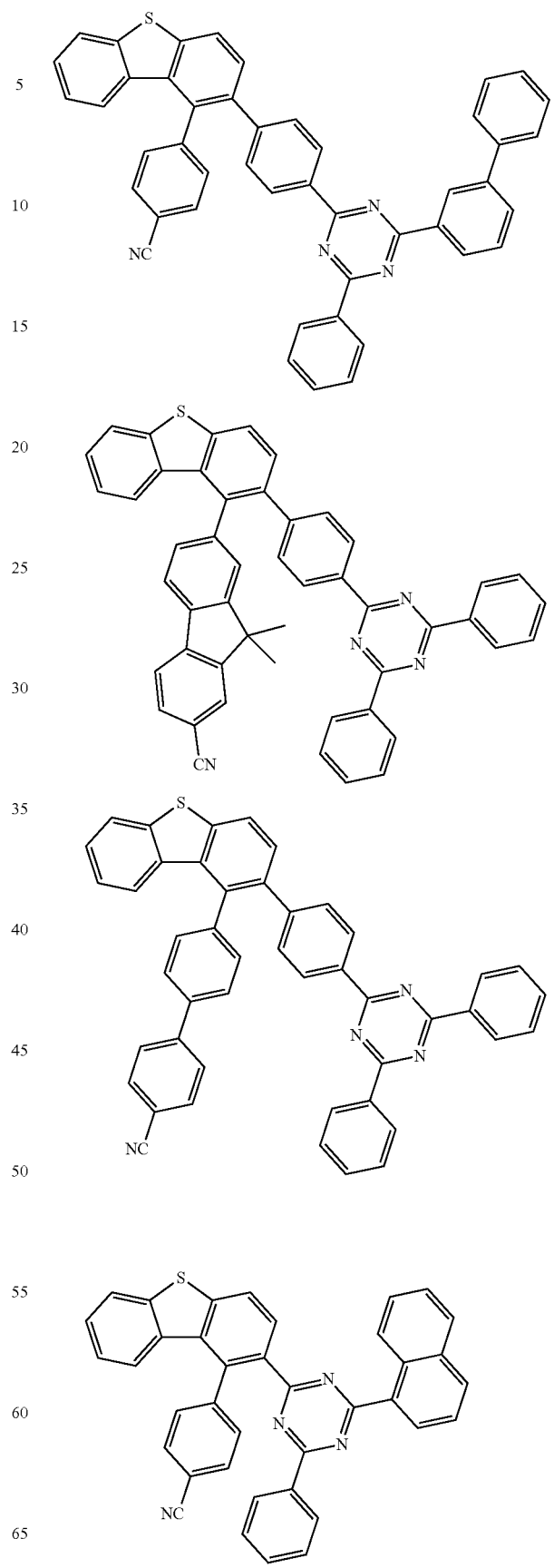

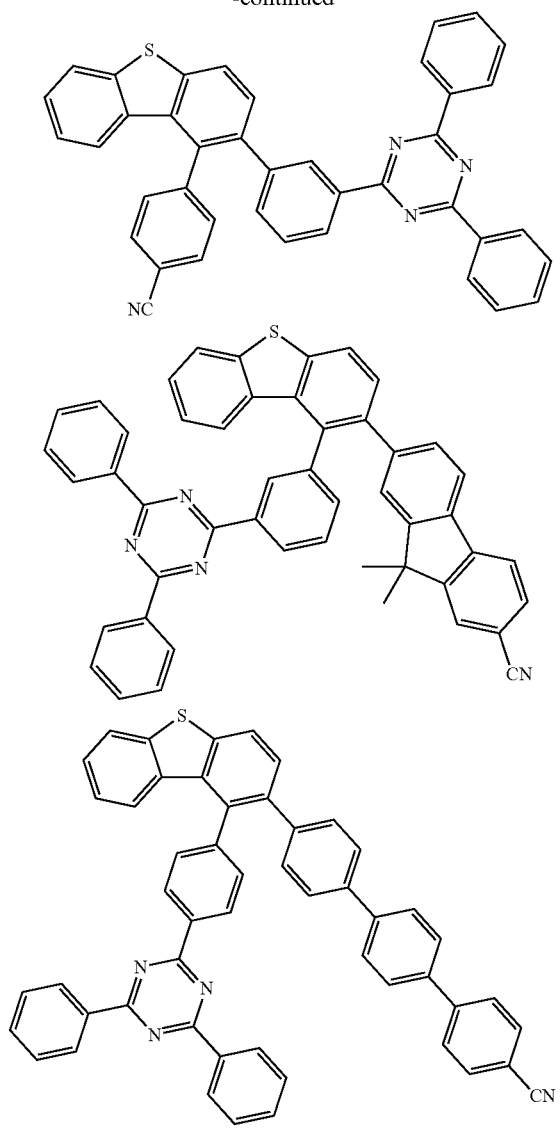
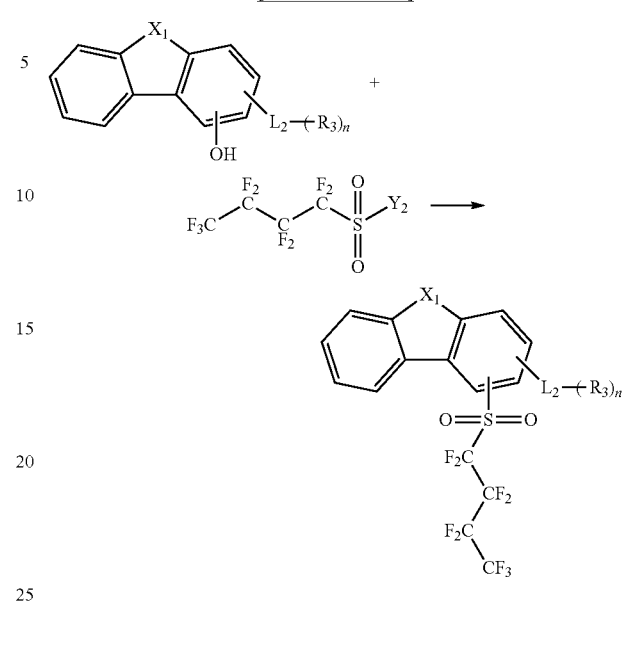
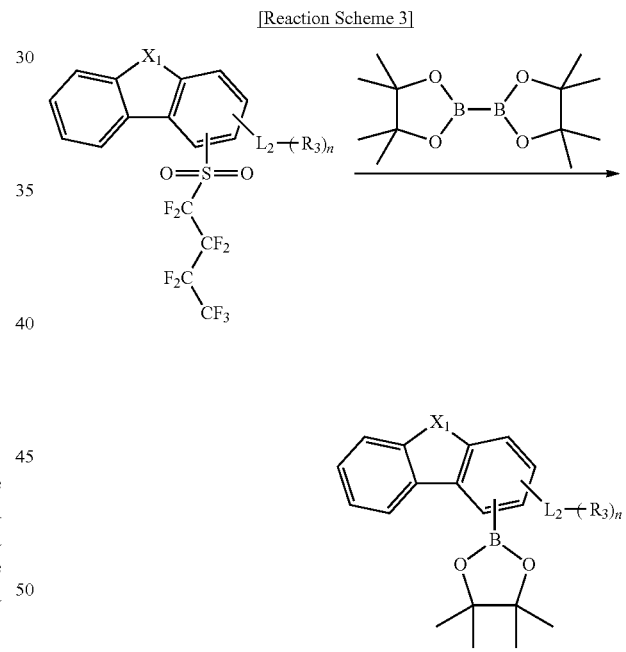
The compound represented by the Formula 1 can be prepared by sequentially performing the following Reaction Scheme 1, Reaction Scheme 2, Reaction Scheme 3, and Reaction Scheme 4. The above preparation method can be further specified in the preparation example to be described later.
[Reaction Scheme 1]
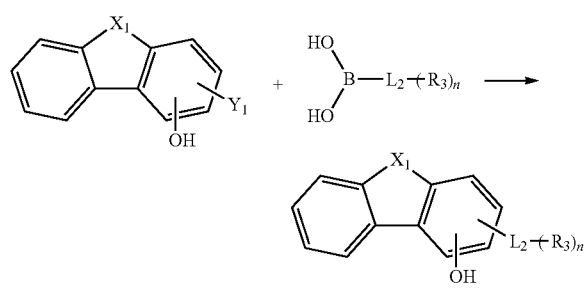
[Reaction Scheme 4]
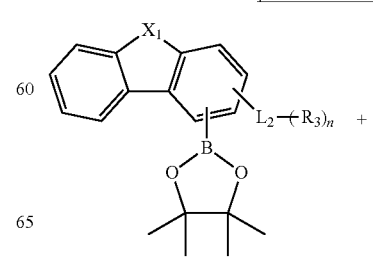

-continued

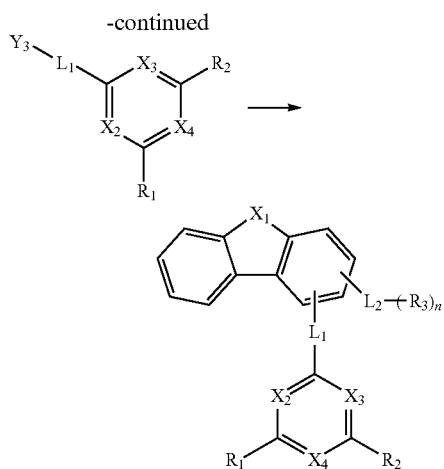

in Reaction Schemes 1 to 4, $X_1$, $X_2$, $X_3$, $X_4$, $L_1$, $L_2$, $R_1$, $R_2$, $R_3$ and n are as defined above, and $Y_1$, $Y_2$, and $Y_3$ are halogen.

In addition, the present disclosure provides an organic light emitting device comprising the compound represented by Formula 1. In one example, the present disclosure provides an organic light emitting device comprising a first electrode; a second electrode provided to face the first electrode; and at least one layer of organic material layers provided between the first electrode and the second electrode, wherein the at least one layer of the organic material layers includes a compound represented by Formula 1.

The organic material layer of the organic light emitting device of the present disclosure may have a single layer structure, but it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a hole injection layer, a hole transport layer, or a layer simultaneously performing hole injection and transport, wherein the hole injection layer, the hole transport layer, and the layer simultaneously performing hole injection and transport include a compound represented by Formula 1.

Further, the organic material layer may include a light emitting layer, wherein the light emitting layer includes a compound represented by Formula 1.

Further, the organic material layer may include an electron transport layer or an electron injection layer, wherein the electron transport layer or the electron injection layer include a compound represented by Formula 1.

Further, the electron transport layer, the electron injection layer and the layer simultaneously performing an electron injection and an electron transport include a compound represented by Formula 1. In particular, the compound represented by Formula I according to the present disclosure has excellent thermal stability and has a deep HOMO level of 6.0 eV or more, high triplet energy (ET), and hole stability. Further, when the compound represented by Formula 1 is used for an organic layer capable of performing electron injection and electron transport at the same time, an n-type dopant used in the art can be mixed and used.

Further, the organic material layer may include a light emitting layer or an electron transport layer, wherein the electron transport layer may include a compound represented by Formula 1.

Further, the organic light emitting device according to the present disclosure may be a normal type organic light emitting device in which an anode, at least one organic material layer, and a cathode are sequentially stacked on a substrate. Further, the organic light emitting device according to the present disclosure may be an inverted type organic light emitting device in which a cathode, at least one organic material layer and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound represented by Formula 1 may be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound represented by Formula 1 may be included in at least one layer of the hole injection layer, the hole transport layer, the light emitting layer and the electron transport layer.

The organic light emitting device according to the present disclosure may be manufactured by materials and methods known in the art, except that at least one layer of the organic material layers includes the compound represented by Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming an organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound represented by Formula 1 may be formed into an organic layer by a solution coating method as well as a vacuum deposition method at the time of manufacturing an organic light emitting element. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or SNO2:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability of transporting the holes, a hole injecting effect in the anode and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples include 8-hydroxy-quinoline aluminum complex ($Alq_3$), carbazole-based compounds; dimerized styryl compounds; BAlq; 10-hydroxybenzoquinoline-metal compounds; benzoxazole, benzothiazole and benzimidazole-based compounds; poly(p-phenylenevinylene)(PPV)-based polymers; spiro compounds; polyfluorene, rubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including $Alq_3$; an organic radical compound; a hydroxyflavone-metal complex, and the like, but are not limited thereto. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and its derivative, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8- quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound represented by Formula 1 may be included in an organic solar cell or an organic transistor in addition to an organic light emitting device.

The preparation of the compound represented by Formula 1 and the organic light emitting device comprising the same will be described in detail in the following examples. However, these examples are presented for illustrative purposes only, and the scope of the present disclosure is not limited thereto.

Example 1 (E1)

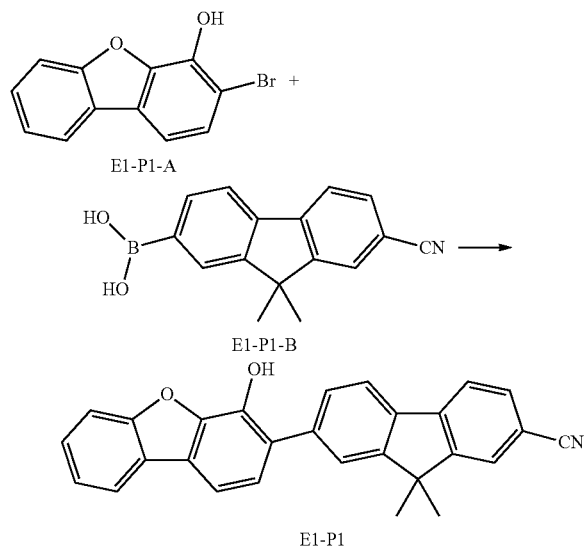

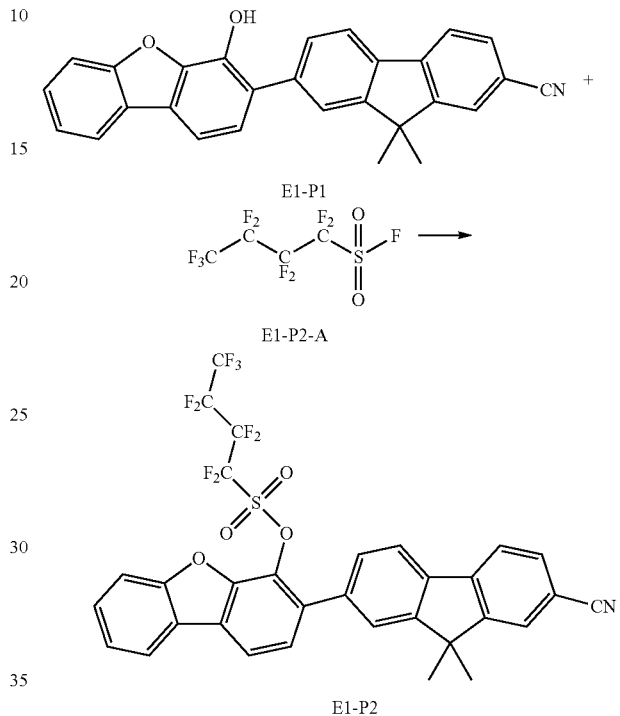

After a compound represented by Formula E1-P1-A (10.0 g, 38.0 mmol) and a compound represented by Formula E1-P1-B (10.0 g, 38.0 mmol) were completely dissolved in THF (100 mL), potassium carbonate (15.8 g, 114.0 mmol) was dissolved in 60 mL water and added thereto. Tetrakis triphenylphosphine palladium (1.3 g, 1.14 mmol) was added thereto, and then the mixture was heated and stirred for 8 hours. After the temperature was lowered to room temperature and the reaction was terminated, the potassium carbonate solution was removed and a white solid was filtered. The filtered white solid was washed twice with THF and ethyl acetate each time to prepare a compound represented by the Formula E1-P1 (13.5 g, yield 89%).

MS[M+H]$^+$=402

After a compound represented by Formula E1-P1 (13.5 g, 33.6 mmol) was completely dissolved in acetonitrile (130 mL), potassium carbonate (13.9 g, 100.9 mmol) was dissolved in 55 mL water and added thereto. A compound represented by the Formula E1-P2-A (10.2 g, 33.6 mmol) was added dropwise to the reaction solution. After termination of the reaction, the potassium carbonate solution was removed and a white solid was filtered. The filtered white solid was washed twice with ethanol and water each time to prepare a compound represented by the Formula E1-P2 (20.9 g, yield 91%).

MS[M+H]$^+$=684

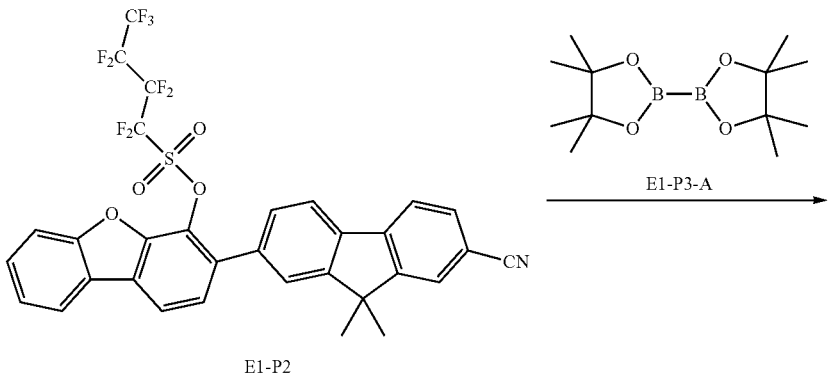

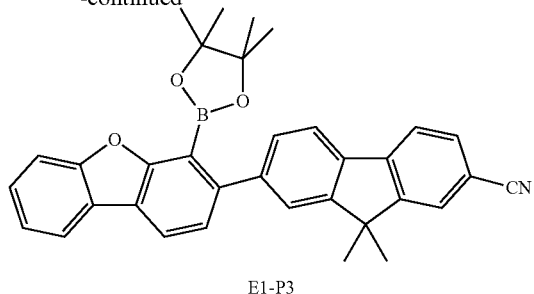

E1-P3

After a compound represented by the Formula E1-P2 (20.0 g, 29.3 mmol) and a compound represented by Formula E1-P3-A (7.5 g, 29.3 mmol) were completely dissolved in dioxane (200 mL), potassium acetate (8.6 g, 87.8 mmol) was added thereto, and then the mixture was heated and stirred. After the temperature was lowered to room temperature and the reaction was terminated, the potassium carbonate solution was removed and filtered to remove potassium carbonate. The white solid was washed twice with ethanol each time to prepare the compound represented by the Formula E1-P3 (12.7 g, yield 85%).

MS [M+H]$^+$=512

After a compound represented by Formula E1-P3 (12.0 g, 23.5 mmol) and a compound represented by Formula E1-A (6.3 g, 23.5 mmol) were completely dissolved in THF (120 mL), potassium carbonate (9.7 g, 70.4 mmol) was dissolved in 40 mL water and added thereto. Tetrakis triphenylphosphine palladium (0.8 g, 0.74 mmol) was added thereto, and then the mixture was heated and stirred for 8 hours. After the temperature was lowered to room temperature and the reaction was terminated, the potassium carbonate solution was removed and a white solid was filtered. The filtered white solid was washed twice with THF and ethyl acetate each time to prepare a compound represented by the Formula E1 (11.1 g, yield 77%).

MS[M+H]$^+$=617

Example 2 (E2)

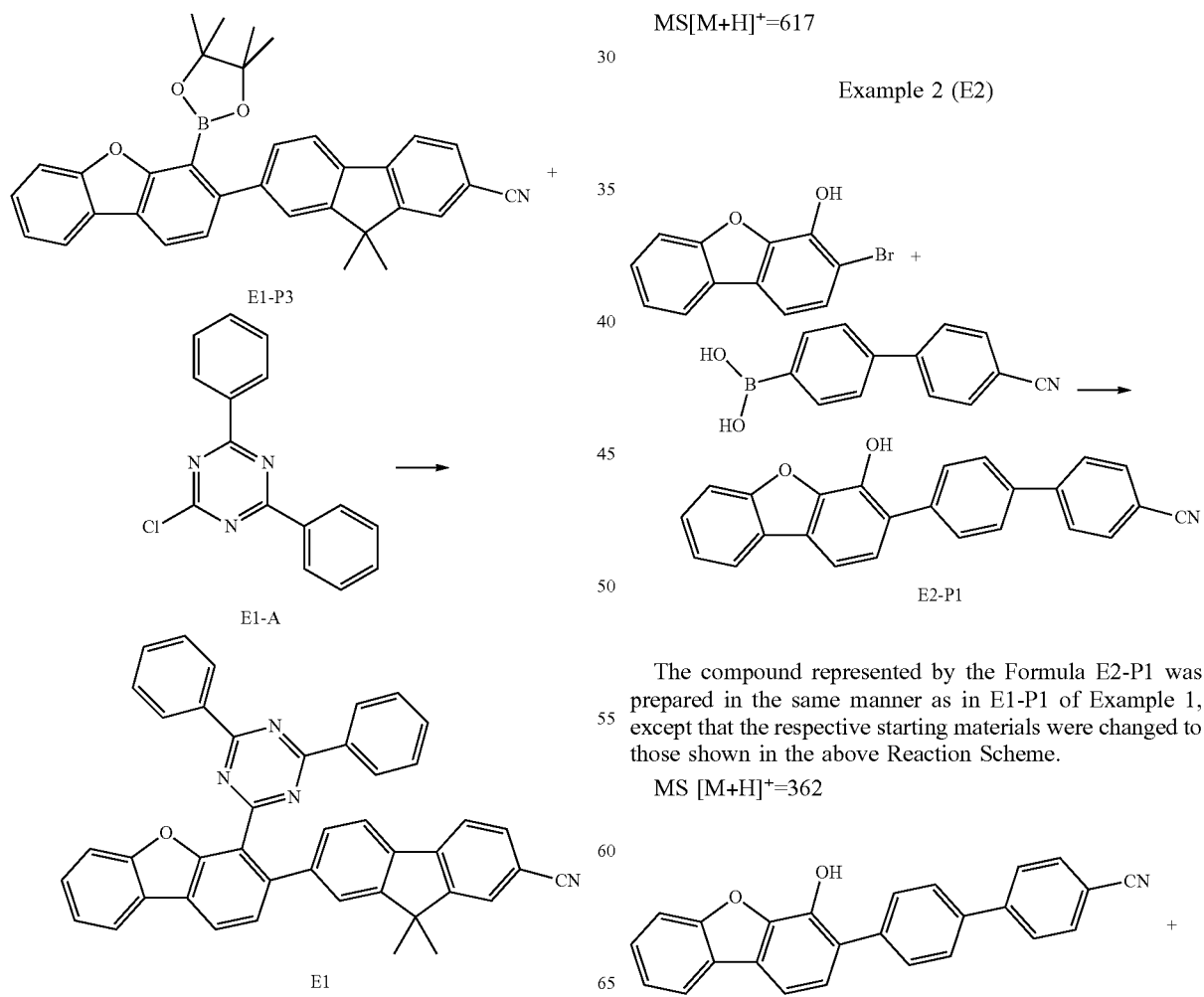

The compound represented by the Formula E2-P1 was prepared in the same manner as in E1-P1 of Example 1, except that the respective starting materials were changed to those shown in the above Reaction Scheme.

MS [M+H]$^+$=362

-continued

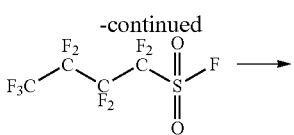

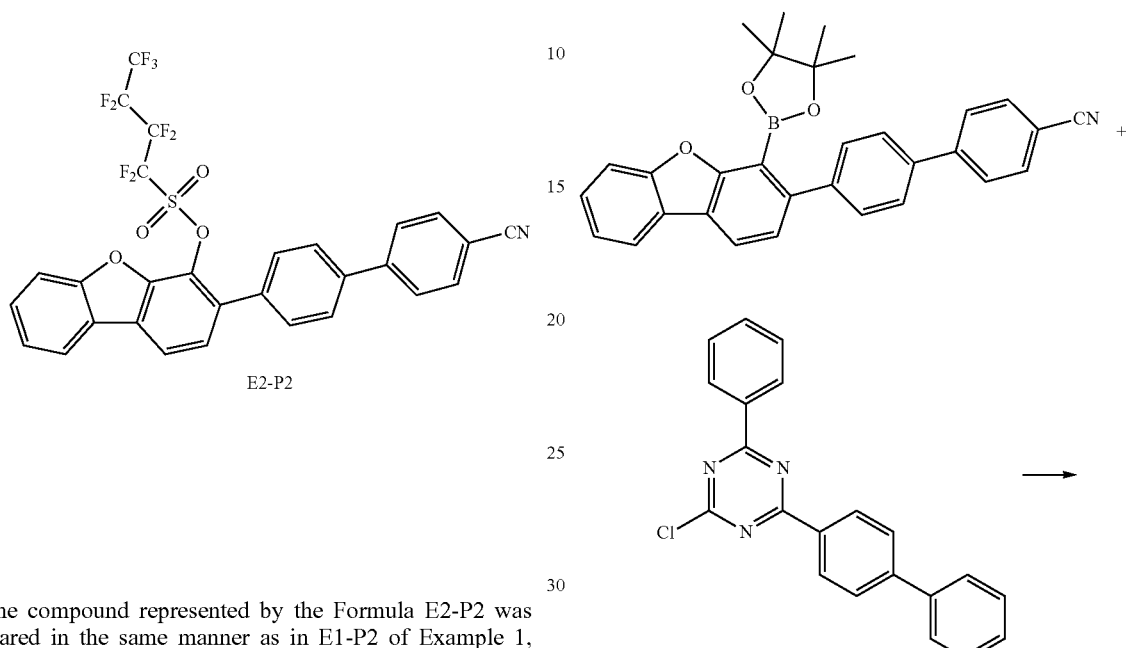

E2-P2

The compound represented by the Formula E2-P2 was prepared in the same manner as in E1-P2 of Example 1, except that the respective starting materials were changed to those shown in the above Reaction Scheme.
MS [M+H]⁺=644

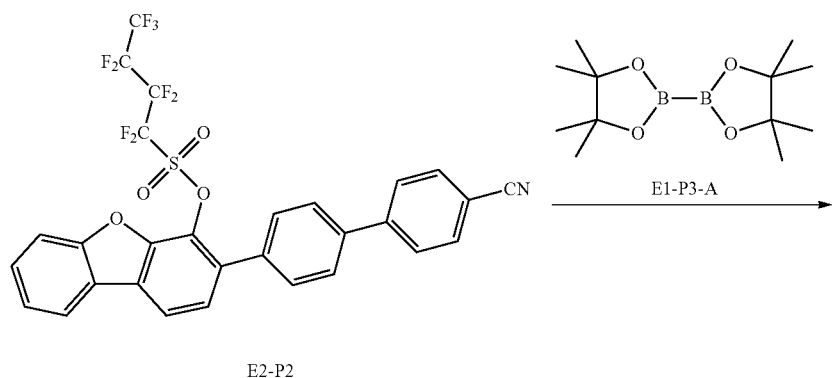

E2-P2

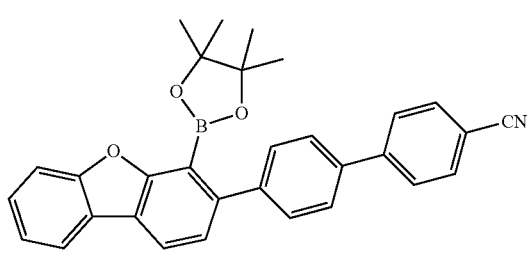

E2-P3

The compound represented by the Formula E2-P3 was prepared in the same manner as in E1-P3 of Example 1, except that the respective starting materials were changed to those shown in the above Reaction Scheme.
MS [M+H]⁺=472

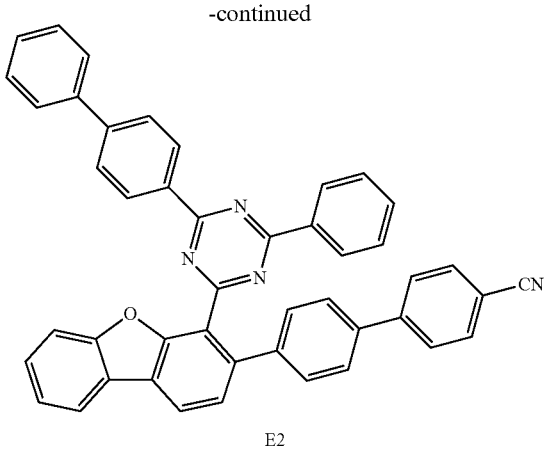

E2

The compound represented by the Formula E2 was prepared in the same manner as in E1 of Example 1, except that the respective starting materials were changed to those shown in the above Reaction Scheme.

MS [M+H]⁺=653

Example 3 (E3)

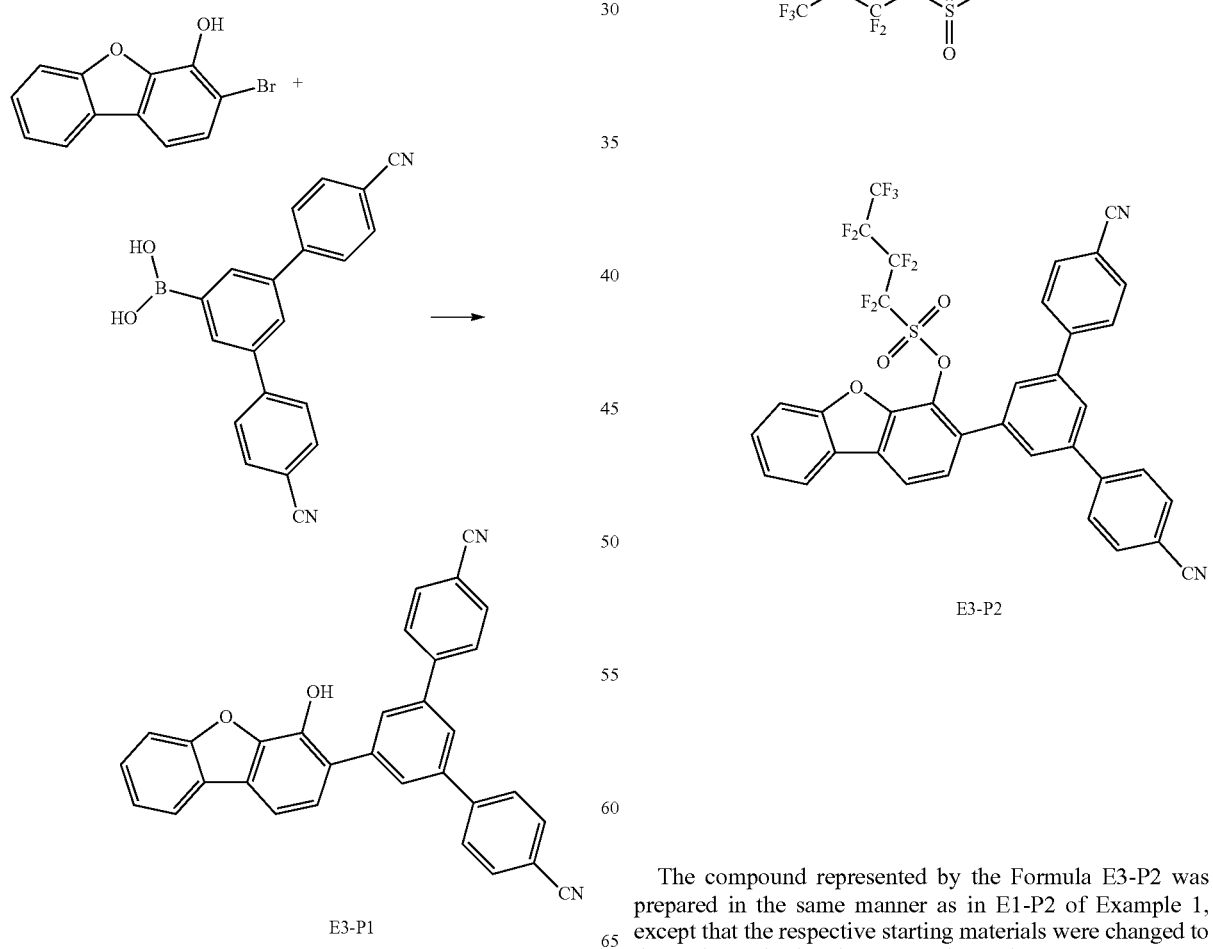

E3-P1

The compound represented by the Formula E3-P1 was prepared in the same manner as in E1-P1 of Example 1, except that the respective starting materials were changed to those shown in the above Reaction Scheme.

MS [M+H]⁺=463

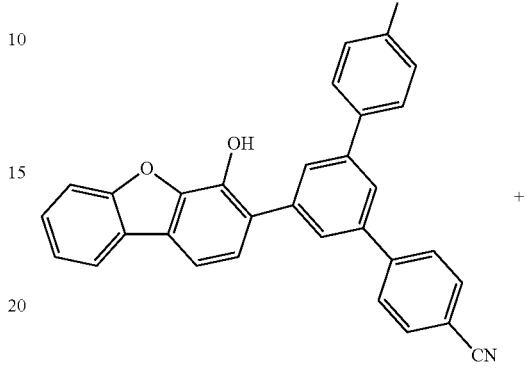

E3-P2

The compound represented by the Formula E3-P2 was prepared in the same manner as in E1-P2 of Example 1, except that the respective starting materials were changed to those shown in the above Reaction Scheme.

MS [M+H]⁺=745

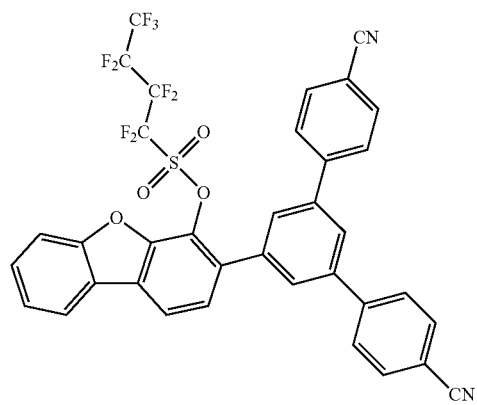
E3-P2
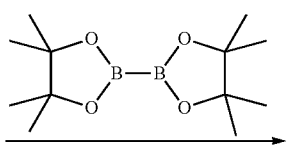
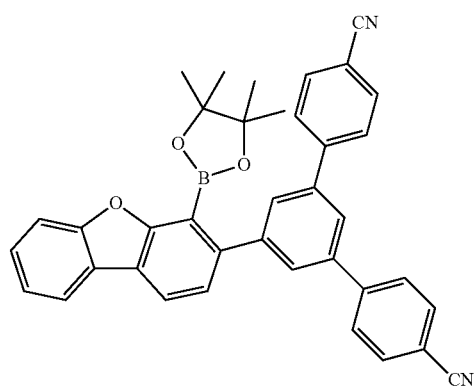
E3-P3
The compound represented by the Formula E3-P3 was prepared in the same manner as in E1-P3 of Example 1, except that the respective starting materials were changed to those shown in the above Reaction Scheme.
MS [M+H]⁺=573
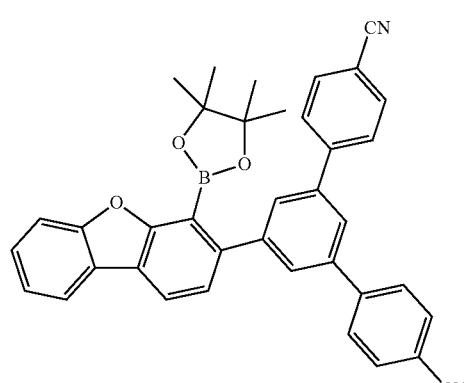
E3-P3
+
-continued
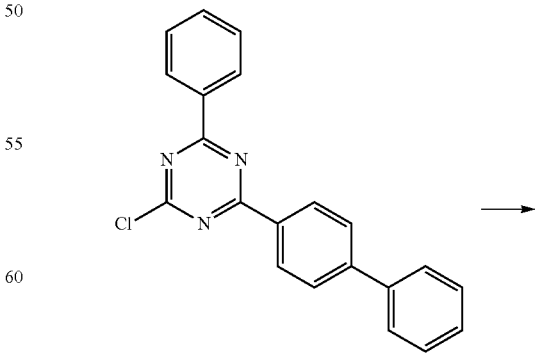

67
-continued

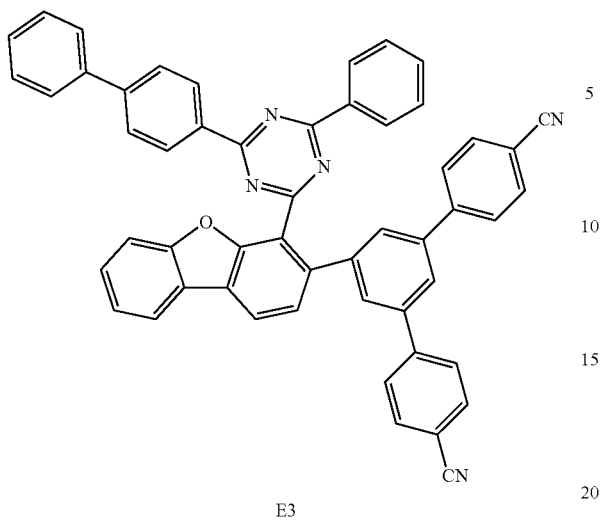

E3

The compound represented by the Formula E3 was prepared in the same manner as in E1 of Example 1, except that the respective starting materials were changed to those shown in the above Reaction Scheme.

MS $[M+H]^+$=754

Example 4 (E4)

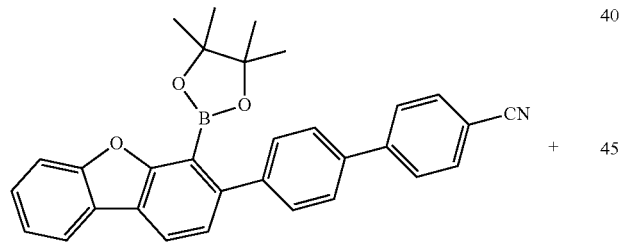

68
-continued

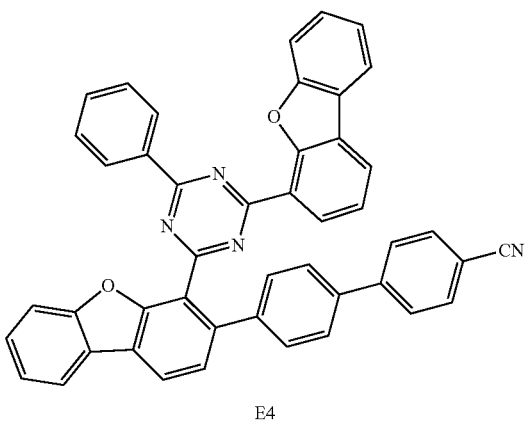

E4

The compound represented by the Formula E4 was prepared in the same manner as in E1 of Example 1, except that the respective starting materials were changed to those shown in the above Reaction Scheme.

MS $[M+H]^+$=667

Example 5 (E5)

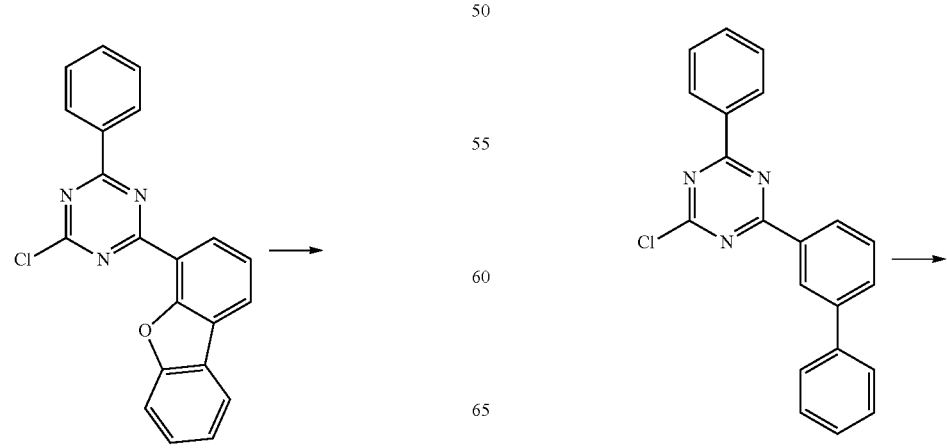

69
-continued

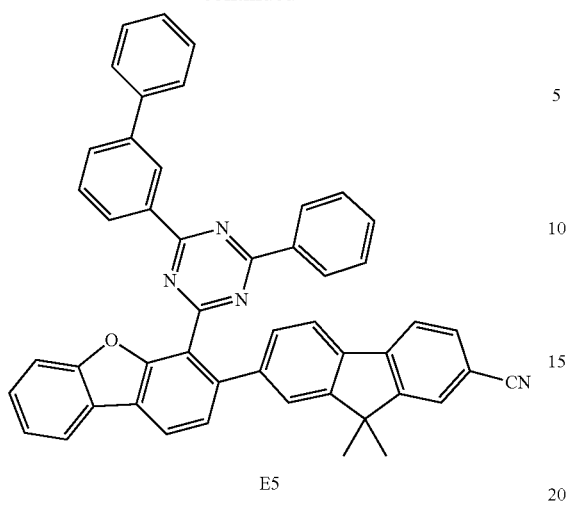

E5

The compound represented by the Formula E5 was prepared in the same manner as in E1 of Example 1, except that the respective starting materials were changed to those shown in the above Reaction Scheme.

MS [M+H]$^+$=693

Example 6 (E6)

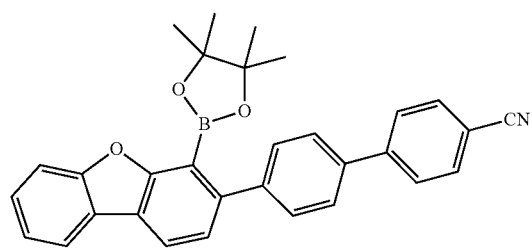

70
-continued

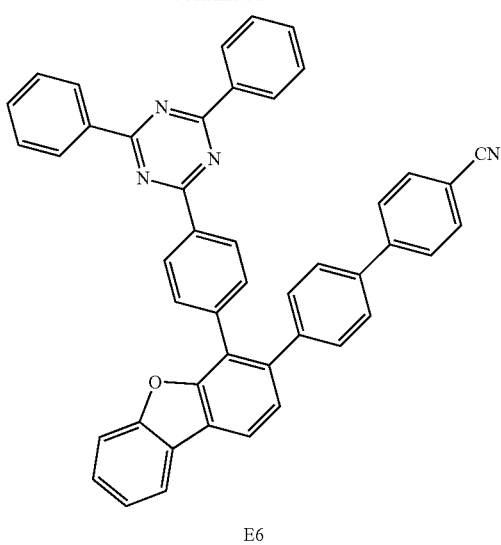

E6

The compound represented by the Formula E6 was prepared in the same manner as in E1 of Example 1, except that the respective starting materials were changed to those shown in the above Reaction Scheme.

MS [M+H]$^+$=653

Example 7 (E7)

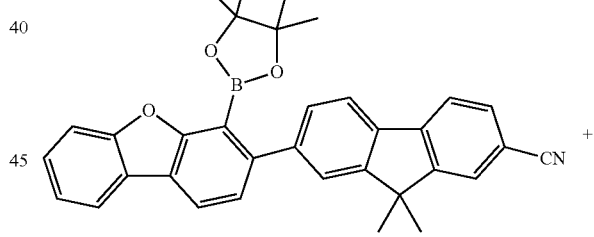

+

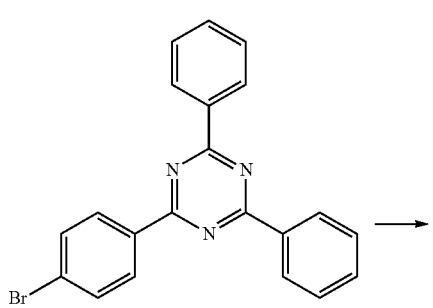

+

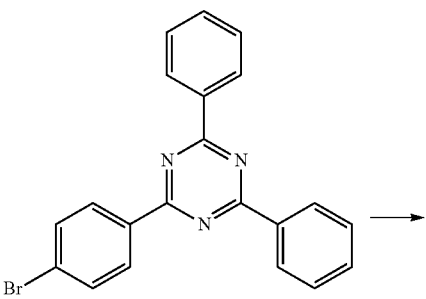

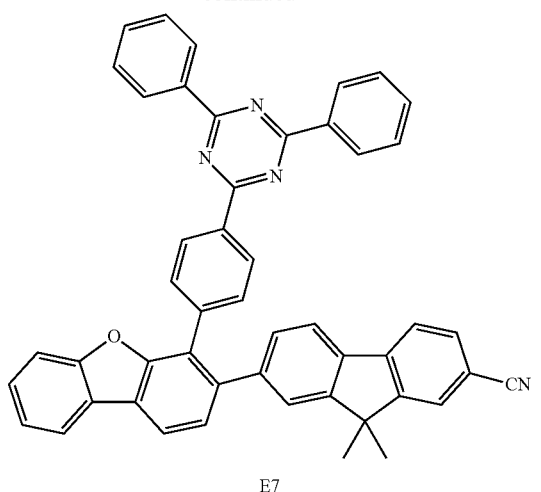

E7

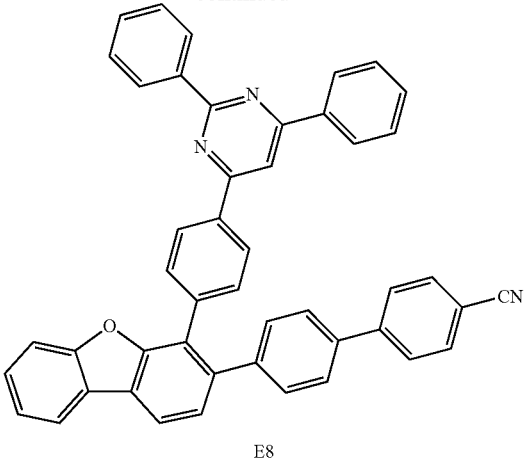

E8

The compound represented by the Formula E8 was prepared in the same manner as in E1 of Example 1, except that the respective starting materials were changed to those shown in the above Reaction Scheme.

MS [M+H]$^+$=652

Example 9 (E9)

The compound represented by the Formula E7 was prepared in the same manner as in E1 of Example 1, except that the respective starting materials were changed to those shown in the above Reaction Scheme.

MS [M+H]$^+$=693

Example 8 (E8)

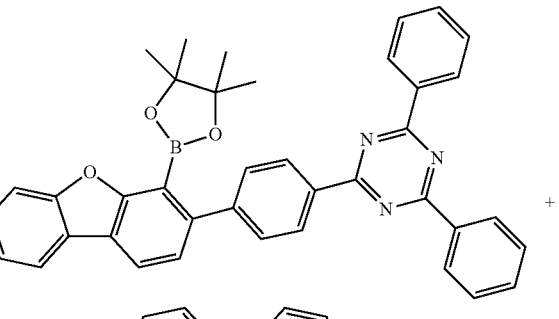

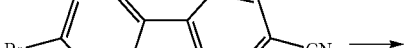

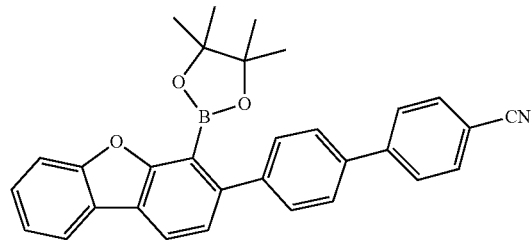

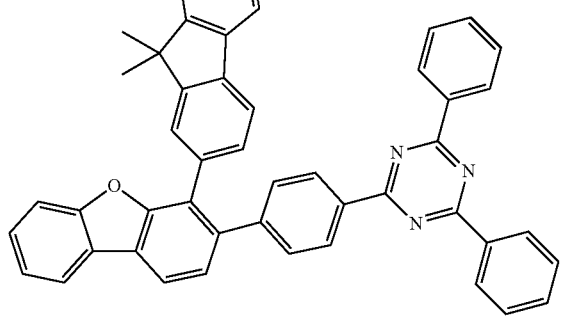

E9

The compound represented by the Formula E9 was prepared in the same manner as in E1 of Example 1, except that the respective starting materials were changed to those shown in the above Reaction Scheme.

MS [M+H]$^+$=693

Example 10 (E10)

Example 11 (E11)

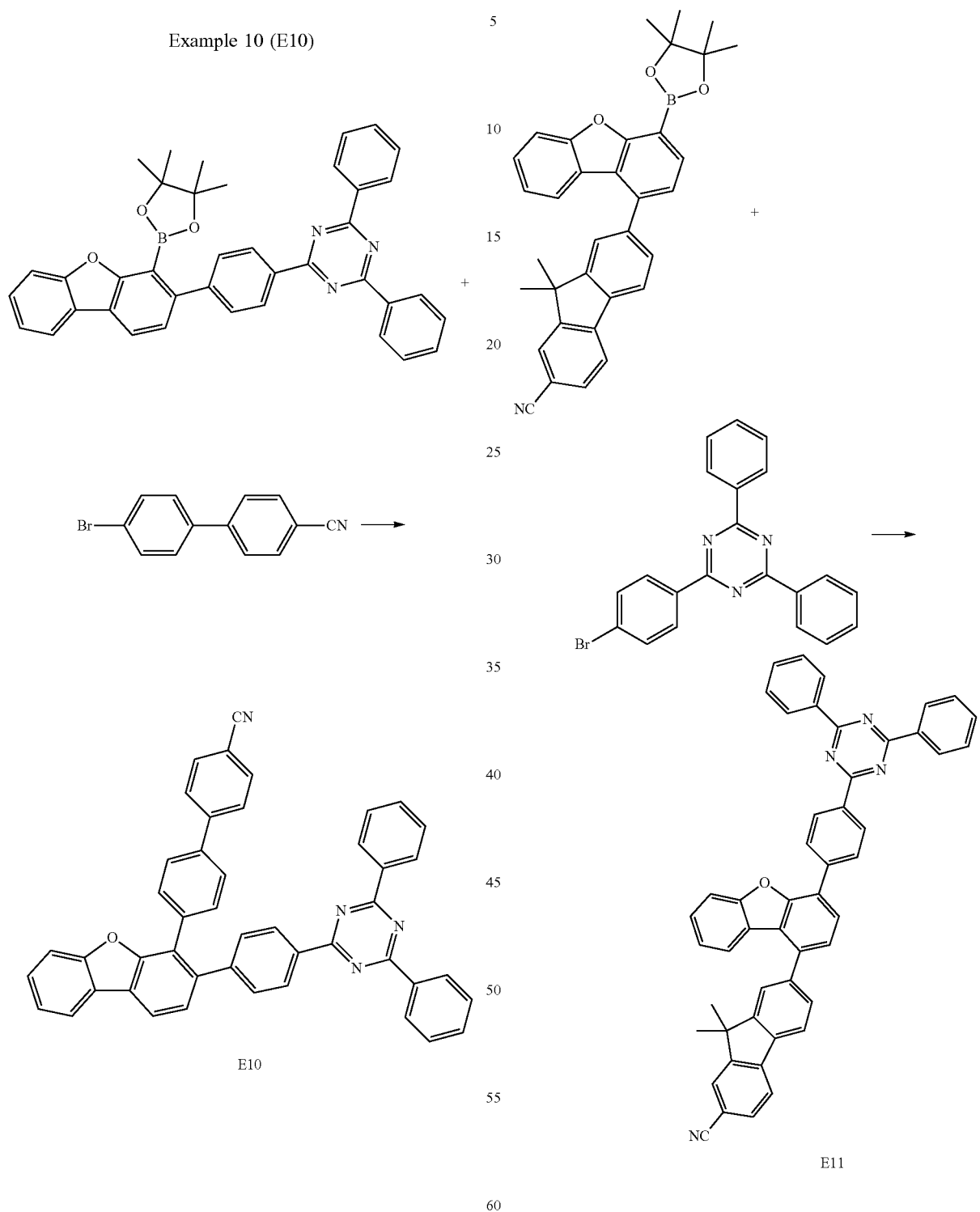

E10

E11

The compound represented by the Formula E10 was prepared in the same manner as in E1 of Example 1, except that the respective starting materials were changed to those shown in the above Reaction Scheme.

MS [M+H]$^+$=653

The compound represented by the Formula E11 was prepared in the same manner as in E1 of Example 1, except that the respective starting materials were changed to those shown in the above Reaction Scheme.

MS [M+H]$^+$=693

Example 12 (E12)

Example 13 (E13)

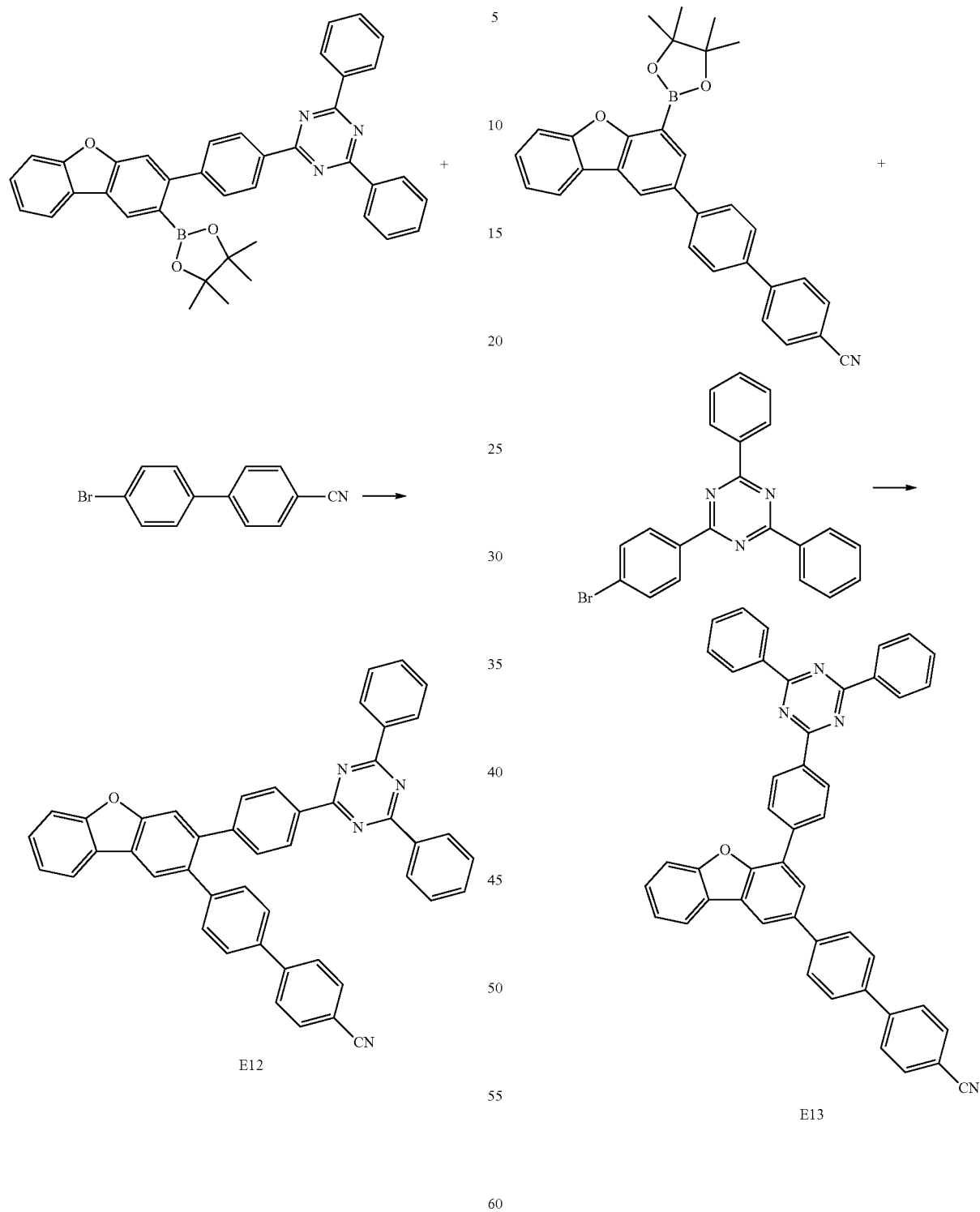

The compound represented by the Formula E12 was prepared in the same manner as in E1 of Example 1, except that the respective starting materials were changed to those shown in the above Reaction Scheme.

MS [M+H]$^+$=653

The compound represented by the Formula E13 was prepared in the same manner as in E1 of Example 1, except that the respective starting materials were changed to those shown in the above Reaction Scheme.

MS [M+H]$^+$=653

Example 14 (E14)

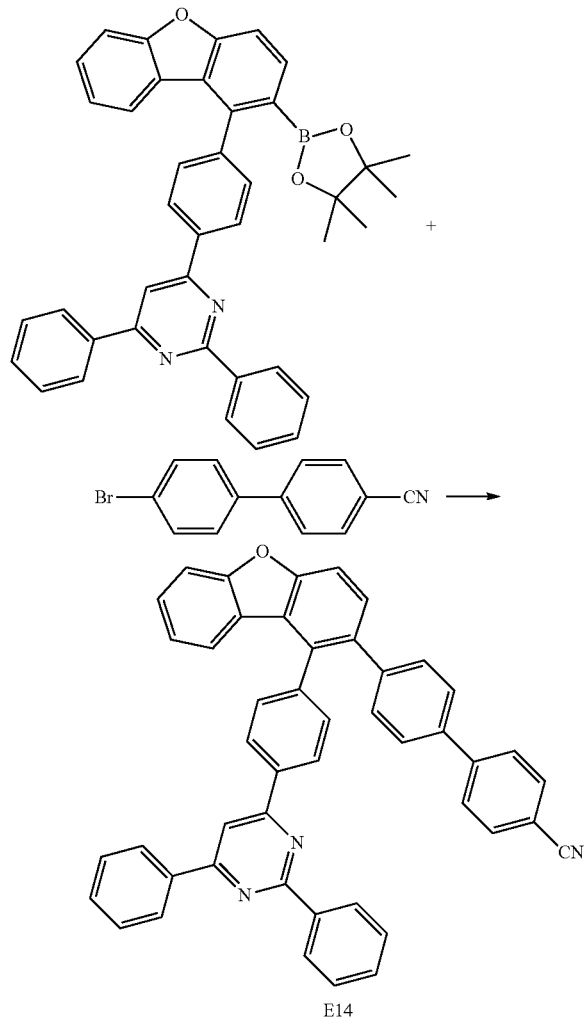

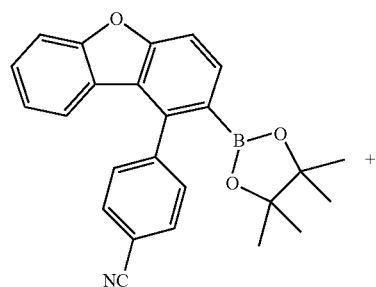

E14

The compound represented by the Formula E14 was prepared in the same manner as in E1 of Example 1, except that the respective starting materials were changed to those shown in the above Reaction Scheme.

MS [M+H]$^+$=652

Example 15 (E15)

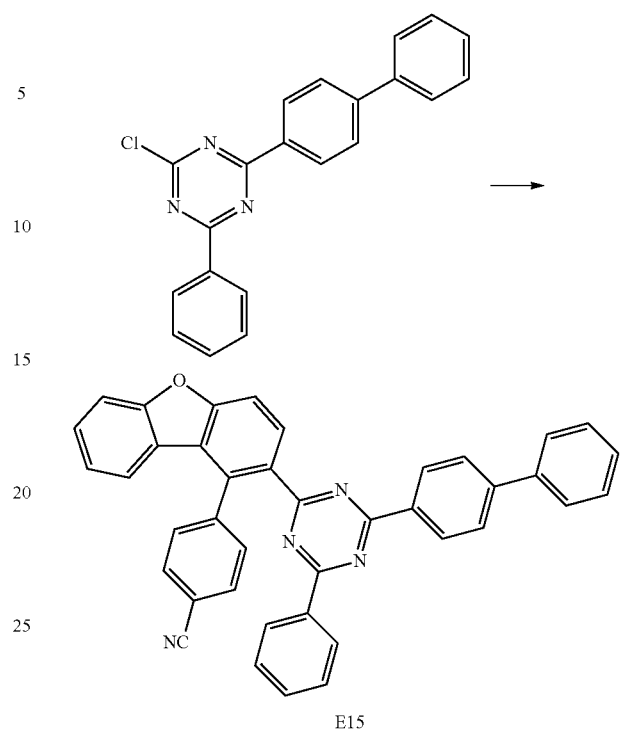

E15

The compound represented by the Formula E15 was prepared in the same manner as in E1 of Example 1, except that the respective starting materials were changed to those shown in the above Reaction Scheme.

MS [M+H]$^+$=577

Example 16 (E16)

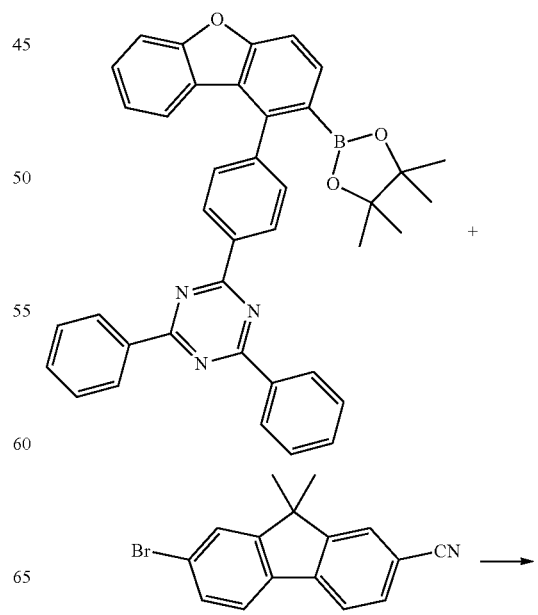

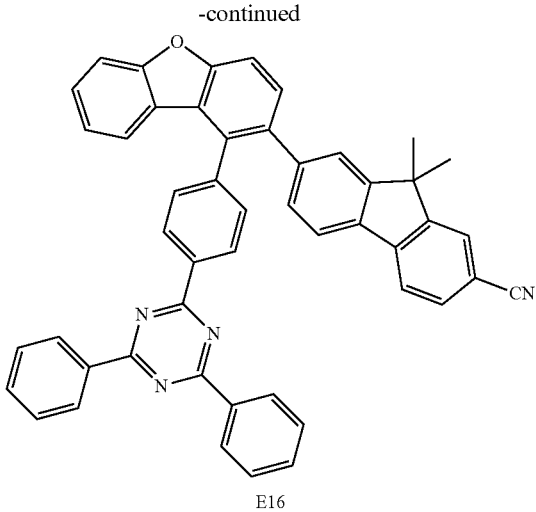

E16

The compound represented by the Formula E16 was prepared in the same manner as in E1 of Example 1, except that the respective starting materials were changed to those shown in the above Reaction Scheme.

MS [M+H]⁺=693

Example 17 (E17)

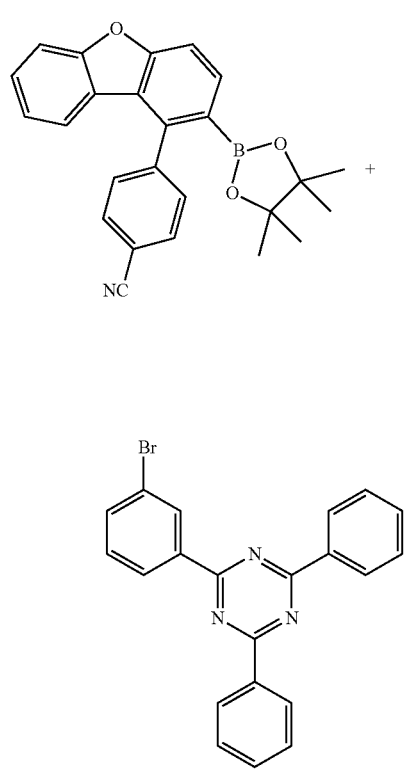

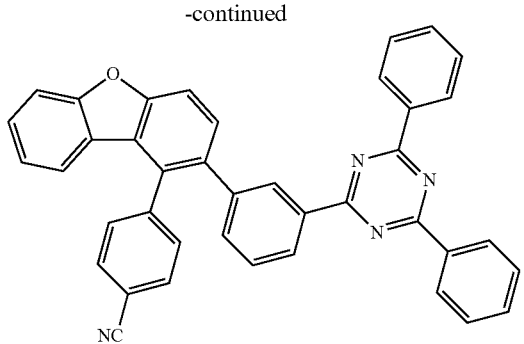

E17

The compound represented by the Formula E17 was prepared in the same manner as in E1 of Example 1, except that the respective starting materials were changed to those shown in the above Reaction Scheme.

MS [M+H]⁺=577

Example 18 (E18)

E18

The compound represented by the Formula E18 was prepared in the same manner as in E1 of Example 1, except that the respective starting materials were changed to those shown in the above Reaction Scheme.

MS [M+H]$^+$=567

Example 19 (E19)

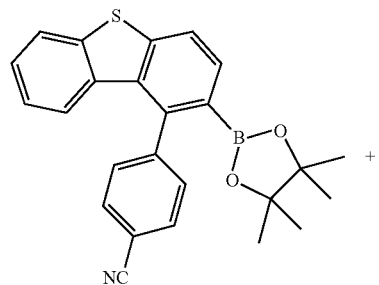

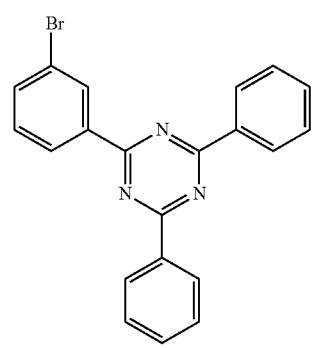

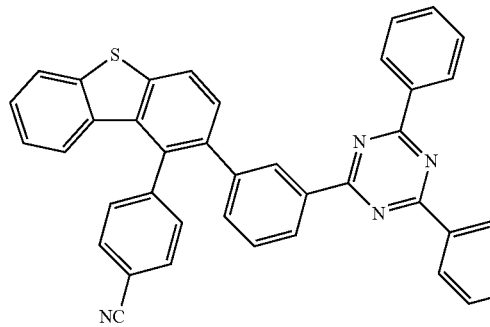

E19

Example 20 (E20)

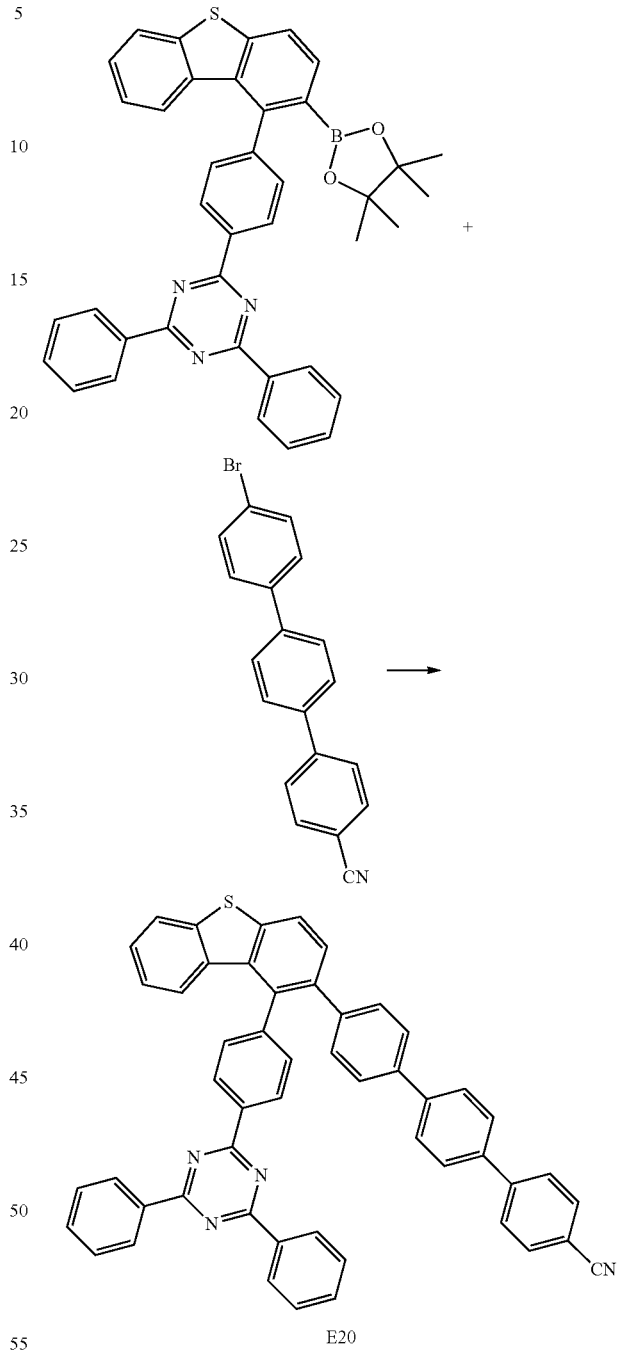

E20

The compound represented by the Formula E19 was prepared in the same manner as in E1 of Example 1, except that the respective starting materials were changed to those shown in the above Reaction Scheme.

MS [M+H]$^+$=593

The compound represented by the Formula E20 was prepared in the same manner as in E1 of Example 1, except that the respective starting materials were changed to those shown in the above Reaction Scheme.

MS [M+H]$^+$=745

Example 21 (E21)

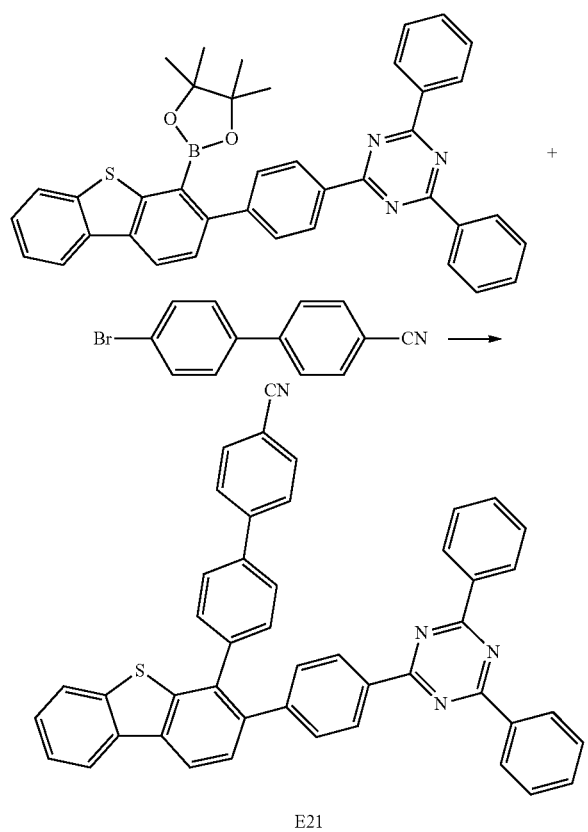

E21

The compound represented by the Formula E21 was prepared in the same manner as in E1 of Example 1, except that the respective starting materials were changed to those shown in the above Reaction Scheme.

MS [M+H]$^+$=669

Example 22 (E22)

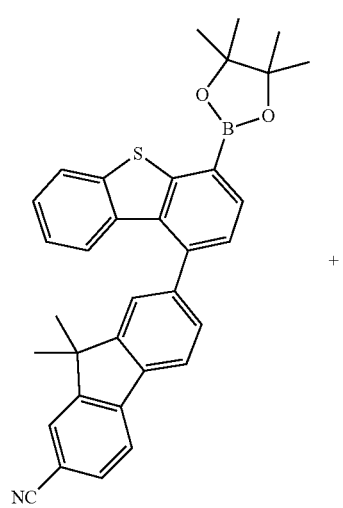

E22

The compound represented by the Formula E22 was prepared in the same manner as in E1 of Example 1, except that the respective starting materials were changed to those shown in the above Reaction Scheme.

MS [M+H]$^+$=709

Experimental Example 1

A glass substrate on which a thin film of ITO (indium tin oxide) was coated in a thickness of 1,000 Å was put into distilled water containing the detergent dissolved therein and washed by the ultrasonic wave. The used detergent was a product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound HI-A below was thermally vacuum-deposited in a thickness of 600 Å to form a hole injection layer. A compound HAT (50 Å) below and a compound HT-A (600 Å) below were sequentially vacuum-deposited on the hole injection layer to form a hole transport.

Then, a compound BH below and a compound BD below were vacuum-deposited at a weight ratio of 25:1 on the electron transport layer in a film thickness of 20 nm to form a light emitting layer.

The compound E1 of Example 1 and a compound LiQ below were vacuum-deposited at a weight ratio of 1:1 on the light emitting layer in a thickness of 350 Å to form an electron injection and transport layer. A lithium fluoride (LiF) in a thickness of 10 Å and aluminum in a thickness of 1,000 Å were sequentially deposited on the electron injection and transport layer to form a cathode.

In the above process, the vapor deposition rate of the organic material was maintained at 0.4 to 0.9 Å/sec, the vapor deposition rate of lithium fluoride of the cathode was maintained at 0.3 Å/sec, the vapor deposition rate of aluminum was maintained at 2 Å/sec, and the degree of vacuum during vapor deposition was maintained at $1\times10^{-7}$-$5\times10^{-5}$ torr to manufacture an organic light emitting device.

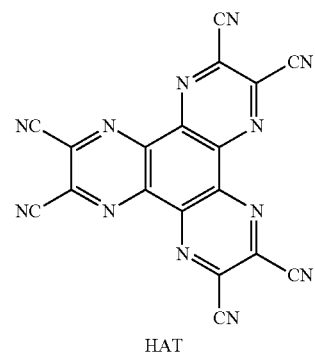

HAT

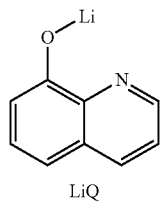

LiQ

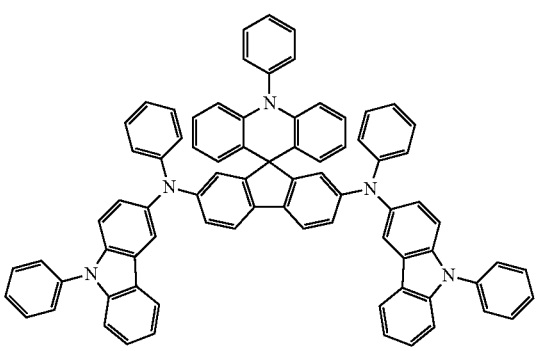

HI-A

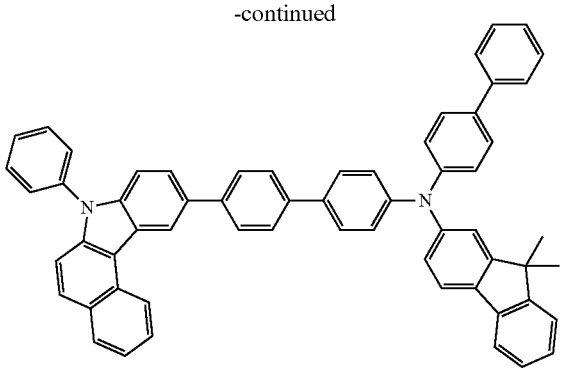

HT-A

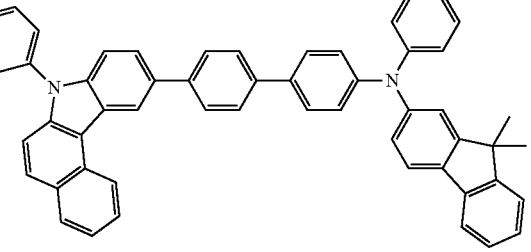
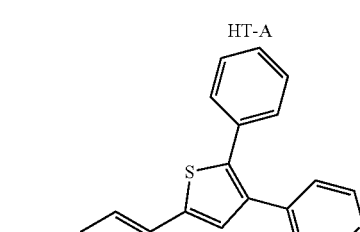
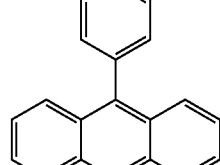
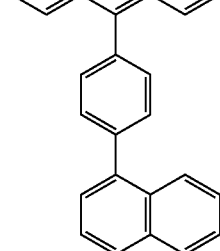
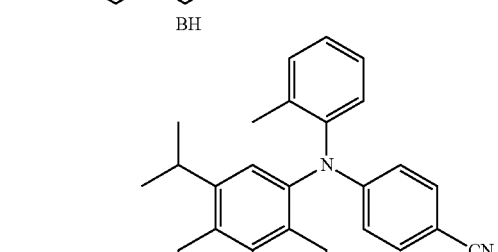

BH

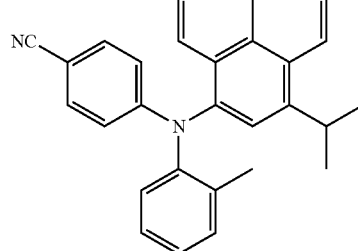
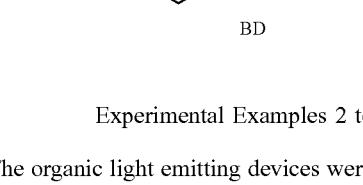

BD

Experimental Examples 2 to 22

The organic light emitting devices were manufactured in the same manner as in Experimental Example 1, except that the compounds E2 to E22 of Examples 2 to 22 were used instead of the compound E1 of Example 1.

ET-A
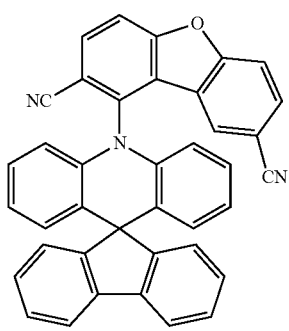
ET-B
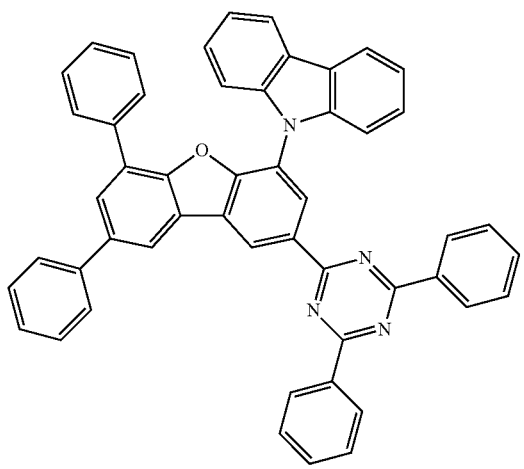
ET-C
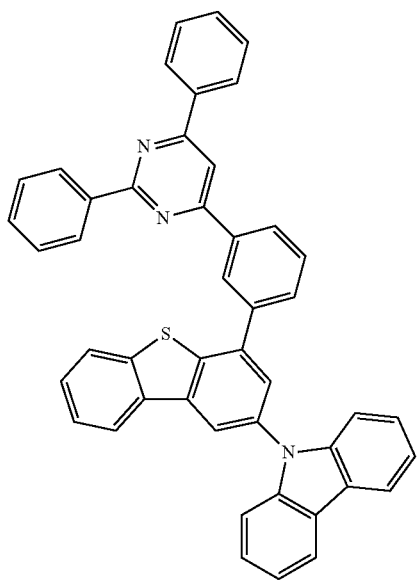
-continued
ET-D
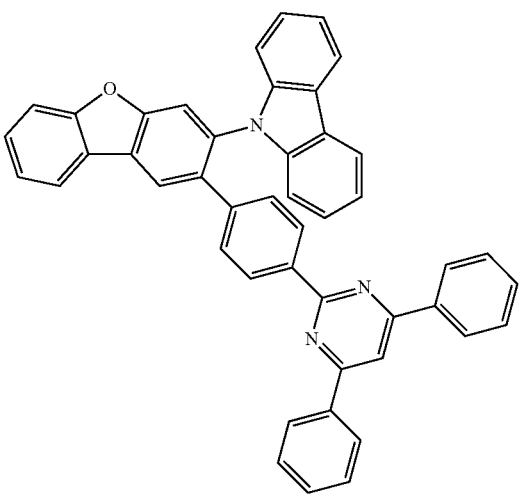
ET-E
ET-F
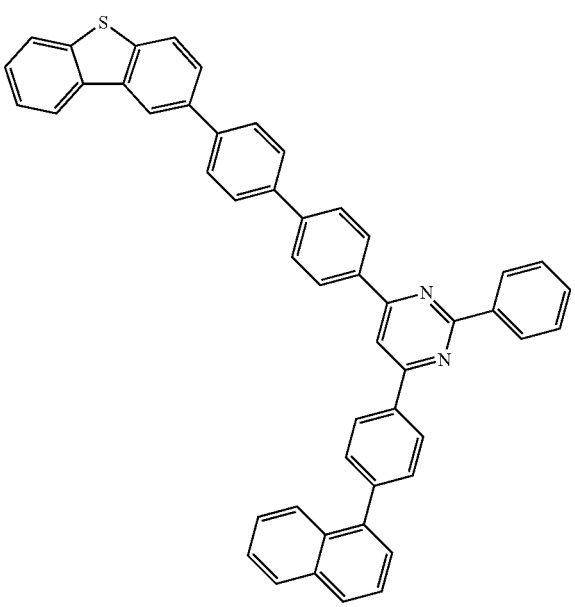

ET-G

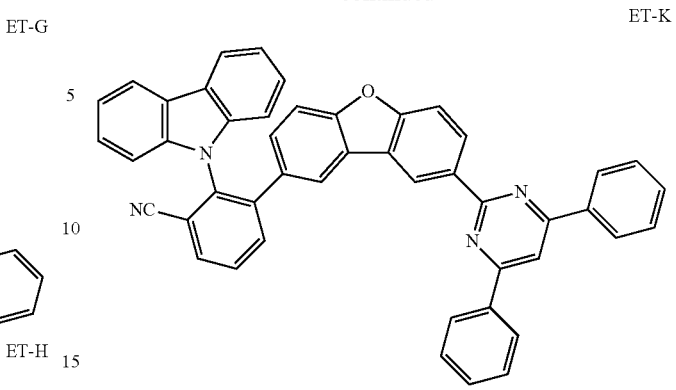

ET-K

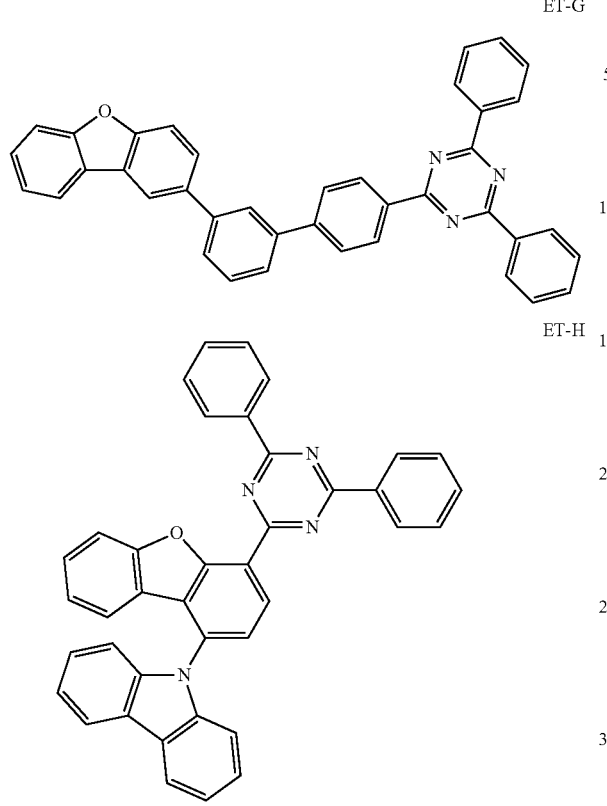

ET-H

ET-I

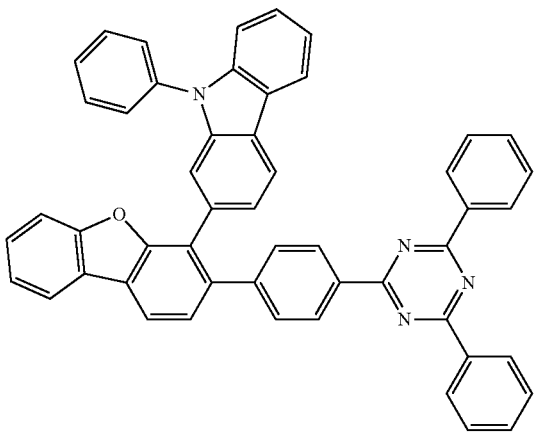

ET-J

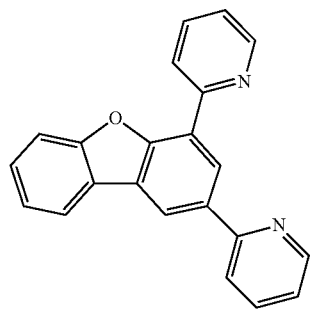

Comparative Examples 1-11

The organic light emitting devices were manufactured in the same manner as in Experimental Example 1, except that the above compounds ET-A to ET-K were used instead of the compound E1 of Example 1.

The driving voltage and light emitting efficiency were measured at the current density of 10 mA/cm² for the organic light emitting devices manufactured in the Examples and Comparative Examples, and the time (T90) at which the luminance became 90% relative to the initial luminance at the current density of 20 mA/cm² was measured. The above results are shown in Tables 1 and 2.

TABLE 1

| Class | Voltage (V@10 mA/cm²) | Efficiency (cd/A@10 mA/cm²) | Color coordinate (x, y) | Lifetime (h) T90 at 20 mA/cm² |
|---|---|---|---|---|
| Experimental Example 1(E1) | 4.47 | 5.01 | (0.142, 0.096) | 270 |
| Experimental Example 2(E2) | 4.50 | 4.95 | (0.142, 0.096) | 300 |
| Experimental Example 3(E3) | 4.66 | 4.80 | (0.142, 0.096) | 410 |
| Experimental Example 4(E4) | 4.51 | 4.94 | (0.142, 0.096) | 314 |
| Experimental Example 5(E5) | 4.45 | 5.05 | (0.142, 0.096) | 266 |
| Experimental Example 6(E6) | 4.40 | 5.10 | (0.142, 0.097) | 245 |
| Experimental Example 7(E7) | 4.39 | 5.08 | (0.142, 0.096) | 239 |
| Experimental Example 8(E8) | 4.39 | 5.11 | (0.142, 0.099) | 230 |
| Experimental Example 9(E9) | 4.41 | 5.09 | (0.142, 0.096) | 255 |
| Experimental Example 10(E10) | 4.43 | 5.06 | (0.142, 0.099) | 261 |
| Experimental Example 11(E11) | 4.42 | 5.13 | (0.142, 0.096) | 244 |
| Experimental Example 12(E12) | 4.33 | 5.08 | (0.142, 0.097) | 240 |
| Experimental Example 13(E13) | 4.48 | 5.03 | (0.142, 0.096) | 284 |
| Experimental Example 14(E14) | 4.37 | 5.11 | (0.142, 0.096) | 266 |
| Experimental Example 15(E15) | 4.47 | 4.99 | (0.142, 0.096) | 299 |
| Experimental Example 16(E16) | 4.40 | 5.15 | (0.142, 0.097) | 235 |
| Experimental Example 17(E17) | 4.33 | 5.20 | (0.142, 0.096) | 233 |
| Experimental Example 18(E18) | 4.47 | 5.00 | (0.142, 0.096) | 301 |

TABLE 1-continued

| Class | Voltage (V@10 mA/cm$^2$) | Efficiency (cd/A@10 mA/cm$^2$) | Color coordinate (x, y) | Lifetime (h) T90 at 20 mA/cm$^2$ |
|---|---|---|---|---|
| Experimental Example 19(E19) | 4.32 | 5.18 | (0.142, 0.096) | 231 |
| Experimental Example 20(E20) | 4.41 | 5.07 | (0.142, 0.095) | 287 |
| Experimental Example 21(E21) | 4.40 | 5.08 | (0.142, 0.099) | 255 |
| Experimental Example 22(E22) | 4.41 | 5.12 | (0.142, 0.096) | 260 |

TABLE 2

| Class | Voltage (V@10 mA/cm$^2$) | Efficiency (cd/A@10 mA/cm$^2$) | Color coordinate (x, y) | Lifetime (h) T90 at 20 mA/cm$^2$ |
|---|---|---|---|---|
| Comparative Example 1(ET-A) | 6.00 | 3.14 | (0.142, 0.096) | 170 |
| Comparative Example 2(ET-B) | 5.12 | 3.77 | (0.142, 0.096) | 142 |
| Comparative Example 3(ET-C) | 5.01 | 3.83 | (0.142, 0.096) | 88 |
| Comparative Example 4(ET-D) | 5.16 | 3.83 | (0.142, 0.096) | 55 |
| Comparative Example 5(ET-E) | 5.07 | 3.80 | (0.142, 0.096) | 74 |
| Comparative Example 6(ET-F) | 5.05 | 3.81 | (0.142, 0.096) | 73 |
| Comparative Example 7(ET-G) | 5.11 | 3.76 | (0.142, 0.097) | 80 |
| Comparative Example 8(ET-H) | 5.89 | 3.04 | (0.142, 0.097) | 180 |
| Comparative Example 9(ET-I) | 5.12 | 3.69 | (0.142, 0.096) | 91 |
| Comparative Example 10(ET-J) | 6.10 | 3.04 | (0.142, 0.099) | 20 |
| Comparative Example 11(ET-K) | 6.18 | 3.90 | (0.142, 0.096) | 19 |

As shown in Table 1, it was confirmed that the compound represented by Formula 1 according to the present disclosure can be used for an organic material layer capable of simultaneously performing electron injection and electron transport of the organic light-emitting device.

In addition, when comparing the Experimental Examples in Table 1 and the Comparative Experimental Examples 2, 3, 4, 8 and 9 in Table 2, it was confirmed that the compounds of Formula 1 according to the present disclosure were remarkably excellent in terms of driving voltage, efficiency, and lifetime of the organic light emitting device as compared with a compound in which a triazine (or pyrimidine) and a heteroaryl group different from the Formula 1 were substituted in dibenzofuran (or dibenzothiophene).

Further, when comparing the Experimental Examples in Table 1 and the Comparative Experimental Example 1 in Table 2, it was confirmed that the compounds of Formula 1 according to the present disclosure were remarkably excellent in terms of driving voltage, efficiency, and lifetime of the organic light emitting device as compared with a compound in which a cyano group and a heteroaryl group different from the Formula 1 were substituted in dibenzofuran (or dibenzothiophene).

Further, when comparing the Experimental Examples in Table 1 and the Comparative Experimental Examples 5, 6 and 7 in Table 2, it was confirmed that the compounds of Formula 1 according to the present disclosure were remarkably excellent in terms of driving voltage, efficiency, and lifetime of the organic light emitting device as compared with a compound in which only a triazine (or pyrimidine) was substituted in dibenzofuran (or dibenzothiophene).

Further, when comparing the Experimental Examples in Table 1 and the Comparative Experimental Example 10 in Table 2, it was confirmed that the compounds of Formula 1 according to the present disclosure were remarkably excellent in terms of driving voltage, efficiency, and lifetime of the organic light emitting device as compared with a compound in which only a heteroaryl group other than cyano group was substituted in dibenzofuran (or dibenzothiophene).

Further, when comparing the Experimental Examples in Table 1 and the Comparative Experimental Example 11 in Table 2, it was confirmed that the compounds of Formula 1 according to the present disclosure were remarkably excellent in terms of driving voltage, efficiency, and lifetime of the organic light emitting device as compared in which triazine (or pyrimidine) and a cyano group each are substituted in different phenyl groups of dibenzofuran (or dibenzothiophene).

DESCRIPTION OF REFERENCE NUMERALS

1: substrate
2: anode
3: light emitting layer
4: cathode
5: hole injection layer
6: hole transport layer
7: light emitting layer
8: electron transport layer

The invention claimed is:
1. A compound represented by Formula 1:

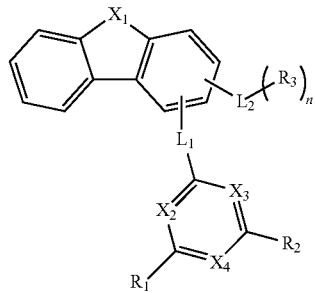

[Formula 1]

in Formula 1,
$X_1$ is O or S,
$X_2$, $X_3$ and $X_4$ are each independently N or CH,
$R_1$ and $R_2$ are each independently a substituted or unsubstituted $C_{6-60}$ aryl; or a substituted or unsubstituted $C_{2-60}$ heteroaryl containing at least one of N, O and S,
$R_3$ is each independently a $C_{6-60}$ aryl substituted with one or two cyano groups,
n is an integer of 1 or 2, and
$L_1$ and $L_2$ are each independently a single bond, or any one selected from the group consisting of the following:

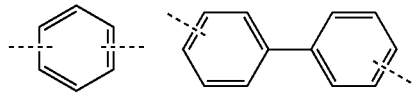

-continued
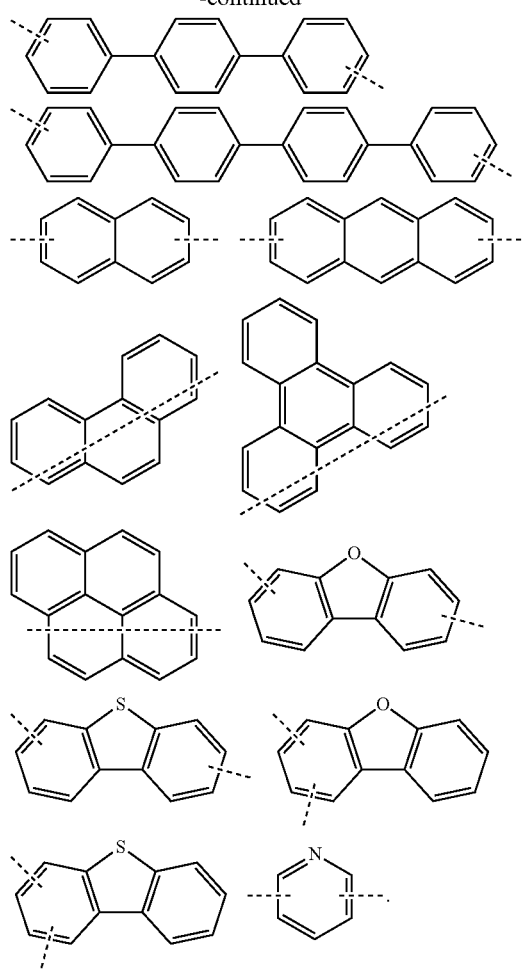
2. The compound of claim 1, wherein at least two of $X_2$, $X_3$ and $X_4$ are N.
3. The compound of claim 1, wherein
$L_1$ and $L_2$ are each independently a single bond,
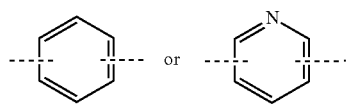 or
4. The compound of claim 1, wherein
$R_1$ and $R_2$ are each independently any one selected from the group consisting of the following:
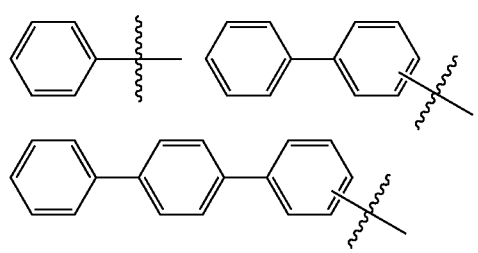
-continued
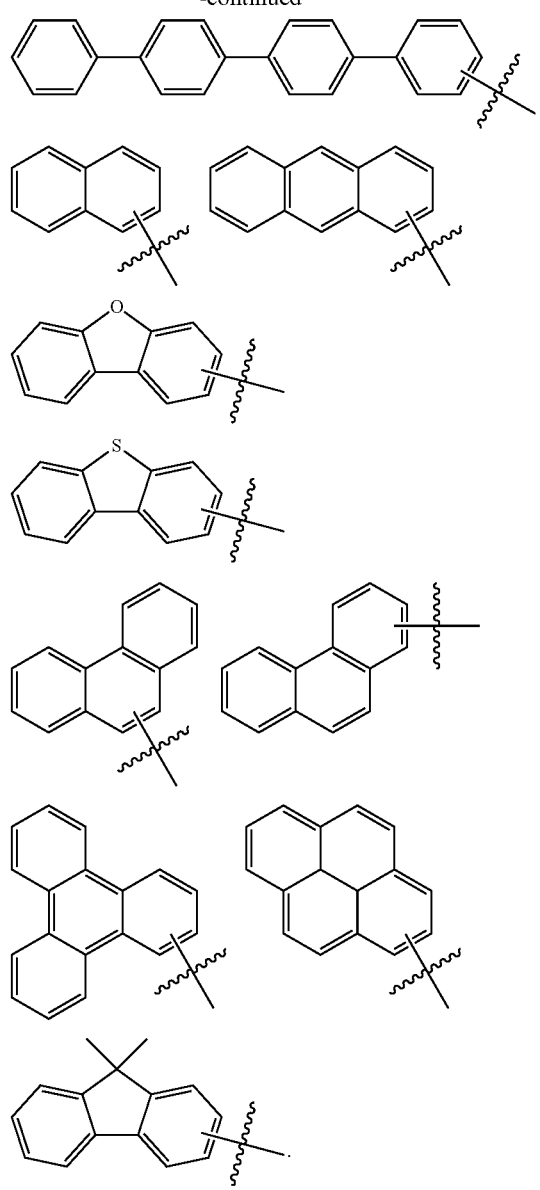
5. The compound of claim 1, wherein
$R_1$ and $R_2$ are each independently
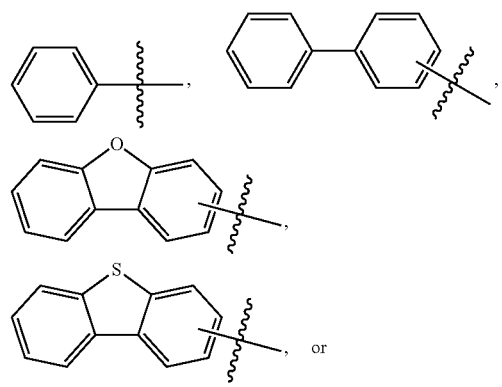

-continued

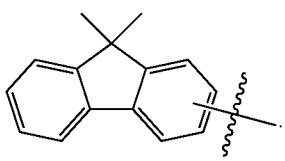

6. The compound of claim 1, wherein
each $R_3$ is independently any one selected from the group consisting of phenyl substituted with one or two cyano groups, biphenylyl substituted with one or two cyano groups, terphenylyl substituted with one or two cyano groups, or dimethylfluorenyl substituted with one or two cyano groups.

7. The compound of claim 1, wherein
the compound represented by Formula 1 is any one selected from the group consisting of the following:

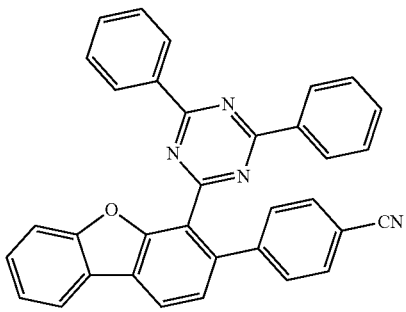

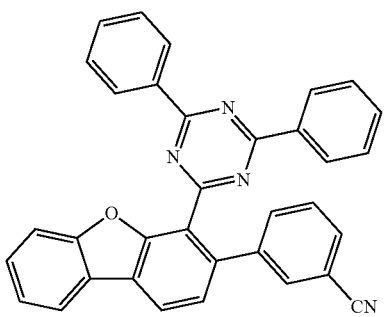

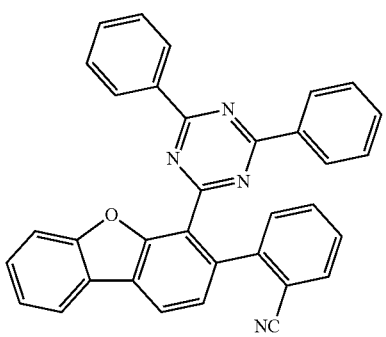

-continued

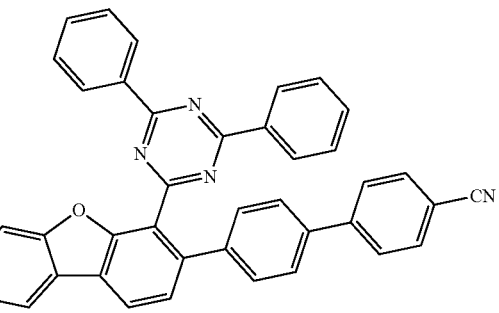

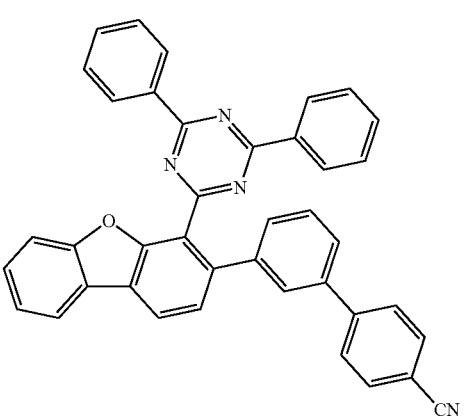

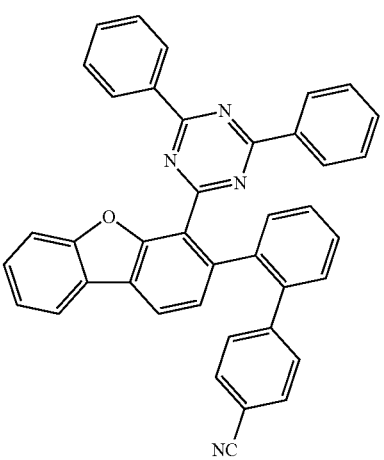

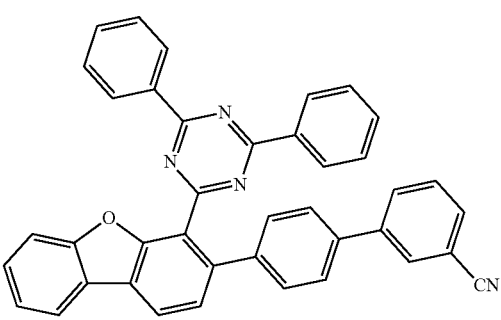

97
-continued
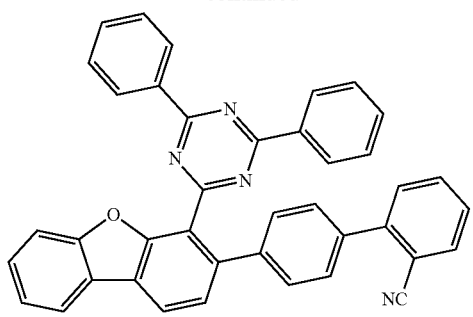
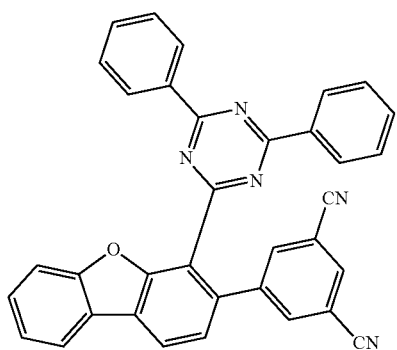
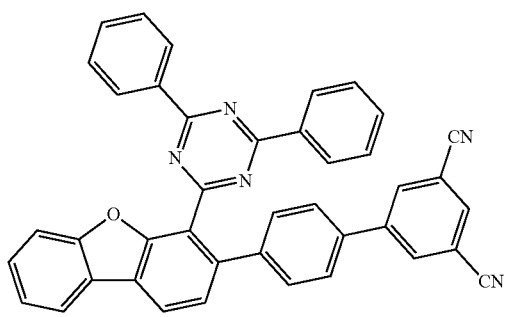
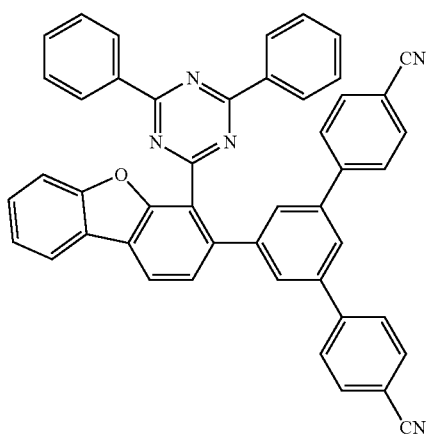
98
-continued
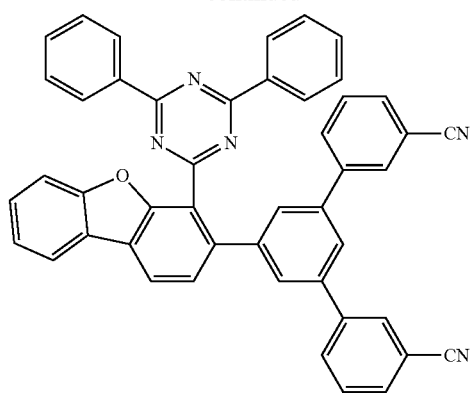
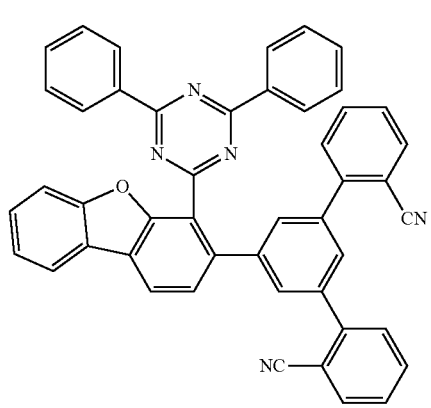
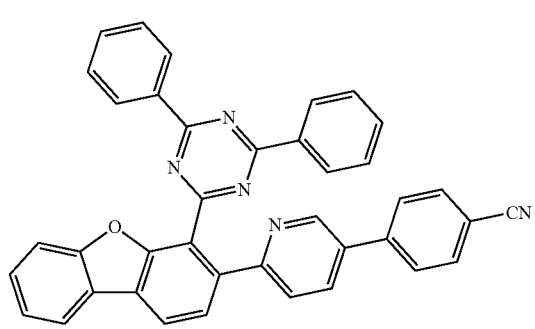
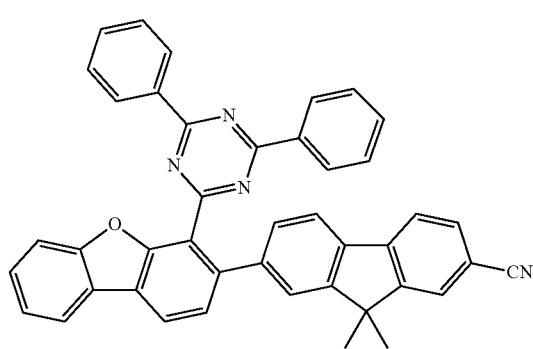

99
-continued
100
-continued
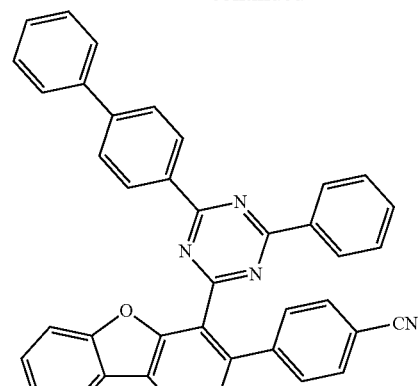
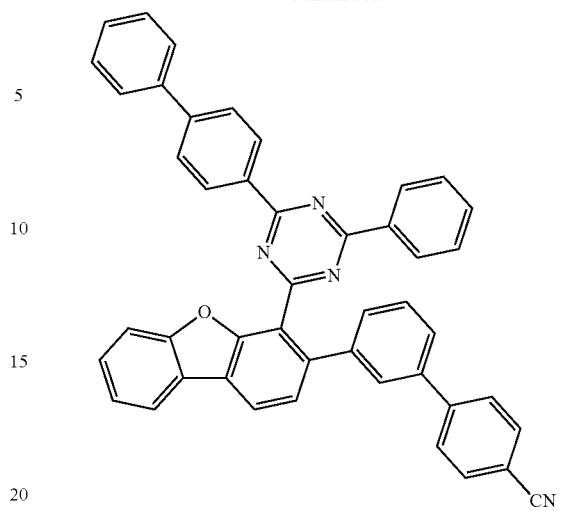

101
-continued
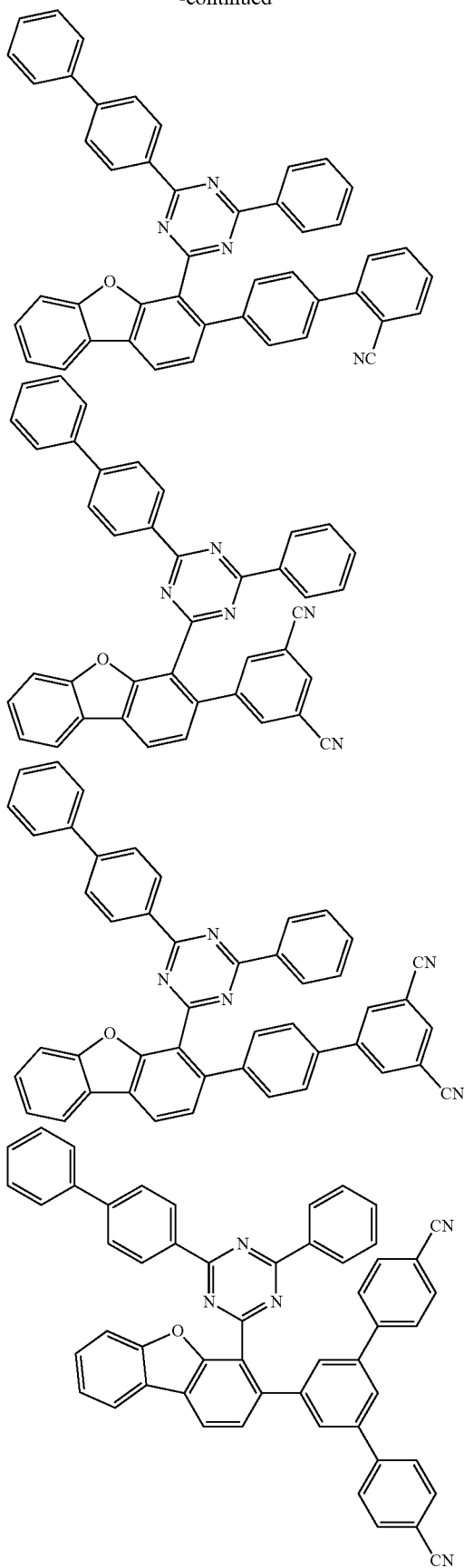
102
-continued
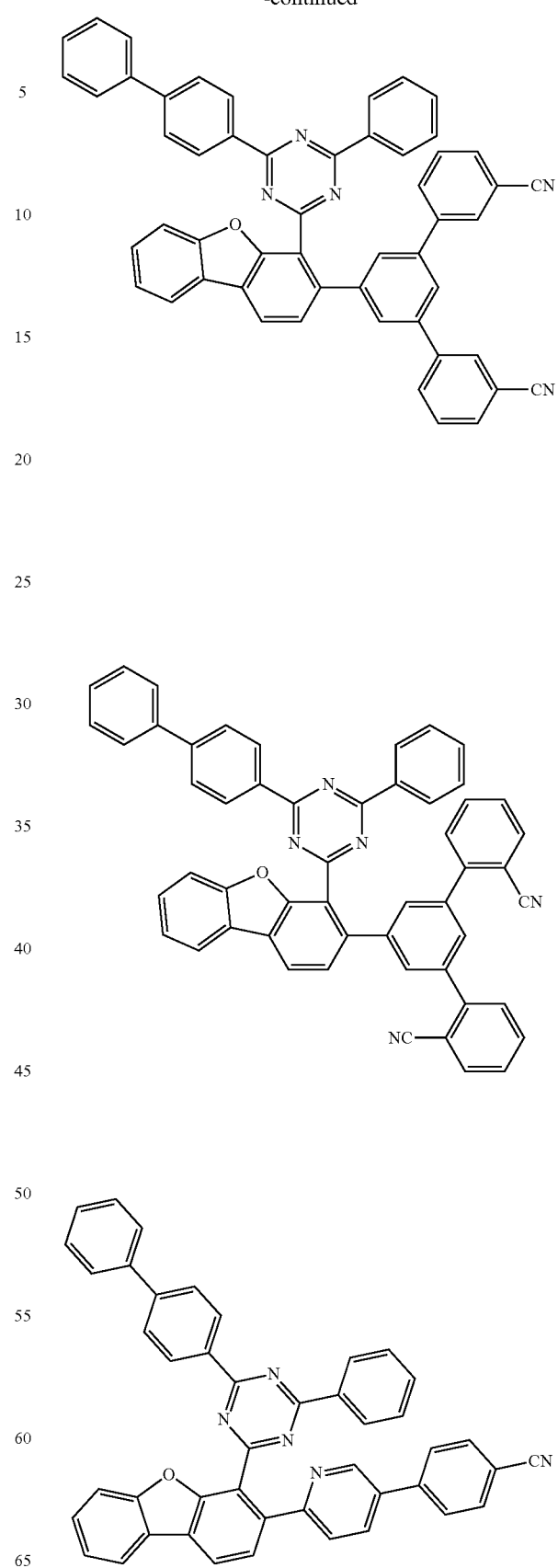

103
-continued
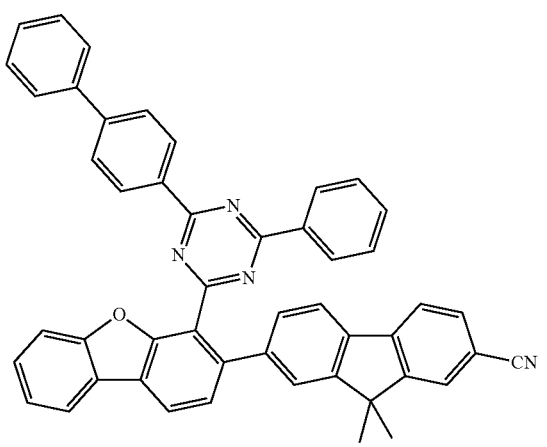
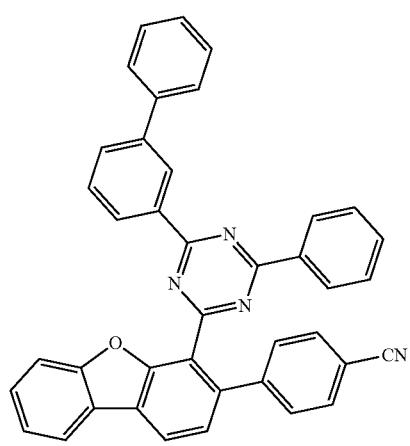
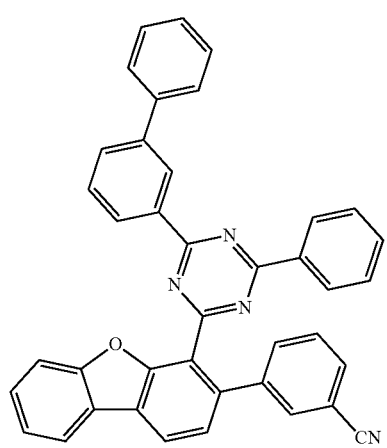
104
-continued
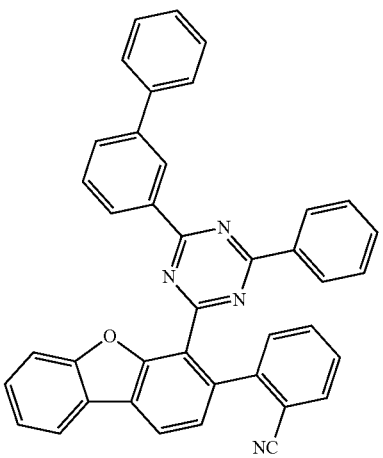
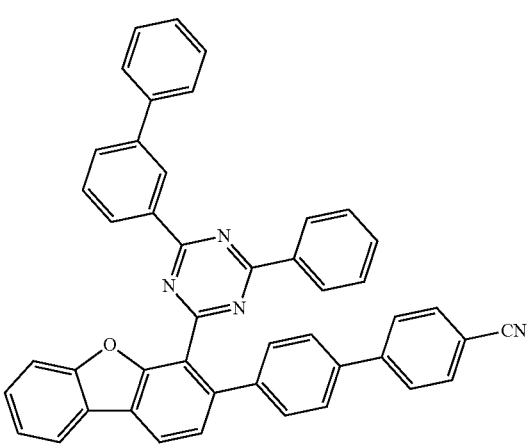
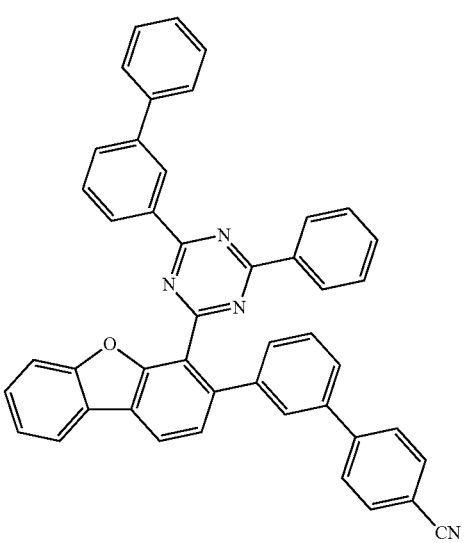

105
-continued
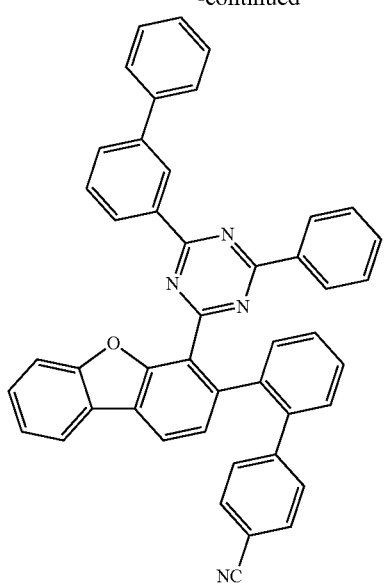
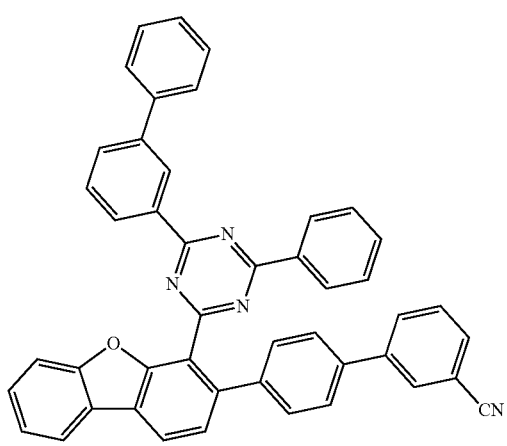
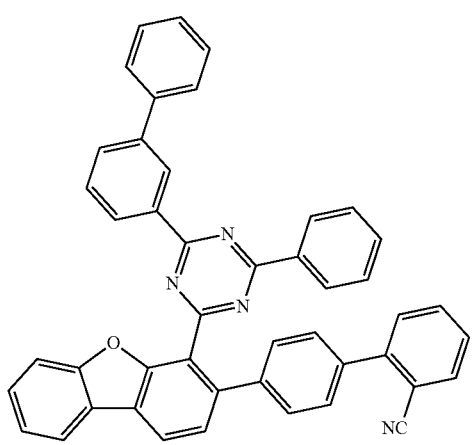
106
-continued
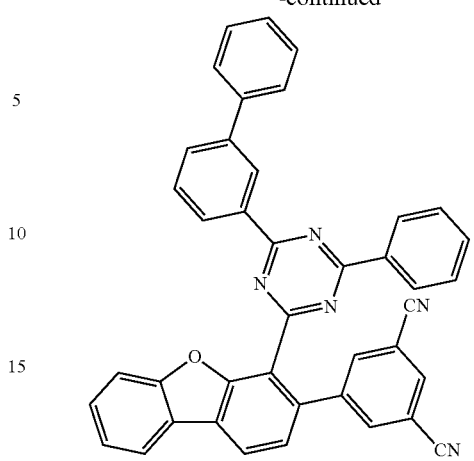
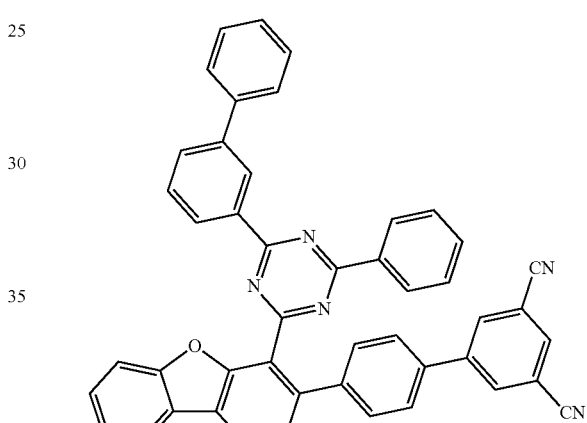
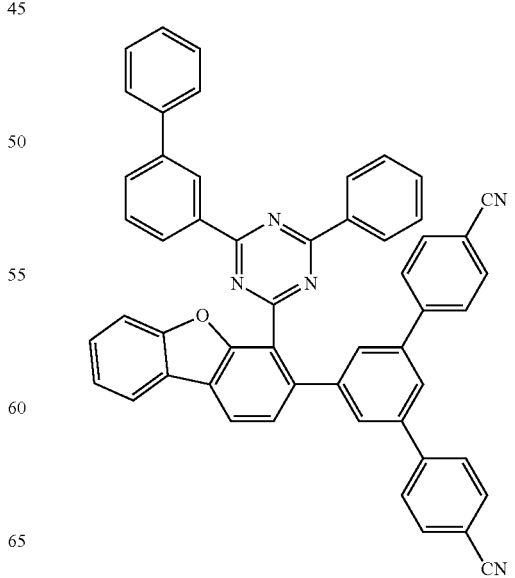

107
-continued
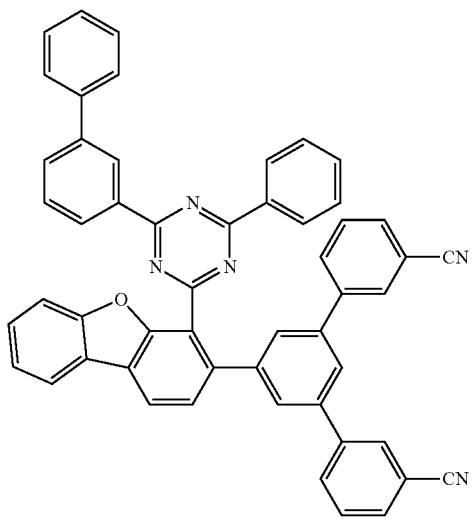
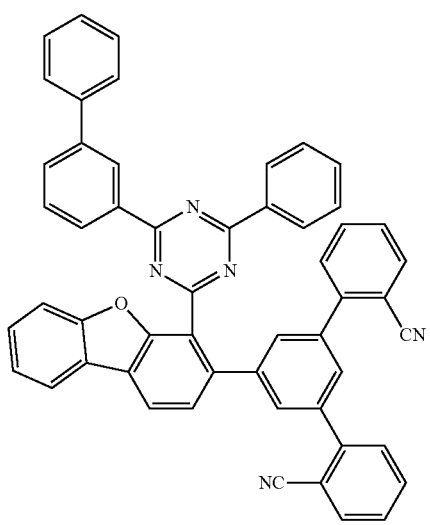
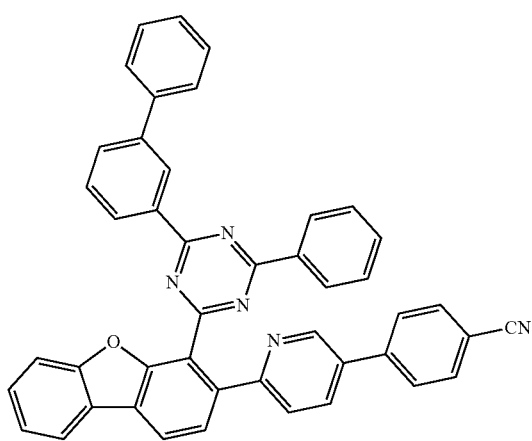 [SMILES: N#Cc1ccc(-c2ccc(-c3ccc4c(oc5ccccc54)c3-c3nc(-c4ccccc4)nc(-c4cccc(-c5ccccc5)c4)n3)nc2)cc1]
108
-continued
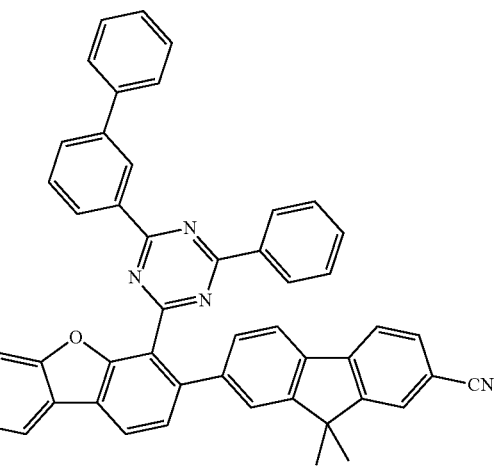
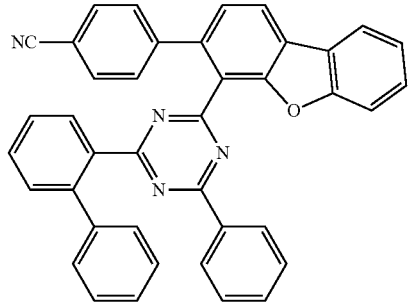
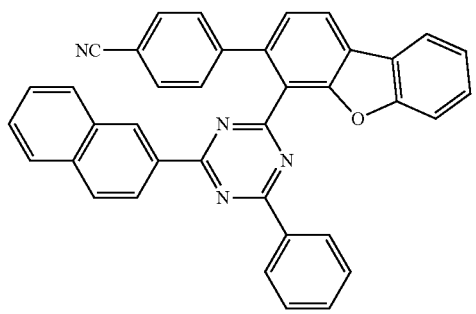
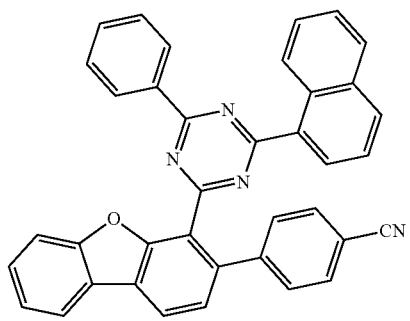

109
-continued
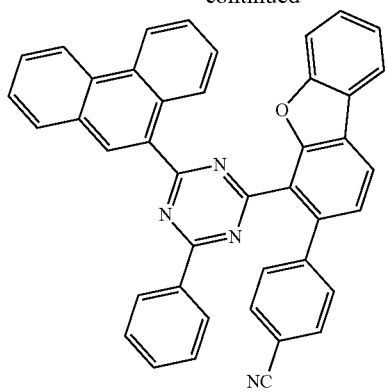
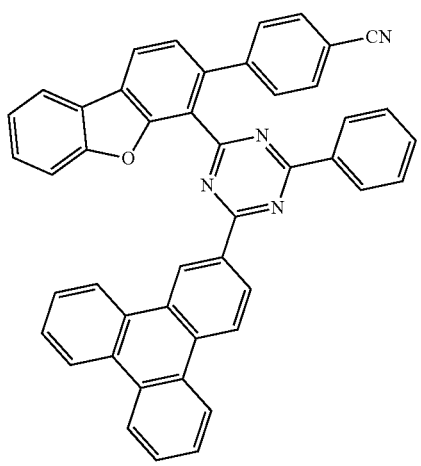
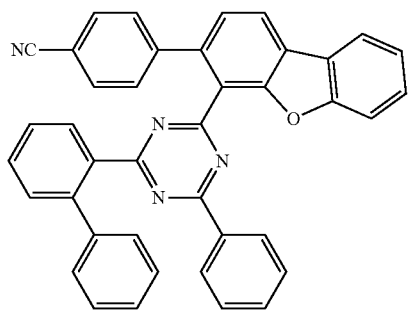
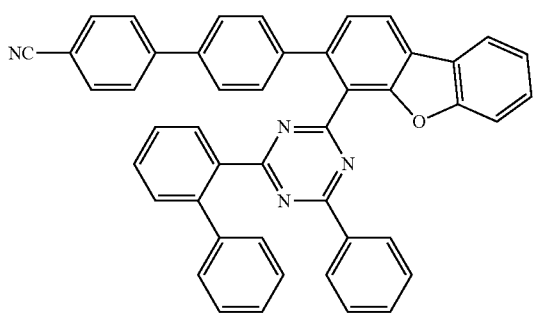
110
-continued
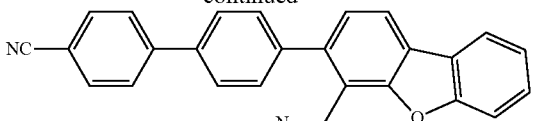
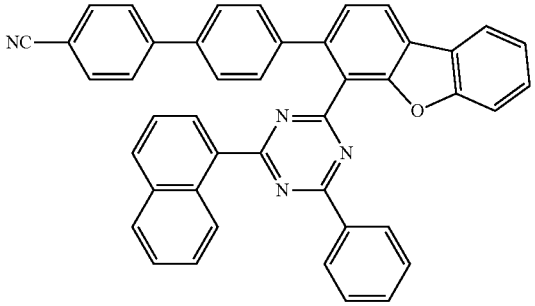
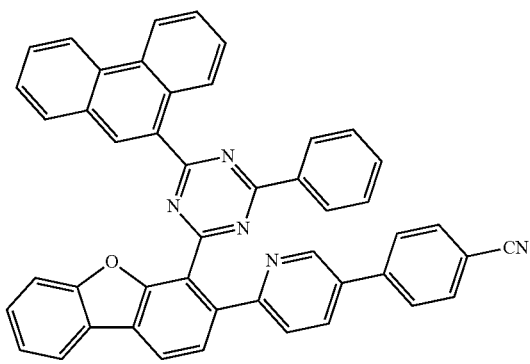
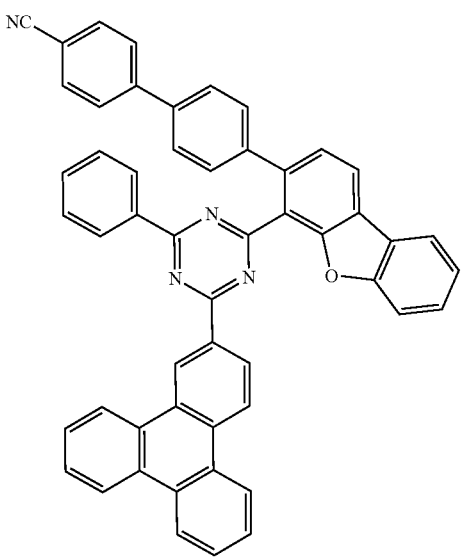

111
-continued
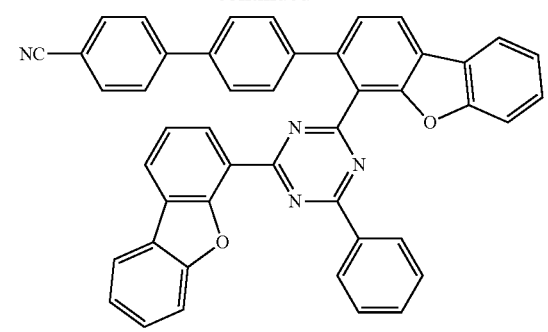
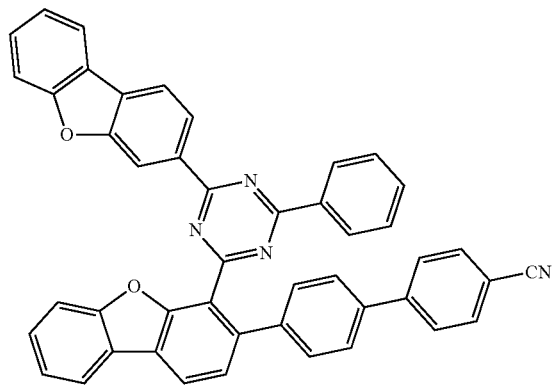
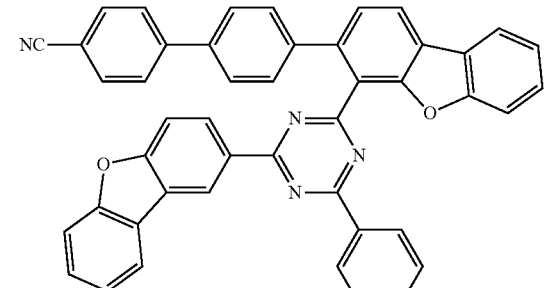
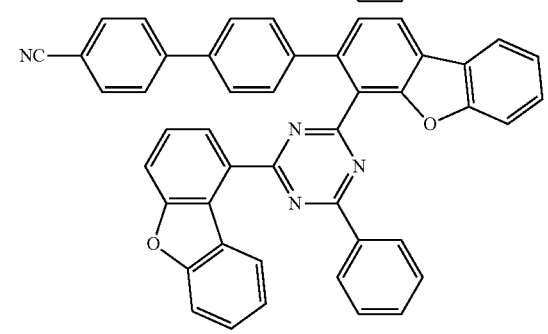
112
-continued
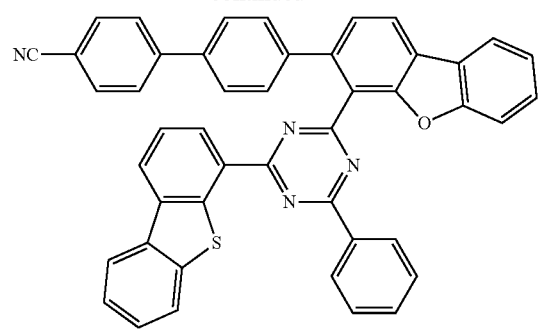
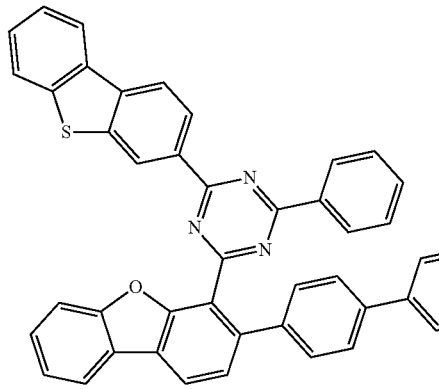
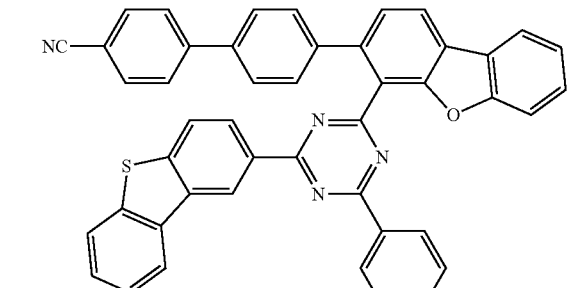
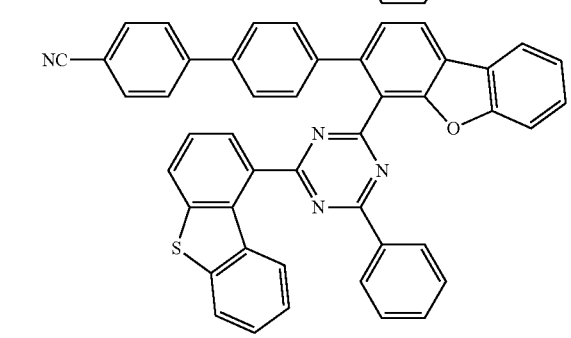

113
-continued
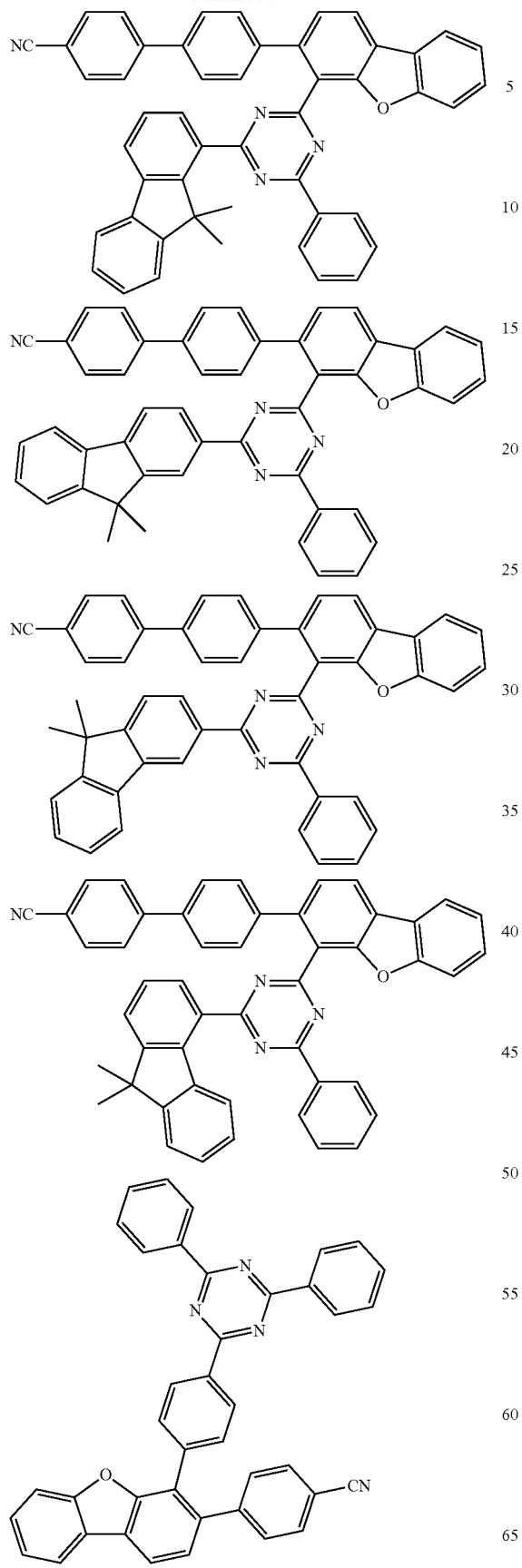
114
-continued
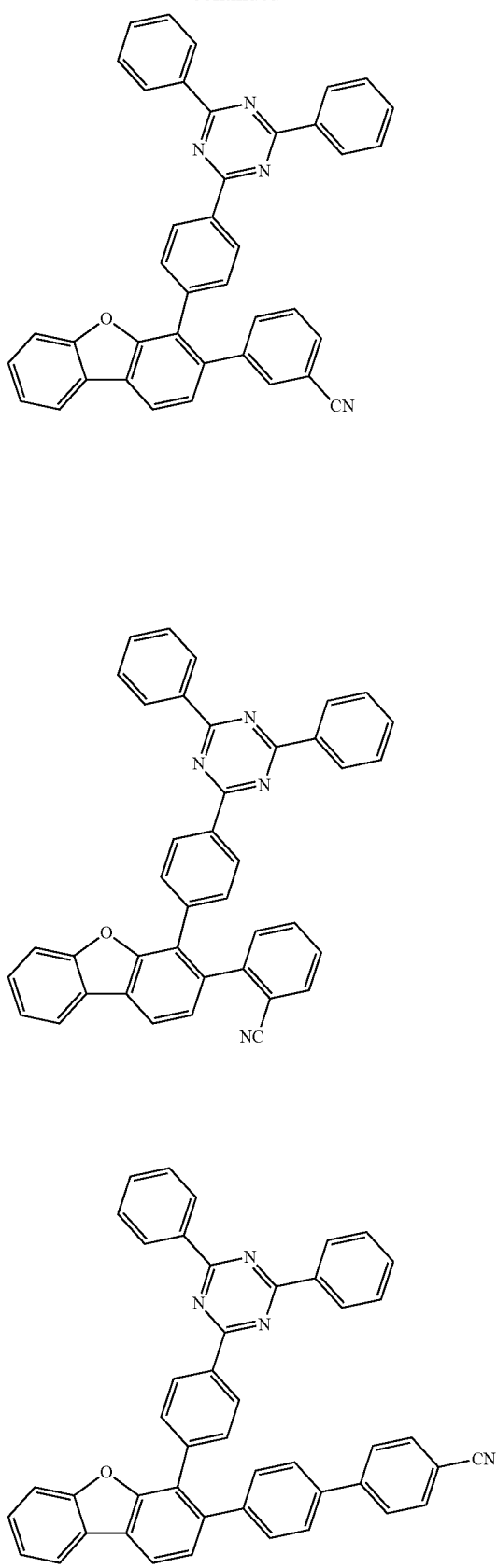

115
-continued
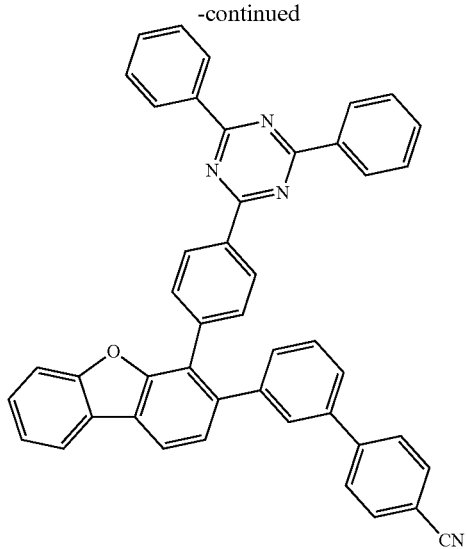
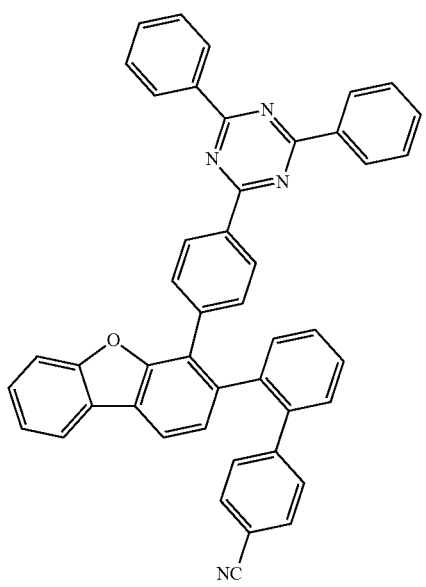
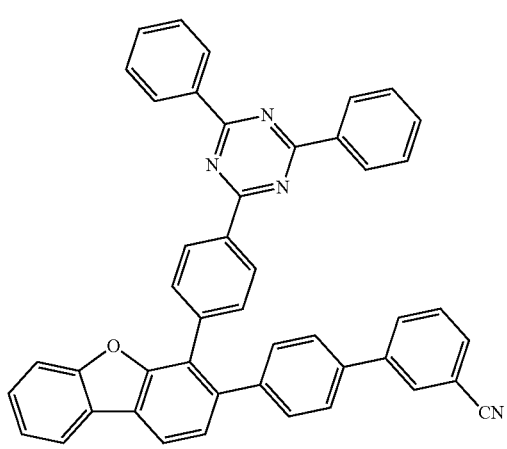
116
-continued
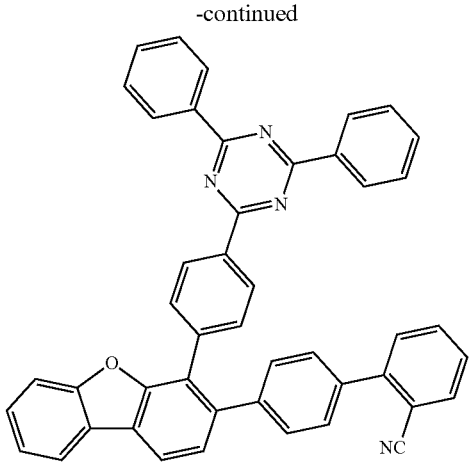
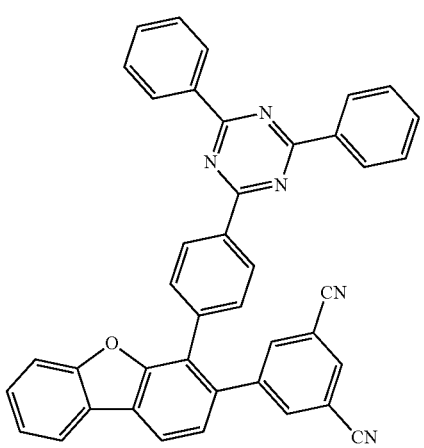 [SMILES: N#Cc1ccc(-c2ccc3c(sc4ccccc43)c2-c2ccc(-c3cc(-c4ccccc4)nc(-c4ccccc4)n3)cc2)cc1]
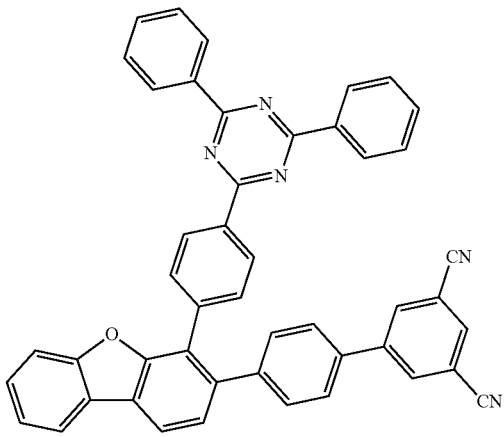

117
-continued
118
-continued
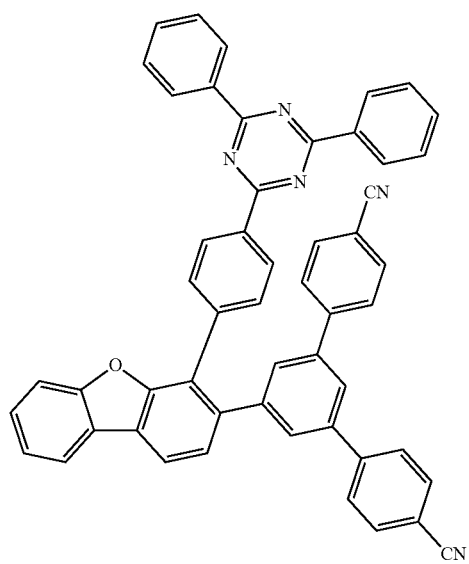
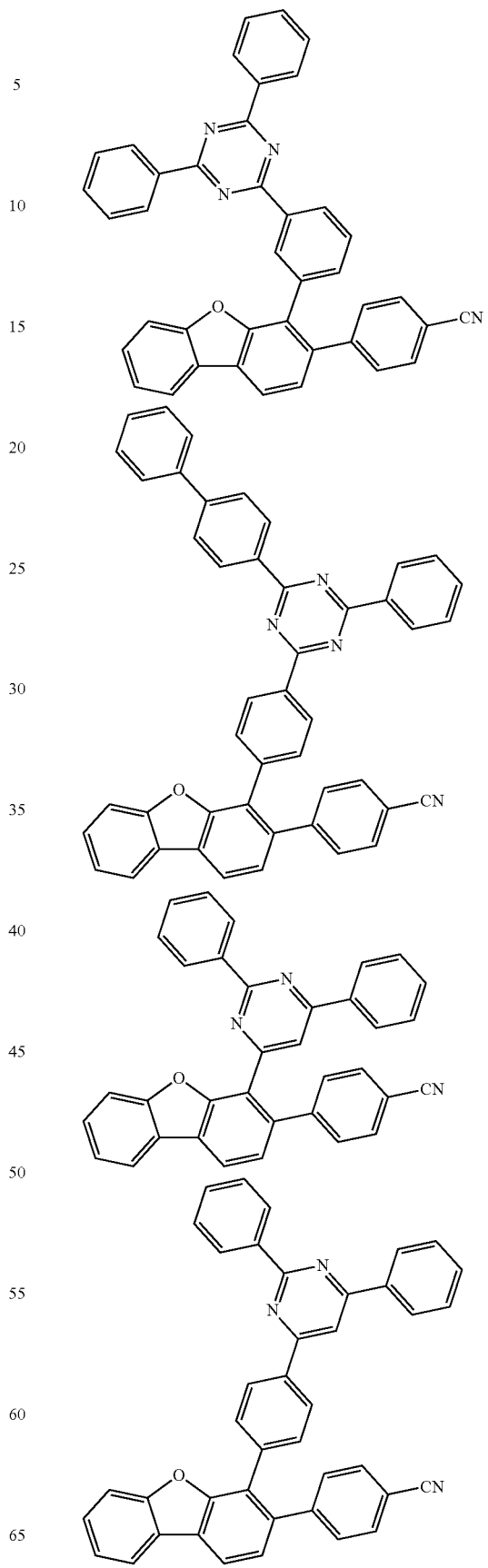

119
-continued
120
-continued
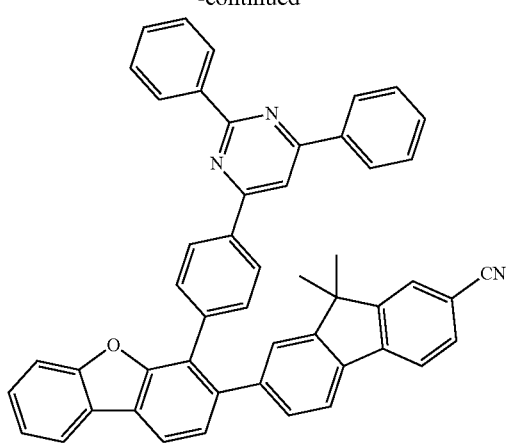
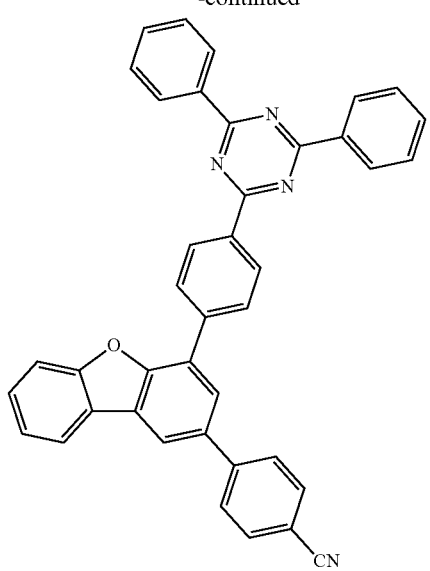
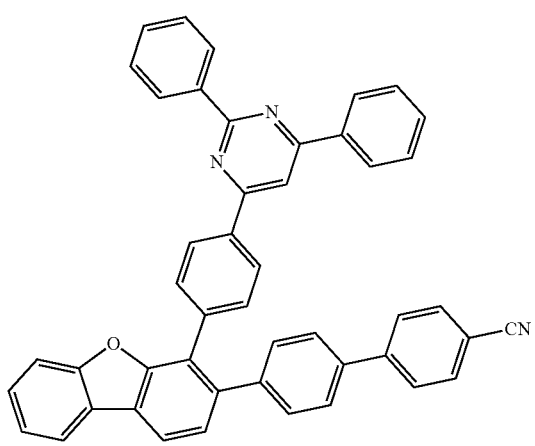
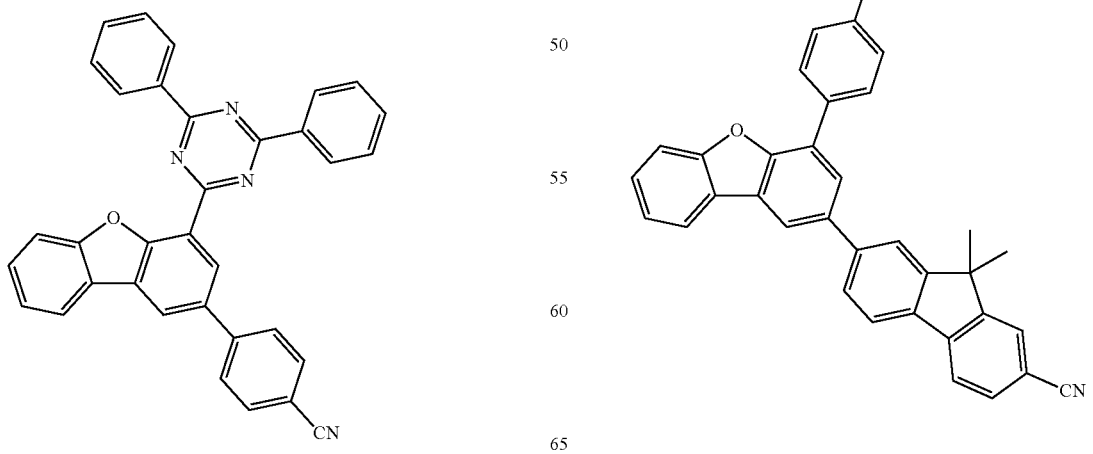

121
-continued
122
-continued
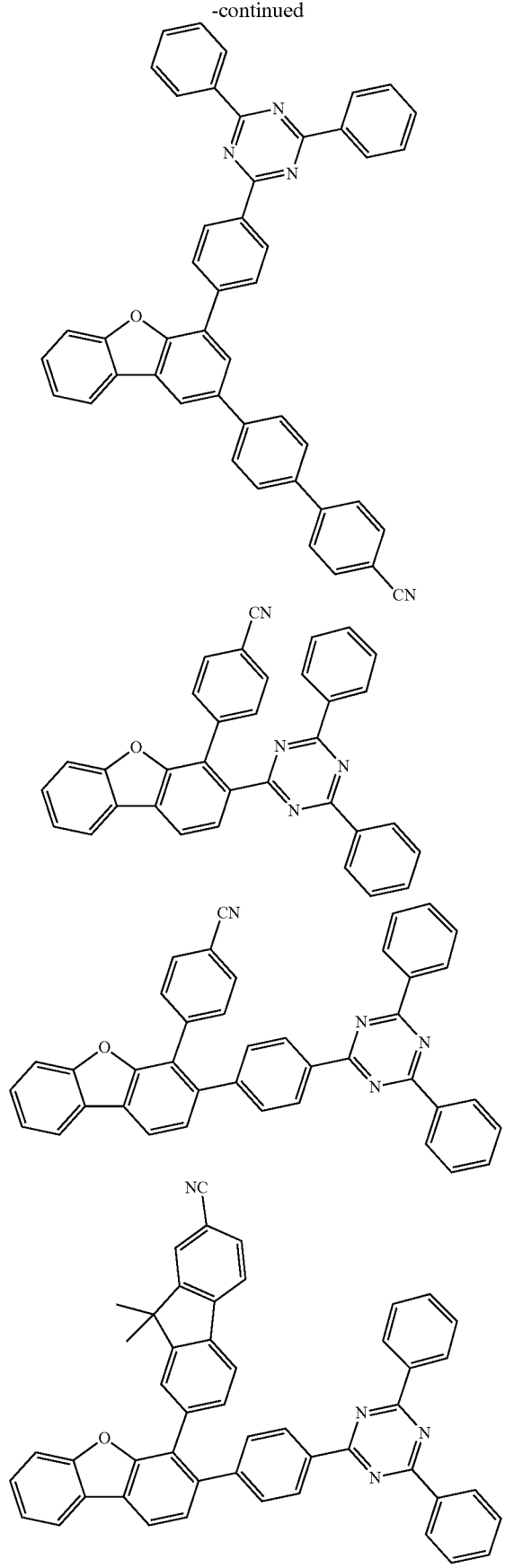
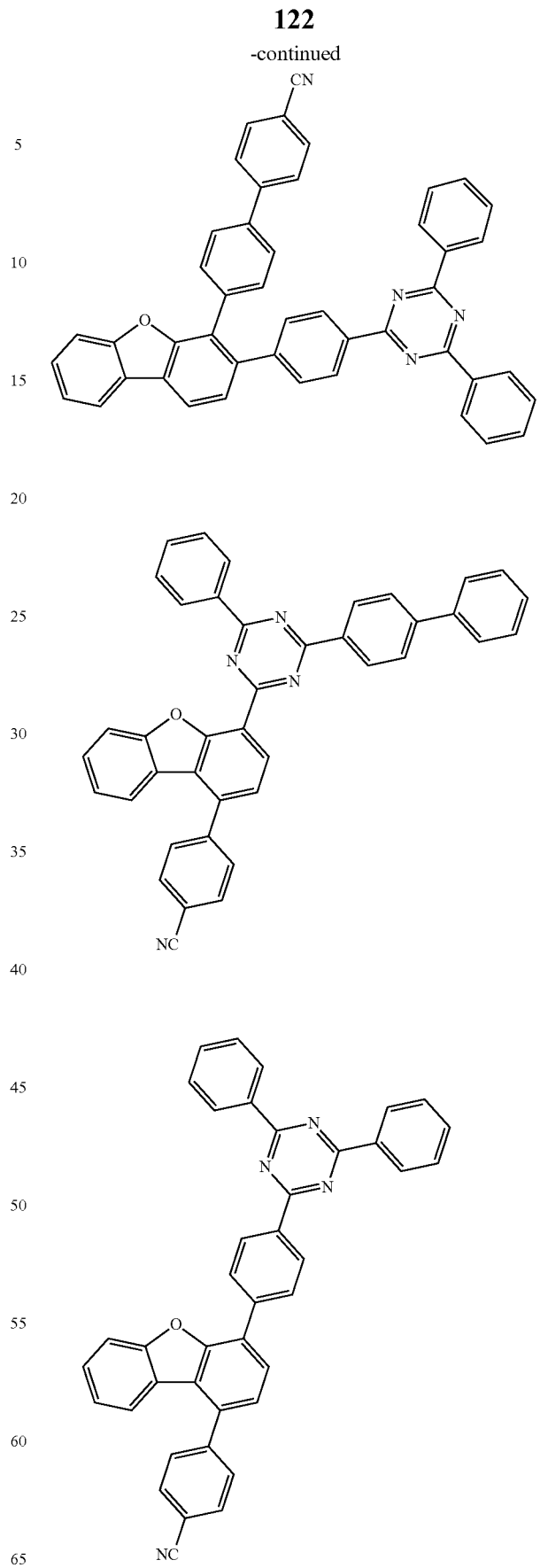

123
-continued
124
-continued
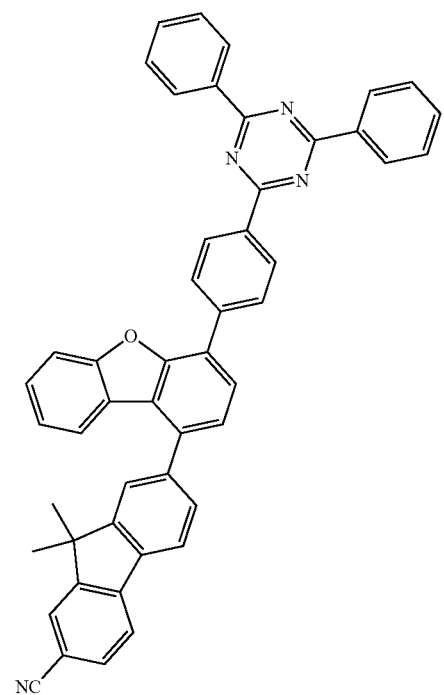
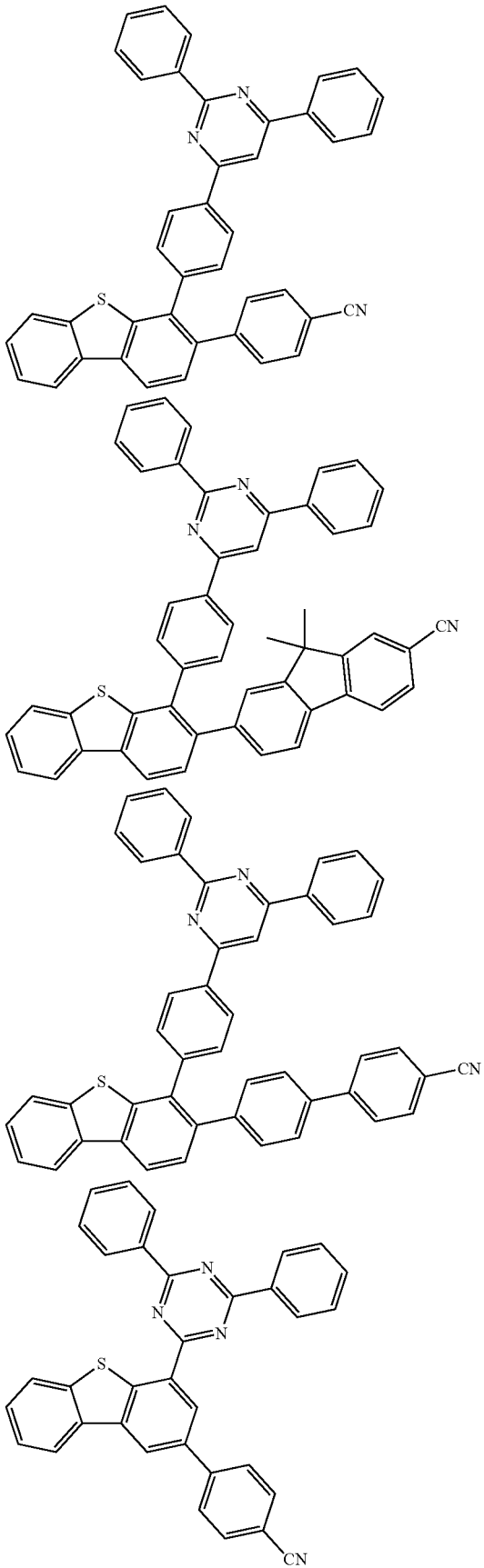

125
-continued
126
-continued
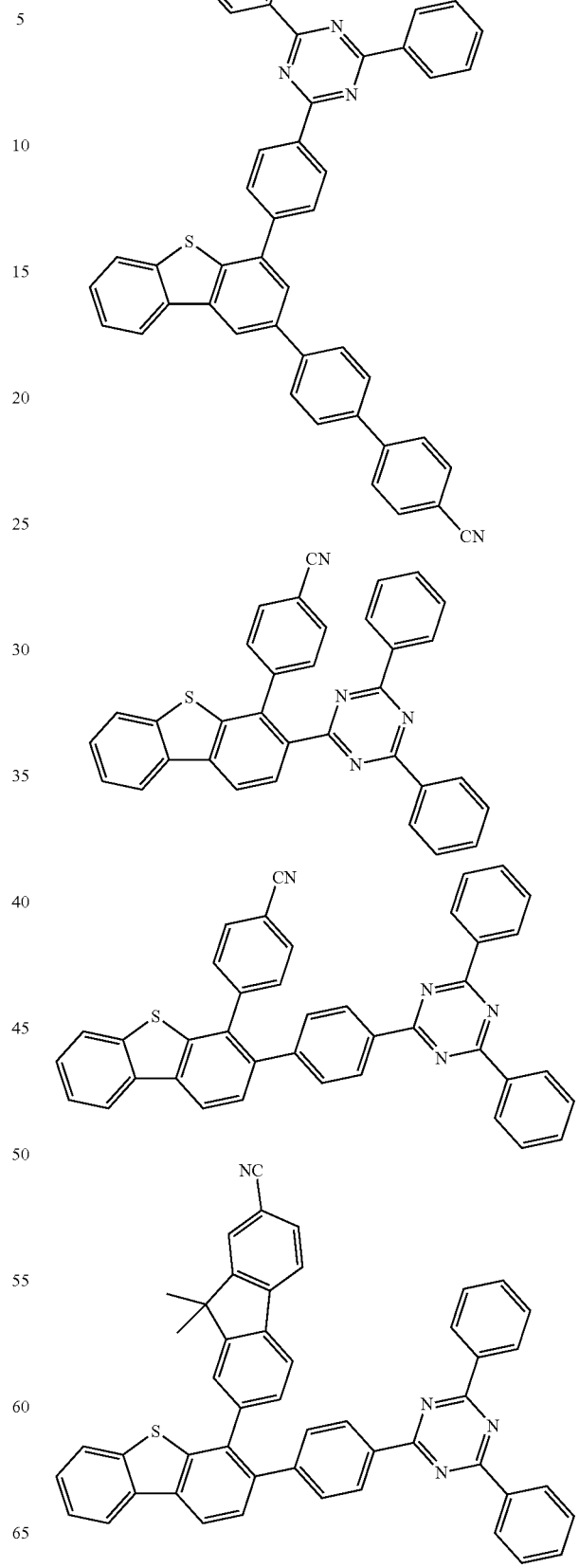

127
-continued
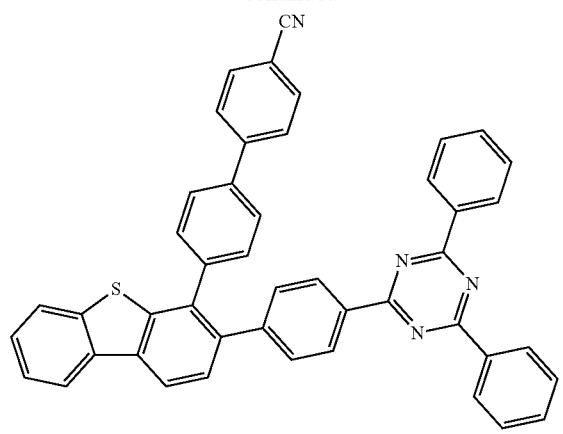
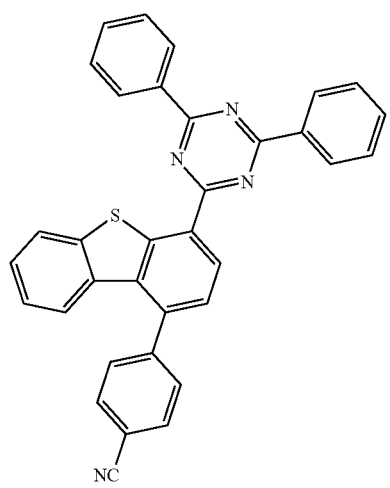
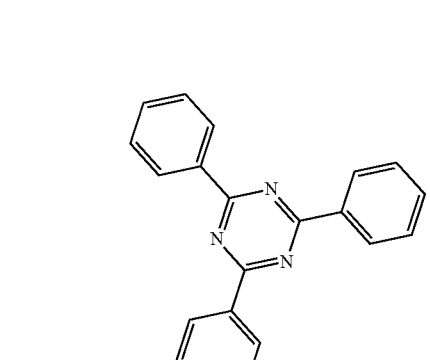
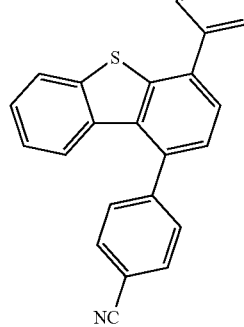
128
-continued
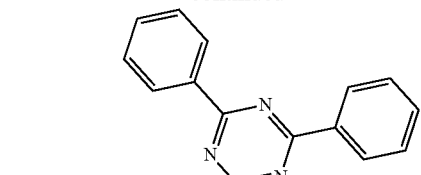
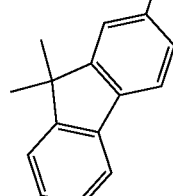
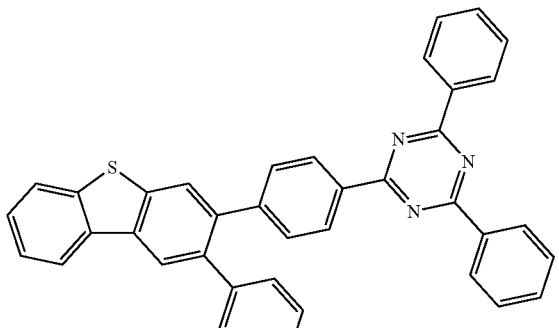
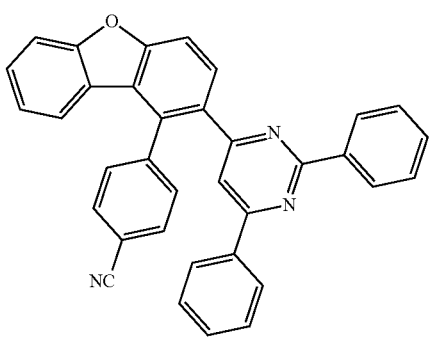

129
-continued
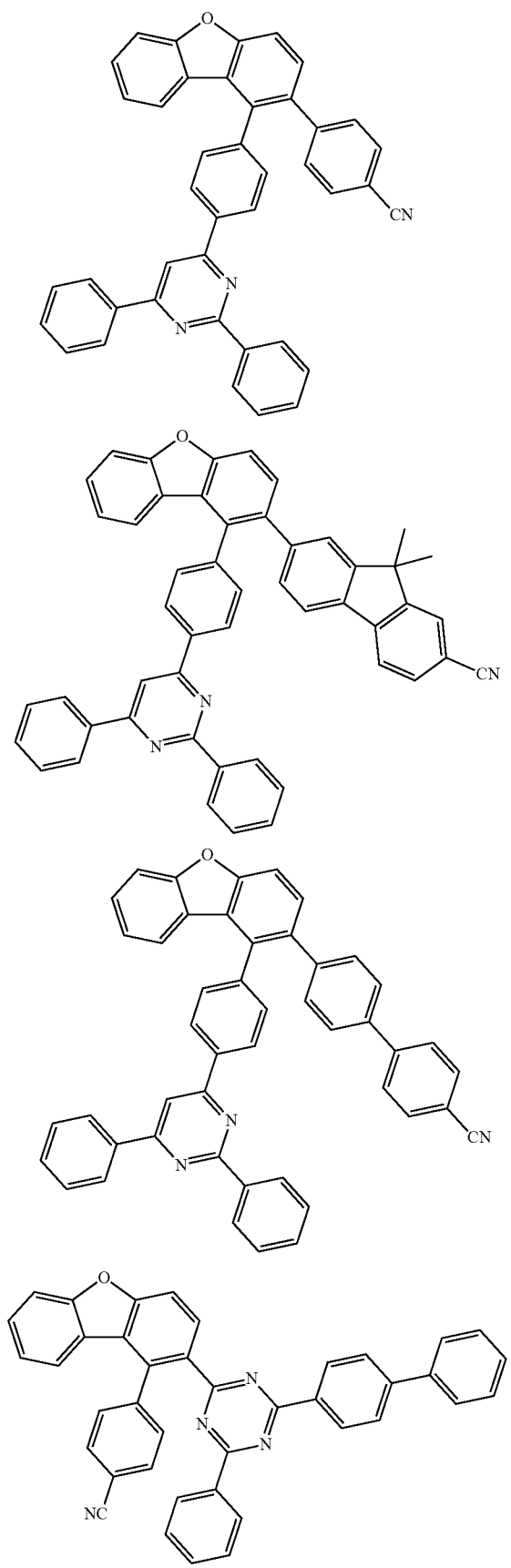
130
-continued
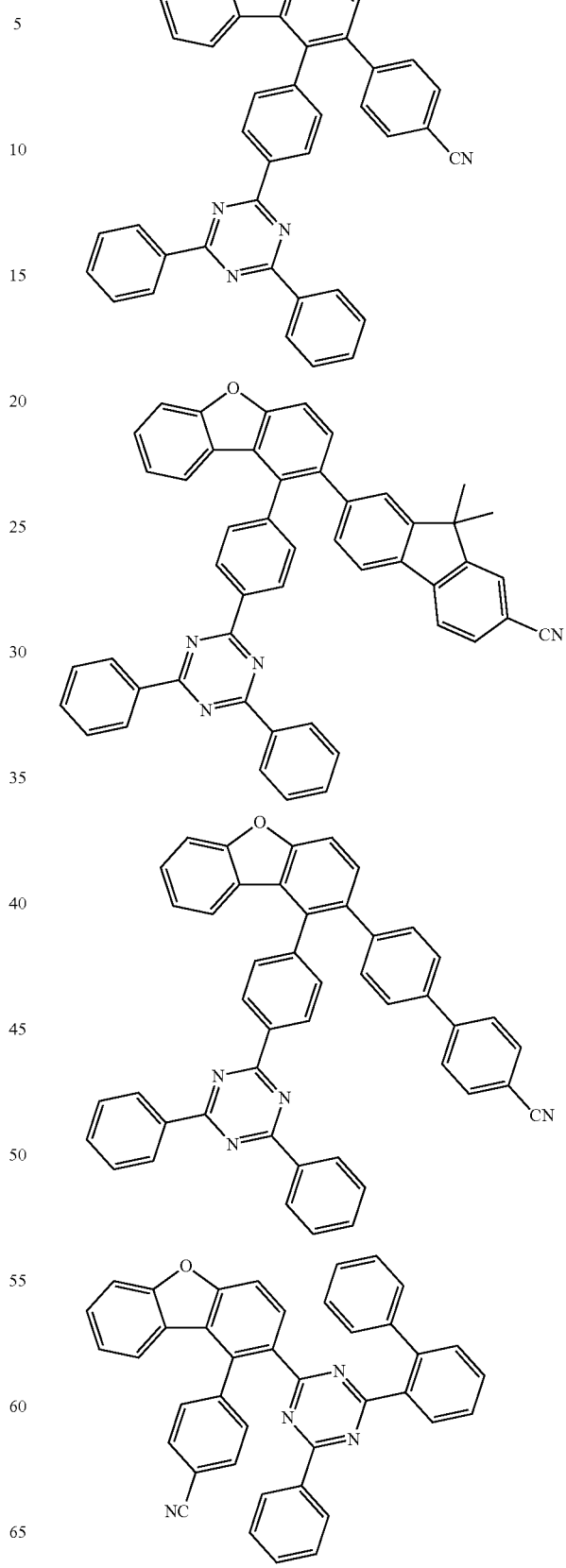

131
-continued
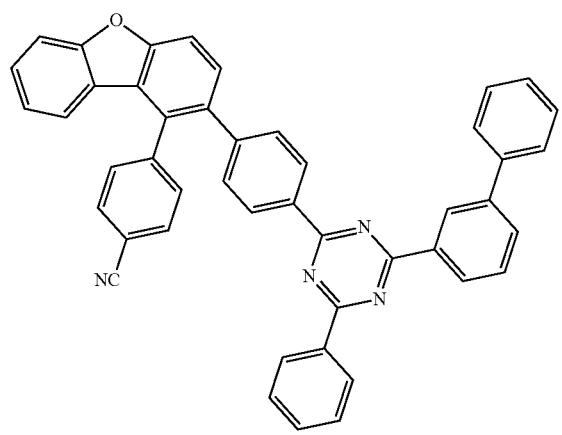
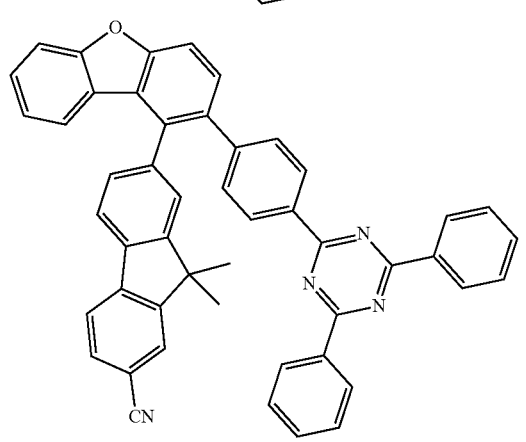
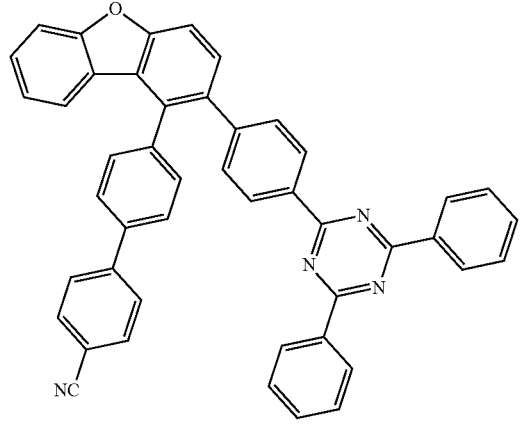
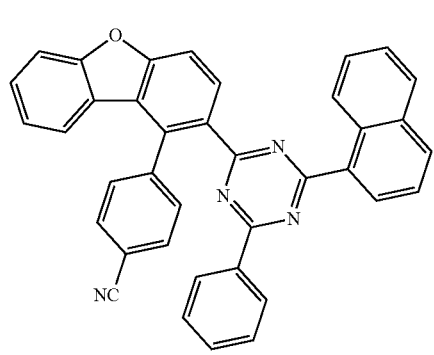
132
-continued
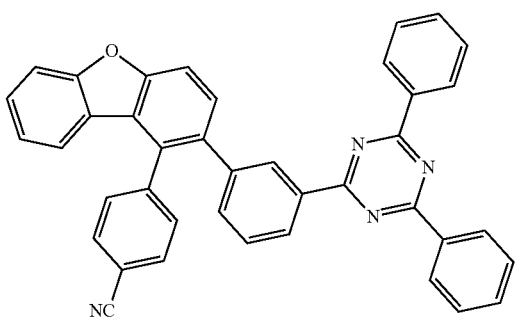
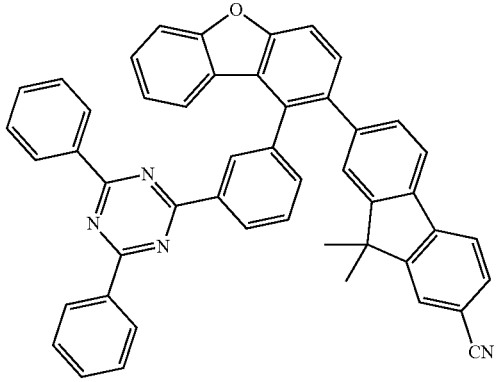
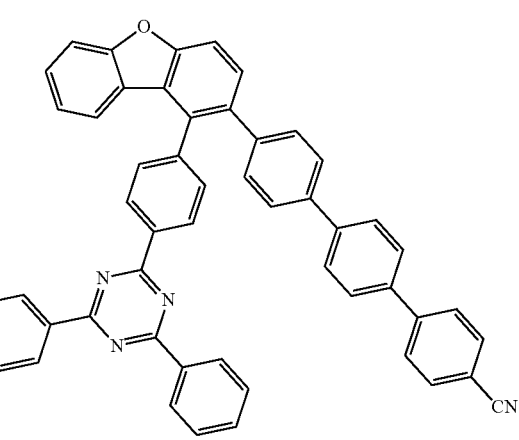
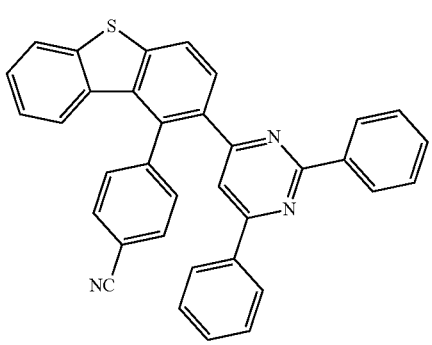

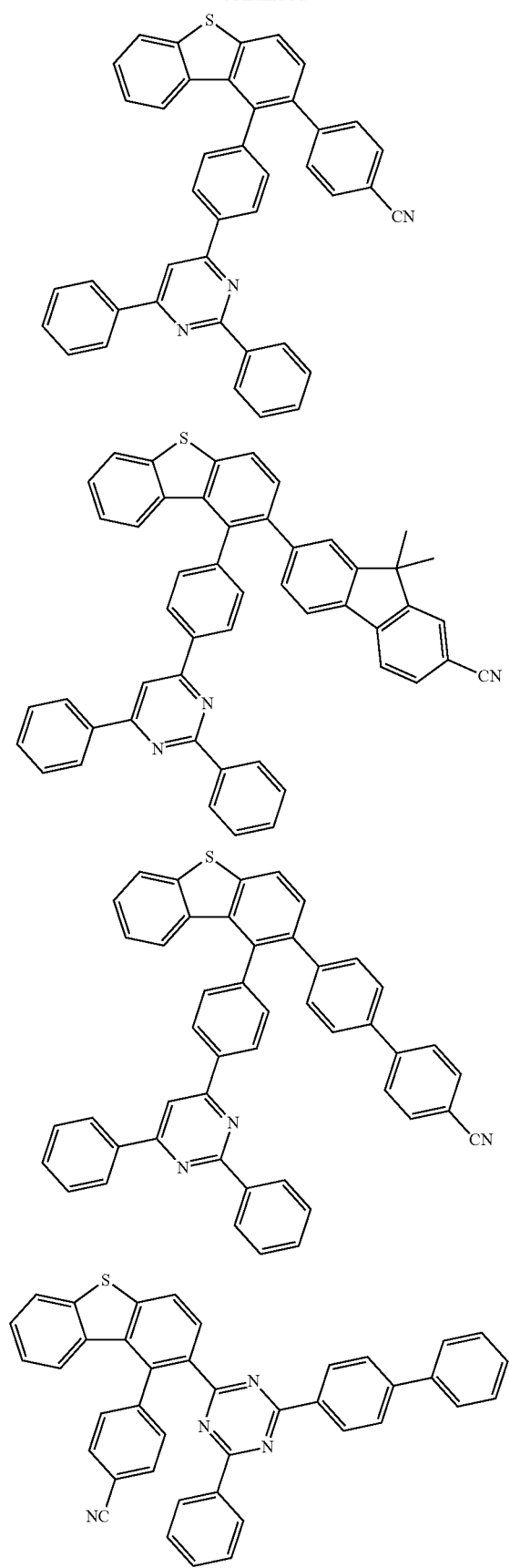

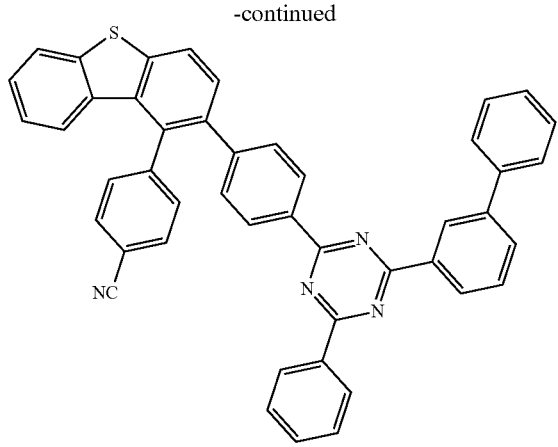

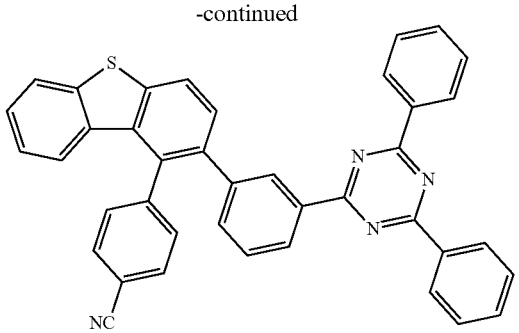

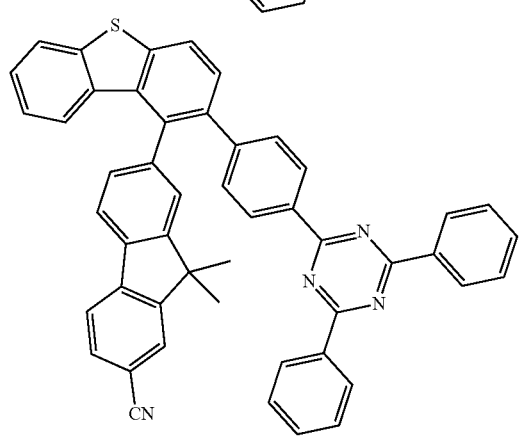

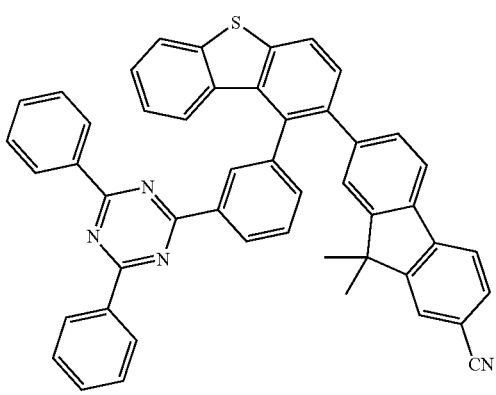

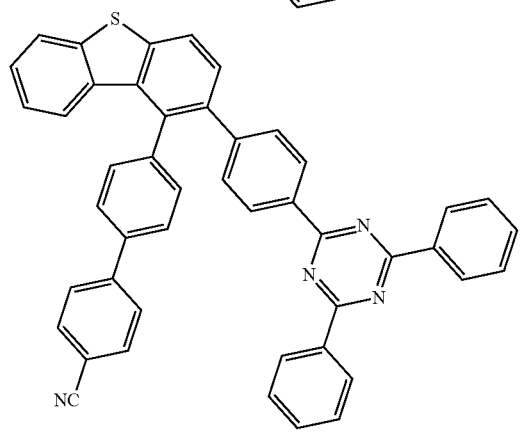

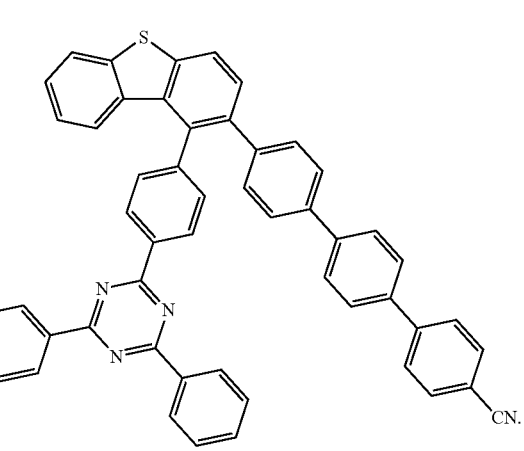

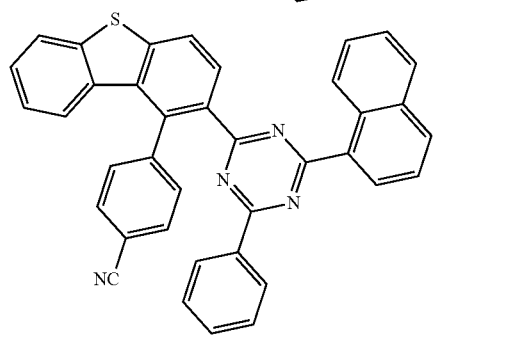

8. An organic light emitting device comprising a first electrode; a second electrode provided to face the first electrode; and at least one layer of organic material layers provided between the first electrode and the second electrode, wherein the at least one layer of the organic material layers includes the compound according to claim 1.

9. The organic light emitting device of claim, 8, wherein the at least one layer of the organic material layers comprising the compound is an electron injection layer; an electron transport layer; or a layer simultaneously performing electron injection and electron transport.

* * * * *